United States Patent
Arico et al.

(10) Patent No.: US 9,249,197 B2
(45) Date of Patent: Feb. 2, 2016

(54) MENINGOCOCCUS ADHESINS NADA, APP AND ORF 40

(71) Applicant: Novartis Vaccines and Diagnostics SRL, Siena (IT)

(72) Inventors: Maria Arico, Siena (IT); Maurizio Comanducci, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 14/224,031

(22) Filed: Mar. 24, 2014

(65) Prior Publication Data

US 2014/0294884 A1    Oct. 2, 2014

Related U.S. Application Data

(63) Continuation of application No. 12/775,457, filed on May 6, 2010, now abandoned, which is a continuation of application No. 10/484,703, filed as application No. PCT/IB02/03396 on Jul. 26, 2002, now abandoned.

(30) Foreign Application Priority Data

Jul. 27, 2001   (GB) .................................. 0118401.9
Sep. 6, 2001    (GB) .................................. 0121591.2
May 14, 2002    (GB) .................................. 0211025.2

(51) Int. Cl.
   *C07K 14/22*     (2006.01)
   *A61K 39/00*     (2006.01)

(52) U.S. Cl.
   CPC .................. *C07K 14/22* (2013.01); *A61K 39/00* (2013.01); *A61K 2039/53* (2013.01)

(58) Field of Classification Search
   None
   See application file for complete search history.

(56) References Cited

U.S. PATENT DOCUMENTS

| | | | |
|---|---|---|---|
| 7,348,006 | B2 | 3/2008 | Contorni et al. |
| 7,576,176 | B1 | 8/2009 | Fraser et al. |
| 2004/0092711 | A1 | 5/2004 | Arico |
| 2004/0110670 | A1 | 6/2004 | Arico et al. |
| 2005/0222385 | A1 | 10/2005 | Pizza |
| 2005/0232936 | A1 | 10/2005 | Arico et al. |
| 2006/0051840 | A1 | 3/2006 | Arico et al. |
| 2006/0171957 | A1 | 8/2006 | Pizza |
| 2006/0240045 | A1 | 10/2006 | Berthet et al. |
| 2007/0082014 | A1 | 4/2007 | Costantino |
| 2008/0241180 | A1 | 10/2008 | Contorni |
| 2010/0267931 | A1 | 10/2010 | Arico et al. |

FOREIGN PATENT DOCUMENTS

| | | |
|---|---|---|
| EP | 822831 B1 | 11/1999 |
| EP | 0978565 A | 2/2000 |
| WO | WO-99/57280 A | 11/1999 |
| WO | WO-99/58683 | 11/1999 |
| WO | WO-99/61053 | 12/1999 |
| WO | WO-00/11182 | 3/2000 |
| WO | WO-00/18434 A | 4/2000 |
| WO | WO-00/22430 A2 | 4/2000 |
| WO | WO-00/66791 | 11/2000 |
| WO | WO-01/031019 | 5/2001 |
| WO | WO-03/009869 A1 | 2/2003 |
| WO | WO-03/020756 A | 3/2003 |
| WO | WO-2004/032958 A1 | 4/2004 |

OTHER PUBLICATIONS

Bowe et al. (Jul. 2004) "Mucosal vaccination against serogroup B meningococci: induction of bacterial antibodies and cellular immunity following intranasal immunization with NadA of *Neisseria meningitides* and mutants of *Escherichia coli* heat-labile enterotoxin," Infection and Immunity, 72: 4052-4060.

Capecchi et al. (2005) "*Neisseria meningitides* NadA is a new invasion which promotes bacterial adhesion to and penetration into human epithelial cells," Molecular Microbiology, 55: 687-698.

Comanducci et al. (Jul. 2004) "NadA diversity and carriage in *Neisseria meningitides*," Infection and Immunity, 72: 4217-4223.

Comanducci, M. (2002). "NadA, a Novel Vaccine Candidate of Neisseria Meningitides," Journal of Experimental Medicine 195(11): 1445-1454.

Jacobsson et al. (2009). "Prevalence and sequence variations of the genes encoding the five antigens included in the novel 5CVMB vaccine covering group B meningococcal disease" Vaccine. 27:1579-1584.

Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.

Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.

Martin et al. (2003). "Experimentally revised repertoire of putative contingency loci in *Neisseria meningitidis* strain MC58: evidence for a novel mechanism of phase variation," Molecular Microbiology 50(1):245-257.

(Continued)

*Primary Examiner* — Robert A Zeman
(74) *Attorney, Agent, or Firm* — Morrison & Foerster LLP

(57) ABSTRACT

NadA, App and ORF40 function as adhesins in *N. meningitidis*. Adhesion nad be modulated by targeting these three proteins. NadA allelic variants are also disclosed. Autoproteolytic cleavage of App is disclosed, as is removal of the activity by mutagenesis. App is processed and secreted into culture medium when expressed in *E. coli*. Mature App proteins are disclosed. Knockout mutants are disclosed. Vesicles from non-Neisserial hosts with heterologous adhesion expression are disclosed.

7 Claims, 42 Drawing Sheets

(56) References Cited

OTHER PUBLICATIONS

Parkhill, J. et al. (Mar. 2000). "Complete DNA Sequence of a Serogroup A Strain of Neisseria meningitides Z2491," *Nature* 404(6777):502-506.

Pizza et al. (2000). "Identification of Vaccine Candidates Against Serogroup B Meningococcus by Whole-Genome Sequencing," Science 287(5459):1816-1820.

Tettelin et al. (Mar. 10, 2000). "Complete Genome Sequence of Neisseria meningitidis Serogroup B Strain MC58," Science 287(5459):1809-1815.

Tramont, (1976) "Specificity of inhibition of epithelial cell adhesion of Neisseria gonorrhoeae." Infection and Immunity 14:593-595.

Turner et al. (2006). "Characterization of MspA, an Immunogenic Autotransporter Protein That Mediates Adhesion of Epithelial and Endothelial Cells in *Neisseria meningitidis*," Infection and Immunity 74(5):2957-2964.

FIG. 1A
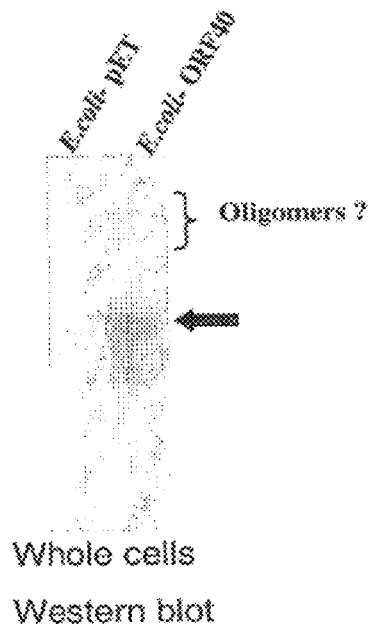
Whole cells
Western blot
FIG. 1B
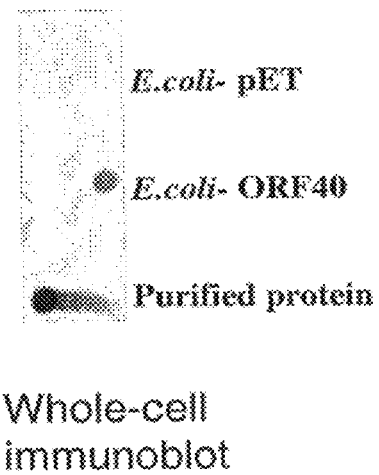
Whole-cell
immunoblot
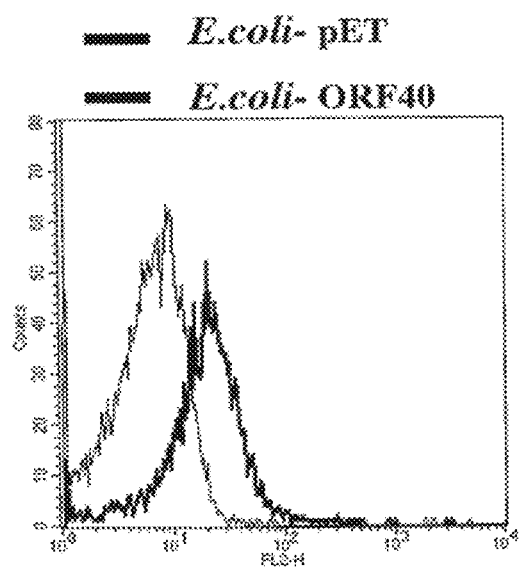
FACS
FIG. 1C

FIG. 2A
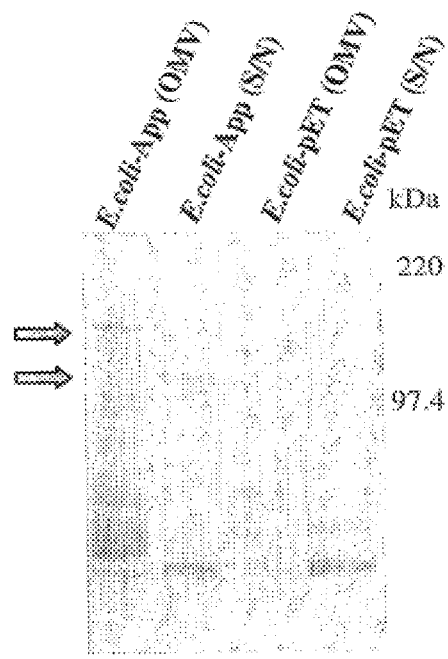
Western blot
FIG. 2B
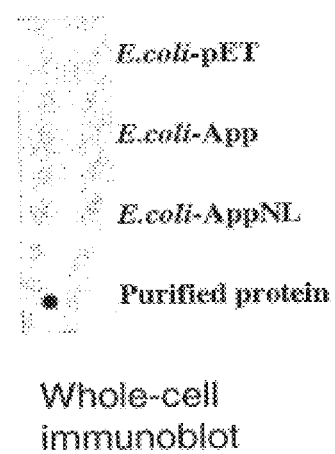
Whole-cell immunoblot
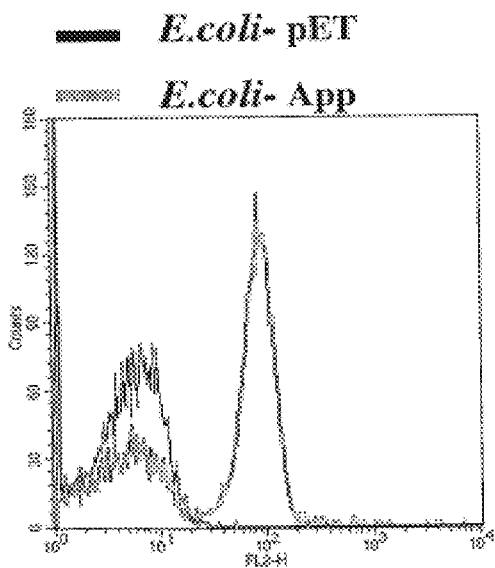
FACS
FIG. 2C

FIG. 3A
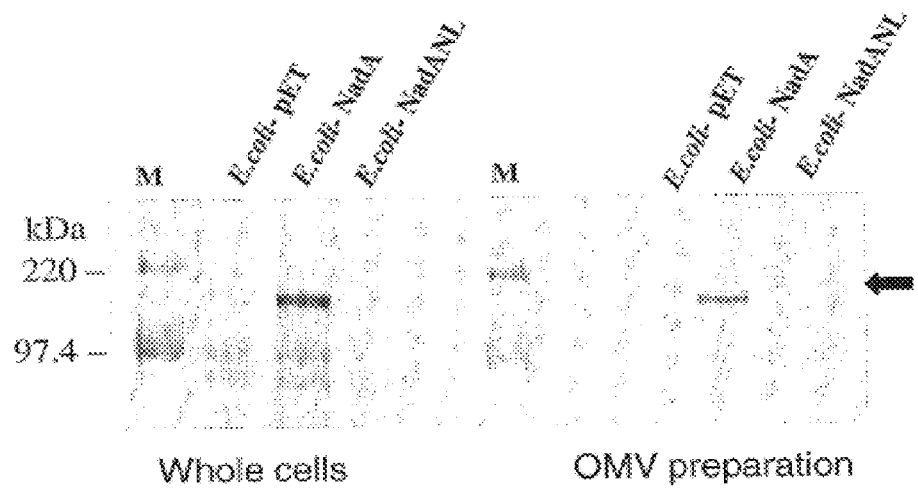
FIG. 3B
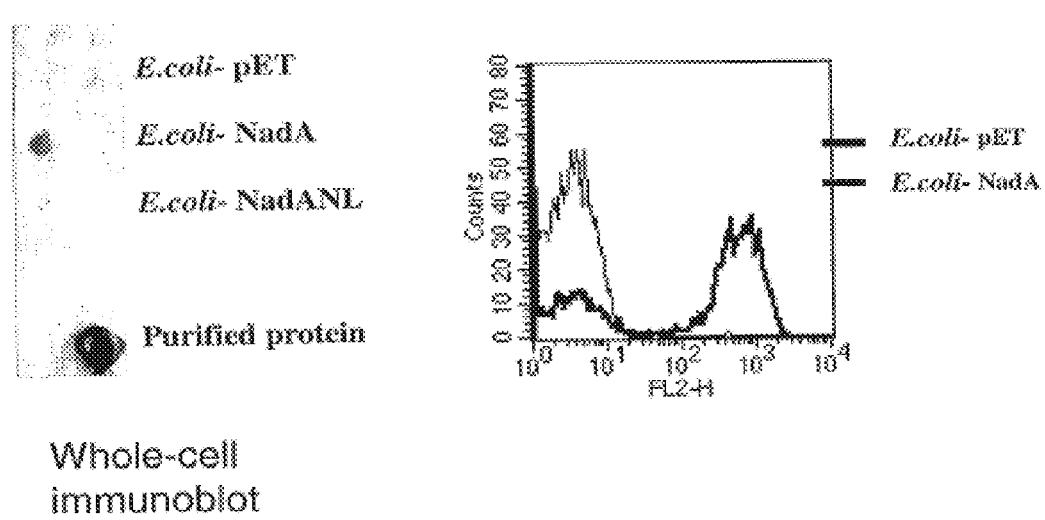
FIG. 3C

FIG. 4A
ORF40
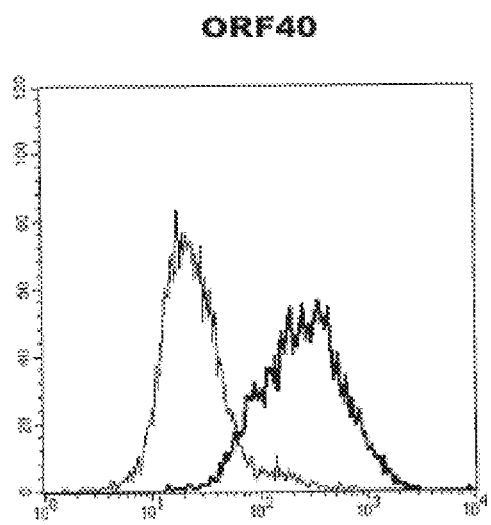
FIG. 4B
App
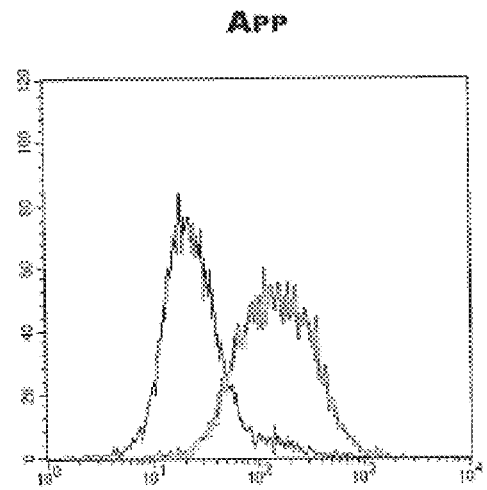
NadA
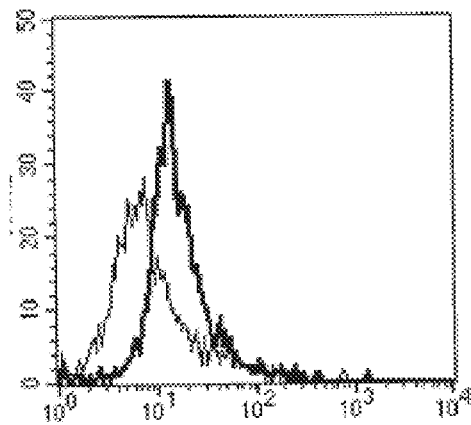
HSF POSITIVE CONTROL
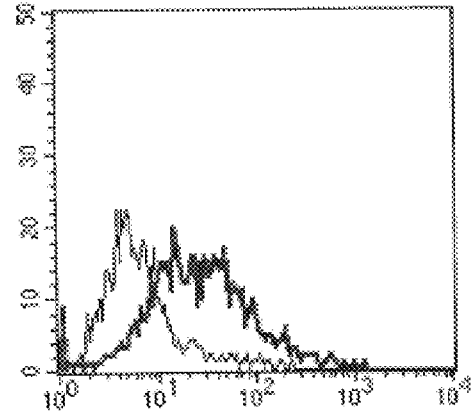
FIG. 4C
FIG. 4D FIG. 5A
ORF40
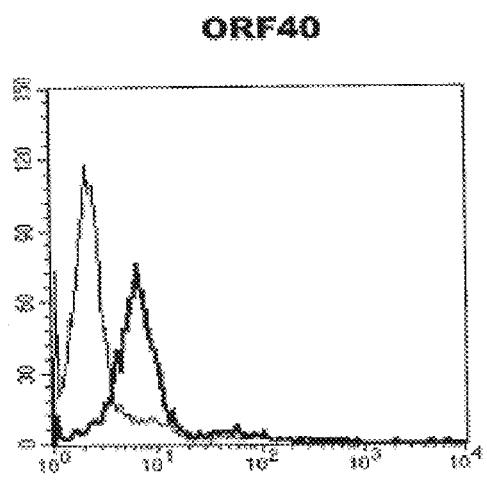
FIG. 5B
App
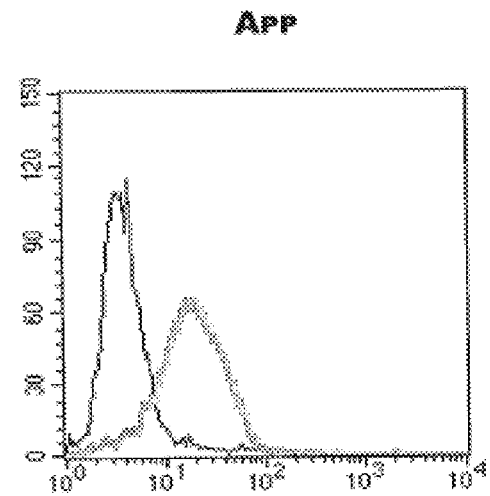
NadA
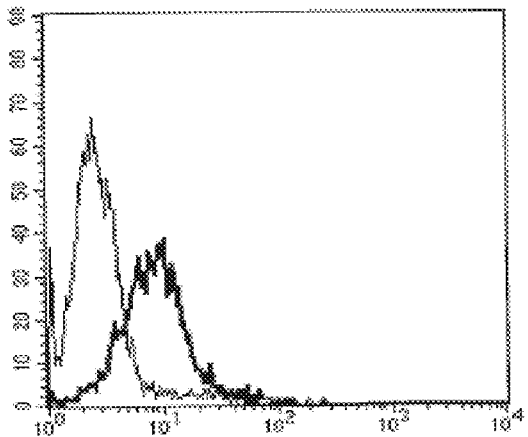
GNA2132 NEGATIVE CONTROL
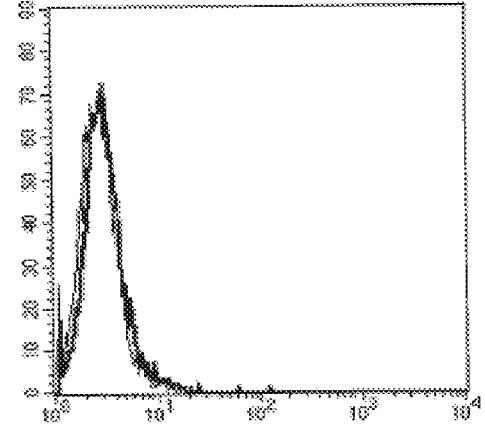
FIG. 5C
FIG. 5D FIG. 6A
FIG. 6B
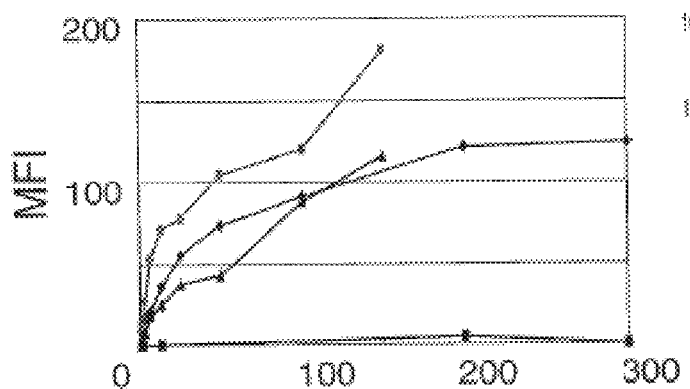
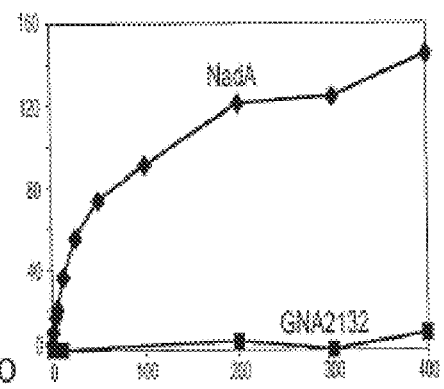

FIG. 9A

| | | |
|---|---|---|
| ALLELE1 | 1: MSMKHFPSKVLTTAILATFCSGALAATDDDVKKAATVAIAAYNNGQEI | :50 |
| ALLELE2 | 1: MSMKHFPSKVLTTAILATFCSGALAATDDDVKKAATVAIAAYNNGQEI | :50 |
| ALLELE3 | 1: MSMKHFPSKVLTTAILATFCSGALAATDDDVKKAATVAIAAYNNGQEI | :50 |
| ALLELE1 | 51: NGPKAGETIYDIDEDGTITKRDATAADVEADDFKGLGLEKVVTNLTKTVN | :100 |
| ALLELE2 | 51: NGPKAGETIYDIDEDGTITKRDATAADVEADDFKGLGLEKVVTNLTKTVN | :100 |
| ALLELE3 | 51: NGPKAGETIYDIDEDGTITKRDATAADVEADDFKGLGLEKVVTNLTKTVN | :100 |
| ALLELE1 | 101: ENKQNVDAKVKAASEIEKLTTRLADTDAALADTDAALDTTNALNKLGE | :150 |
| ALLELE2 | 101: ENKQNVDAKVKAASEIEKLTTR......LADTDAALDTTNALNKLGE | :143 |
| ALLELE3 | 101: ENKQNVDAKVKAASEIEKLTTRLADTDAALADTDAALDTTNALNKLGE | :150 |
| ALLELE1 | 151: NITTFAEETKTNIVKIDEKLEAVADTVDKHAEAFNDIADSLDETNTKADE | :200 |
| ALLELE2 | 144: NITTFAEETKTNIVKIDEKLEAVADTVDKHAEAFNDIADSLDETNTKADE | :193 |
| ALLELE3 | 151: NITTFAEETKTNIVKIDEKLEAVADTVDKHAEAFNDIADSLDETNTKADE | :200 |
| ALLELE1 | 201: AVKTANEAKQTAEETKQNVDAKVKAAETAAGKAEAAAGTANTAADKAEAV | :250 |
| ALLELE2 | 194: AVKTANEAKQTAEETKQNVDAKVKAAETAAGKAEAAAGTANTAADKAEAV | :243 |
| ALLELE3 | 201: AVKTANEAKQTAEETKQNVDAKVKAAETAAGKAEAAAGTANTAADKAEAV | :250 |
| ALLELE1 | 251: AAKVTDIKADIATNKAIAV...KSA............. | :273 |
| ALLELE2 | 244: AAKVTDIKADIATNKDNIAKKANSADVYTEEESDSKPVRIDGLNATTEKI | :293 |
| ALLELE3 | 251: AAKVTDIKADIATNKDNIAKKANSADVYTEEESDSKPVRIDGLNATTEKI | :300 |
| ALLELE1 | 273: ..................SEE.NI..LRRETRQGLAEQAALSGLFQPYI | :307 |
| ALLELE2 | 294: DTRLASAEKSTIHITRLNGLITVSDLRKETRQGLAEQAALSGLFQPYI | :343 |
| ALLELE3 | 301: DTRLASAEKSTIHITRLNGLITVSDLRKETRQGLAEQAALSGLFQPYI | :350 |
| ALLELE1 | 308: VGRFNVTAAVGGYKSESAVAIGTGFRFTENFAAKAGVAVGTSSGSSAAYI | :357 |
| ALLELE2 | 344: VGRFNVTAAVGGYKSESAVAIGTGFRFTENFAAKAGVAVGTSSGSSAAYI | :393 |
| ALLELE3 | 351: VGRFNVTAAVGGYKSESAVAIGTGFRFTENFAAKAGVAVGTSSGSSAAYI | :400 |
| ALLELE1 | 358: VGVNYEF | :364 |
| ALLELE2 | 394: VGVNYEF | :400 |
| ALLELE3 | 401: VGVNYEF | :407 |

FIG. 9B

```
              <------ Leader ------>
ALLELE_3   MKHFPSKVLTTAILATFCSSALAATNDDDVKKAATVAIAAAYNNGQEING    50
ALLELE_2   ................................................
ALLELE_1   ...................S................V...........

<-----------
ALLELE_3   FKAGETIYDIDEDGTITKRDATAADVKADDPKGLGLKKVVTRLTKTVNEN   100
ALLELE_2   ................................................
ALLELE_1   ...........G......Q.............................

---------- coiled coil segment ----------------->
ALLELE_3   KQNVDAKVKAAESEIEKLTTKLADTDAALADTDAALDATTNAINKLGENI   150
ALLELE_2   .....................[          ]...............
ALLELE_1   .................................E..............

<-----------
ALLELE_3   TTPAKEITKINIVKIDEKLEAVADTVDKHAEAFNDIADSLDETNTKADEAV   200
ALLELE_2   ................................................
ALLELE_1   ................................................

---------- coiled coil segment ----------------
ALLELE_3   KTANEAKQTAEETRQNVDAKVKAAETAAGKAEAAAGTANTAADKAEAVAA   250
ALLELE_2   ................................................
ALLELE_1   ................................................

ALLELE_3   KVTDIKADIATNKDSIAKKANSADVYTREESDSKFVRIDGLKATTEKLDT   300
ALLELE_2   ................................................
ALLELE_1   ...........AD..[ ]..[

ALLELE_3   RLASAEKSIADHDTRLNGLDKTVSDLRKETRQGLAEQAALSGLFQPYNVG   350
ALLELE_2   ................TR.G........R...................
ALLELE_1              ].IDS...N.AN........................

<---------- membrane anchor ----------------
ALLELE_3   RFNVTAAVGGYKSESAVAIGTGFRFTENPAAKAGVAVGTSSGSSAAYHVG   400
ALLELE_2   ................................................
ALLELE_1   ................................................

----->
ALLELE_3   VNYEW   405
ALLELE_2   .....
ALLELE_1   .....
```

FIG. 9C

FIG. 15A
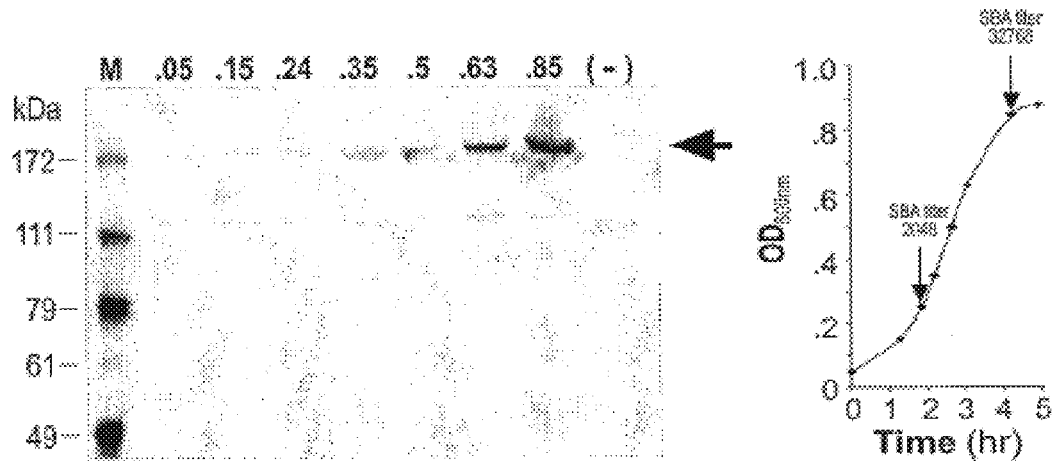
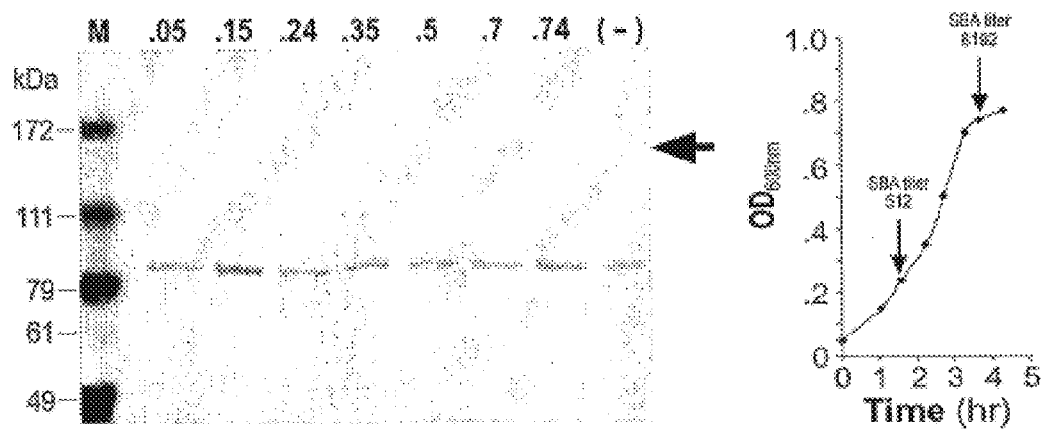
FIG. 15B

FIG. 17A          FIG. 17B
 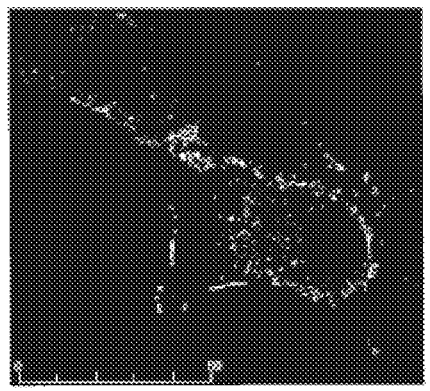
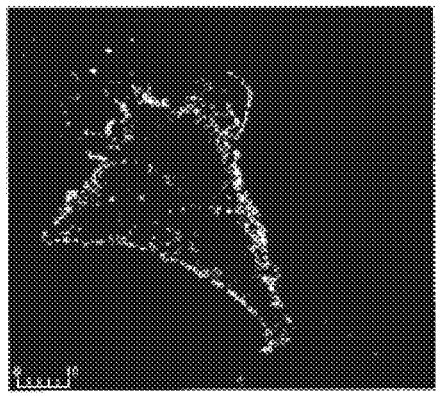 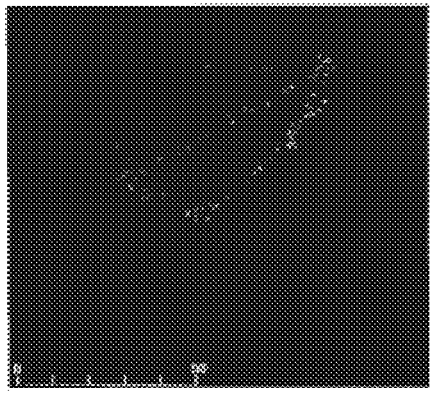
FIG. 17C          FIG. 17D

FIG. 20B    FIG. 20C pET-App pET-App-His pET

SEQUENCE LISTING

<160> NUMBER OF SEQ ID NOS: 57

<210> SEQ ID NO 1
<211> LENGTH: 362
<212> TYPE: PRT
<213> ORGANISM: Neisseria species
<220> FEATURE:
<221> NAME/KEY: MISC_FEATURE
<223> OTHER INFORMATION: allele 1 of NadA

<400> SEQUENCE: 1

```
Met Lys His Phe Pro Ser Lys Val Leu Thr Thr Ala Ile Leu Ala Thr
 1               5                  10                  15

Phe Cys Ser Gly Ala Leu Ala Ala Thr Ser Asp Asp Val Lys Lys
            20                  25                  30

Ala Ala Thr Val Ala Ile Val Ala Ala Tyr Asn Asn Gly Gln Glu Ile
        35                  40                  45

Asn Gly Phe Lys Ala Gly Glu Thr Ile Tyr Asp Ile Gly Glu Asp Gly
    50                  55                  60

Thr Ile Thr Gln Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Glu Thr Thr Asn Ala Leu Asn
    130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
    210                 215                 220

Glu Thr Ala Ala Gly Lys Ala Glu Ala Ala Ala Gly Thr Ala Asn Thr
225                 230                 235                 240

Ala Ala Asp Lys Ala Glu Ala Val Ala Ala Lys Val Thr Asp Ile Lys
                245                 250                 255
```

-continued

Ala Asp Ile Ala Thr Asn Lys Ala Asp Ile Ala Lys Asn Ser Ala Arg
        260                 265                 270

Ile Asp Ser Leu Asp Lys Asn Val Ala Asn Leu Arg Lys Glu Thr Arg
        275                 280                 285

Gln Gly Leu Ala Glu Gln Ala Ala Leu Ser Gly Leu Phe Gln Pro Tyr
        290                 295                 300

Asn Val Gly Arg Phe Asn Val Thr Ala Ala Val Gly Gly Tyr Lys Ser
305                 310                 315                 320

Glu Ser Ala Val Ala Ile Gly Thr Gly Phe Arg Phe Thr Glu Asn Phe
                325                 330                 335

Ala Ala Lys Ala Gly Val Ala Val Gly Thr Ser Ser Gly Ser Ser Ala
                340                 345                 350

Ala Tyr His Val Gly Val Asn Tyr Glu Trp
                355                 360

<210> SEQ ID NO 2
<211> LENGTH: 398
<212> TYPE: PRT
<213> ORGANISM: Neisseria species
<220> FEATURE:
<221> NAME/KEY: MISC_FEATURE
<223> OTHER INFORMATION: allele 2 of NadA

<400> SEQUENCE: 2

Met Lys His Phe Pro Ser Lys Val Leu Thr Thr Ala Ile Leu Ala Thr
  1               5                  10                  15

Phe Cys Ser Gly Ala Leu Ala Ala Thr Asn Asp Asp Val Lys Lys
                 20                  25                  30

Ala Ala Thr Val Ala Ile Ala Ala Tyr Asn Asn Gly Gln Glu Ile
                 35                  40                  45

Asn Gly Phe Lys Ala Gly Glu Thr Ile Tyr Asp Ile Asp Glu Asp Gly
         50                  55                  60

Thr Ile Thr Lys Lys Asp Ala Thr Ala Ala Asp Val Glu Ala Asp Asp
 65                  70                  75                  80

Phe Lys Gly Leu Gly Leu Lys Lys Val Val Thr Asn Leu Thr Lys Thr
                 85                  90                  95

Val Asn Glu Asn Lys Gln Asn Val Asp Ala Lys Val Lys Ala Ala Glu
                100                 105                 110

Ser Glu Ile Glu Lys Leu Thr Thr Lys Leu Ala Asp Thr Asp Ala Ala
                115                 120                 125

Leu Asp Ala Thr Thr Asn Ala Leu Asn Lys Leu Gly Glu Asn Ile Thr
        130                 135                 140

Thr Phe Ala Glu Glu Thr Lys Thr Asn Ile Val Lys Ile Asp Glu Lys
145                 150                 155                 160

Leu Glu Ala Val Ala Asp Thr Val Asp Lys His Ala Glu Ala Phe Asn
                165                 170                 175

Asp Ile Ala Asp Ser Leu Asp Glu Thr Asn Thr Lys Ala Asp Glu Ala
                180                 185                 190

Val Lys Thr Ala Asn Glu Ala Lys Gln Thr Ala Glu Glu Thr Lys Gln
                195                 200                 205

Asn Val Asp Ala Lys Val Lys Ala Ala Glu Thr Ala Ala Gly Lys Ala
        210                 215                 220

Glu Ala Ala Ala Gly Thr Ala Asn Thr Ala Ala Asp Lys Ala Glu Ala
225                 230                 235                 240

Val Ala Ala Lys Val Thr Asp Ile Lys Ala Asp Ile Ala Thr Asn Lys

```
              245                 250                 255
Asp Asn Ile Ala Lys Lys Ala Asn Ser Ala Asp Val Tyr Thr Arg Glu
            260                 265                 270

Glu Ser Asp Ser Lys Phe Val Arg Ile Asp Gly Leu Asn Ala Thr Thr
            275                 280                 285

Glu Lys Leu Asp Thr Arg Leu Ala Ser Ala Glu Lys Ser Ile Thr Glu
            290                 295                 300

His Gly Thr Arg Leu Asn Gly Leu Asp Arg Thr Val Ser Asp Leu Arg
305                 310                 315                 320

Lys Glu Thr Arg Gln Gly Leu Ala Glu Gln Ala Leu Ser Gly Leu
                325                 330                 335

Phe Gln Pro Tyr Asn Val Gly Arg Phe Asn Val Thr Ala Ala Val Gly
                340                 345                 350

Gly Tyr Lys Ser Glu Ser Ala Val Ala Ile Gly Thr Gly Phe Arg Phe
                355                 360                 365

Thr Glu Asn Phe Ala Ala Lys Ala Gly Val Ala Val Gly Thr Ser Ser
            370                 375                 380

Gly Ser Ser Ala Ala Tyr His Val Gly Val Asn Tyr Glu Trp
385                 390                 395

<210> SEQ ID NO 3
<211> LENGTH: 405
<212> TYPE: PRT
<213> ORGANISM: Neisseria species
<220> FEATURE:
<221> NAME/KEY: MISC_FEATURE
<223> OTHER INFORMATION: allele 3 of NadA

<400> SEQUENCE: 3

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
                20                  25                  30

Ala Ala Thr Val Ala Ile Ala Ala Tyr Asn Asn Gly Gln Glu Ile
            35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
    130                 135                 140

Lys Leu Gly Glu Asn Ile Thr Thr Phe Ala Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205
```

```
Thr Ala Glu Glu Thr Lys Gln Asn Val Asp Ala Lys Val Lys Ala Ala
    210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Arg Phe
            340                 345                 350

Asn Val Thr Ala Ala Val Gly Gly Tyr Lys Ser Glu Ser Ala Val Ala
            355                 360                 365

Ile Gly Thr Gly Phe Arg Phe Thr Glu Asn Phe Ala Ala Lys Ala Gly
        370                 375                 380

Val Ala Val Gly Thr Ser Ser Gly Ser Ser Ala Ala Tyr His Val Gly
385                 390                 395                 400

Val Asn Tyr Glu Trp
                405

<210> SEQ ID NO 4
<211> LENGTH: 364
<212> TYPE: PRT
<213> ORGANISM: Neisseria species
<220> FEATURE:
<221> NAME/KEY: MISC_FEATURE
<223> OTHER INFORMATION: allele 1 of NadA (first-ATG start)

<400> SEQUENCE: 4

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
            20                  25                  30

Lys Lys Ala Ala Thr Val Ala Ile Val Ala Ala Tyr Asn Asn Gly Gln
        35                  40                  45

Glu Ile Asn Gly Phe Lys Ala Gly Glu Thr Ile Tyr Asp Ile Gly Glu
    50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140

Leu Asn Lys Leu Gly Glu Asn Ile Thr Thr Phe Ala Glu Glu Thr Lys
145                 150                 155                 160
```

-continued

```
Thr Asn Ile Val Lys Ile Asp Glu Lys Leu Glu Ala Val Ala Asp Thr
                165                 170                 175
Val Asp Lys His Ala Glu Ala Phe Asn Asp Ile Ala Asp Ser Leu Asp
                180                 185                 190
Glu Thr Asn Thr Lys Ala Asp Glu Ala Val Lys Thr Ala Asn Glu Ala
                195                 200                 205
Lys Gln Thr Ala Glu Glu Thr Lys Gln Asn Val Asp Ala Lys Val Lys
                210                 215                 220
Ala Ala Glu Thr Ala Ala Gly Lys Ala Glu Ala Ala Ala Gly Thr Ala
225                 230                 235                 240
Asn Thr Ala Ala Asp Lys Ala Glu Ala Val Ala Ala Lys Val Thr Asp
                245                 250                 255
Ile Lys Ala Asp Ile Ala Thr Asn Lys Ala Asp Ile Ala Lys Asn Ser
                260                 265                 270
Ala Arg Ile Asp Ser Leu Asp Lys Asn Val Ala Asn Leu Arg Lys Glu
                275                 280                 285
Thr Arg Gln Gly Leu Ala Glu Gln Ala Ala Leu Ser Gly Leu Phe Gln
                290                 295                 300
Pro Tyr Asn Val Gly Arg Phe Asn Val Thr Ala Ala Val Gly Gly Tyr
305                 310                 315                 320
Lys Ser Glu Ser Ala Val Ala Ile Gly Thr Gly Phe Arg Phe Thr Glu
                325                 330                 335
Asn Phe Ala Ala Lys Ala Gly Val Ala Val Gly Thr Ser Ser Gly Ser
                340                 345                 350
Ser Ala Ala Tyr His Val Gly Val Asn Tyr Glu Trp
                355                 360

<210> SEQ ID NO 5
<211> LENGTH: 400
<212> TYPE: PRT
<213> ORGANISM: Neisseria species
<220> FEATURE:
<221> NAME/KEY: MISC_FEATURE
<223> OTHER INFORMATION: allele 2 of NadA (first-ATG start)

<400> SEQUENCE: 5

Met Ser Met Lys His Phe Pro Ser Lys Val Leu Thr Thr Ala Ile Leu
1               5                   10                  15
Ala Thr Phe Cys Ser Gly Ala Leu Ala Ala Thr Asn Asp Asp Asp Val
                20                  25                  30
Lys Lys Ala Ala Thr Val Ala Ile Ala Ala Ala Tyr Asn Asn Gly Gln
                35                  40                  45
Glu Ile Asn Gly Phe Lys Ala Gly Glu Thr Ile Tyr Asp Ile Asp Glu
                50                  55                  60
Asp Gly Thr Ile Thr Lys Lys Asp Ala Thr Ala Ala Asp Val Glu Ala
65                  70                  75                  80
Asp Asp Phe Lys Gly Leu Gly Leu Lys Lys Val Val Thr Asn Leu Thr
                85                  90                  95
Lys Thr Val Asn Glu Asn Lys Gln Asn Val Asp Ala Lys Val Lys Ala
                100                 105                 110
Ala Glu Ser Glu Ile Glu Lys Leu Thr Thr Lys Leu Ala Asp Thr Asp
                115                 120                 125
Ala Ala Leu Asp Ala Thr Thr Asn Ala Leu Asn Lys Leu Gly Glu Asn
                130                 135                 140
Ile Thr Thr Phe Ala Glu Glu Thr Lys Thr Asn Ile Val Lys Ile Asp
```

```
        145                 150                 155                 160
    Glu Lys Leu Glu Ala Val Ala Asp Thr Val Asp Lys His Ala Glu Ala
                    165                 170                 175

Phe Asn Asp Ile Ala Asp Ser Leu Asp Glu Thr Asn Thr Lys Ala Asp
                    180                 185                 190

Glu Ala Val Lys Thr Ala Asn Glu Ala Lys Gln Thr Ala Glu Glu Thr
                    195                 200                 205

Lys Gln Asn Val Asp Ala Lys Val Lys Ala Ala Glu Thr Ala Ala Gly
        210                 215                 220

Lys Ala Glu Ala Ala Ala Gly Thr Ala Asn Thr Ala Ala Asp Lys Ala
    225                 230                 235                 240

Glu Ala Val Ala Ala Lys Val Thr Asp Ile Lys Ala Asp Ile Ala Thr
                    245                 250                 255

Asn Lys Asp Asn Ile Ala Lys Lys Ala Asn Ser Ala Asp Val Tyr Thr
                    260                 265                 270

Arg Glu Glu Ser Asp Ser Lys Phe Val Arg Ile Asp Gly Leu Asn Ala
                    275                 280                 285

Thr Thr Glu Lys Leu Asp Thr Arg Leu Ala Ser Ala Glu Lys Ser Ile
        290                 295                 300

Thr Glu His Gly Thr Arg Leu Asn Gly Leu Asp Arg Thr Val Ser Asp
    305                 310                 315                 320

Leu Arg Lys Glu Thr Arg Gln Gly Leu Ala Glu Gln Ala Ala Leu Ser
                    325                 330                 335

Gly Leu Phe Gln Pro Tyr Asn Val Gly Arg Phe Asn Val Thr Ala Ala
                    340                 345                 350

Val Gly Gly Tyr Lys Ser Glu Ser Ala Val Ala Ile Gly Thr Gly Phe
                    355                 360                 365

Arg Phe Thr Glu Asn Phe Ala Ala Lys Ala Gly Val Ala Val Gly Thr
                    370                 375                 380

Ser Ser Gly Ser Ser Ala Ala Tyr His Val Gly Val Asn Tyr Glu Trp
    385                 390                 395                 400

<210> SEQ ID NO 6
<211> LENGTH: 407
<212> TYPE: PRT
<213> ORGANISM: Neisseria species
<220> FEATURE:
<221> NAME/KEY: MISC_FEATURE
<223> OTHER INFORMATION: allele 3 of NadA (first-ATG start)

<400> SEQUENCE: 6

Met Ser Met Lys His Phe Pro Ser Lys Val Leu Thr Thr Ala Ile Leu
 1               5                  10                  15

Ala Thr Phe Cys Ser Gly Ala Leu Ala Ala Thr Asn Asp Asp Asp Val
                20                  25                  30

Lys Lys Ala Ala Thr Val Ala Ile Ala Ala Ala Tyr Asn Asn Gly Gln
            35                  40                  45

Glu Ile Asn Gly Phe Lys Ala Gly Glu Thr Ile Tyr Asp Ile Asp Glu
        50                  55                  60

Asp Gly Thr Ile Thr Lys Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
                100                 105                 110
```

Ala Glu Ser Glu Ile Glu Lys Leu Thr Thr Lys Leu Ala Asp Thr Asp
            115                 120                 125

Ala Ala Leu Ala Asp Thr Asp Ala Ala Leu Asp Ala Thr Thr Asn Ala
130                 135                 140

Leu Asn Lys Leu Gly Glu Asn Ile Thr Thr Phe Ala Glu Thr Lys
145                 150                 155                 160

Thr Asn Ile Val Lys Ile Asp Glu Lys Leu Glu Ala Val Ala Asp Thr
            165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
            195                 200                 205

Lys Gln Thr Ala Glu Glu Thr Lys Gln Asn Val Asp Ala Lys Val Lys
210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Ala Lys Val Thr Asp
            245                 250                 255

Ile Lys Ala Asp Ile Ala Thr Asn Lys Asp Asn Ile Ala Lys Lys Ala
            260                 265                 270

Asn Ser Ala Asp Val Tyr Thr Arg Glu Glu Ser Asp Ser Lys Phe Val
275                 280                 285

Arg Ile Asp Gly Leu Asn Ala Thr Thr Glu Lys Leu Asp Thr Arg Leu
            290                 295                 300

Ala Ser Ala Glu Lys Ser Ile Ala Asp His Asp Thr Arg Leu Asn Gly
305                 310                 315                 320

Leu Asp Lys Thr Val Ser Asp Leu Arg Lys Glu Thr Arg Gln Gly Leu
            325                 330                 335

Ala Glu Gln Ala Ala Leu Ser Gly Leu Phe Gln Pro Tyr Asn Val Gly
            340                 345                 350

Arg Phe Asn Val Thr Ala Ala Val Gly Gly Tyr Lys Ser Glu Ser Ala
            355                 360                 365

Val Ala Ile Gly Thr Gly Phe Arg Phe Thr Glu Asn Phe Ala Ala Lys
            370                 375                 380

Ala Gly Val Ala Val Gly Thr Ser Ser Gly Ser Ser Ala Ala Tyr His
385                 390                 395                 400

Val Gly Val Asn Tyr Glu Trp
            405

<210> SEQ ID NO 7
<211> LENGTH: 391
<212> TYPE: PRT
<213> ORGANISM: Neisseria species
<220> FEATURE:
<221> NAME/KEY: MISC_FEATURE
<223> OTHER INFORMATION: variant allele 2 of NadA in strain 1881024

<400> SEQUENCE: 7

Met Lys His Phe Pro Ser Lys Val Leu Thr Thr Ala Ile Leu Ala Thr
1               5                   10                  15

Phe Cys Ser Gly Ala Leu Ala Thr Asn Asp Asp Val Lys Lys
            20                  25                  30

Ala Ala Thr Val Ala Ile Ala Ala Ala Tyr Asn Asn Gly Gln Glu Ile
            35                  40                  45

Asn Gly Phe Lys Ala Gly Glu Thr Ile Tyr Asp Ile Asp Glu Asp Gly
50                  55                  60

Thr Ile Thr Lys Lys Asp Ala Thr Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
                100                 105                 110

Ser Glu Ile Glu Lys Leu Thr Thr Lys Leu Ala Asp Thr Asp Ala Ala
            115                 120                 125

Leu Asp Ala Thr Thr Asn Ala Leu Asn Lys Leu Gly Glu Asn Ile Thr
            130                 135                 140

Thr Phe Ala Glu Glu Thr Lys Thr Asn Ile Val Lys Ile Asp Glu Lys
145                 150                 155                 160

Leu Glu Ala Val Ala Asp Thr Val Asp Lys His Ala Glu Ala Phe Asn
                165                 170                 175

Asp Ile Ala Asp Ser Leu Asp Glu Thr Asn Thr Lys Ala Asp Glu Ala
                180                 185                 190

Val Lys Thr Ala Asn Glu Ala Lys Gln Thr Ala Glu Glu Thr Lys Gln
            195                 200                 205

Asn Val Asp Ala Lys Val Lys Ala Ala Glu Thr Ala Ala Gly Thr Ala
210                 215                 220

Asn Thr Ala Ala Asp Lys Ala Glu Ala Val Ala Ala Lys Val Thr Asp
225                 230                 235                 240

Ile Lys Ala Asp Ile Ala Thr Asn Lys Asp Ile Asp Ala Lys Lys Ala
                245                 250                 255

Asn Ser Ala Asp Val Tyr Thr Arg Glu Ser Asp Ser Lys Phe Val
            260                 265                 270

Arg Ile Asp Gly Leu Asn Ala Thr Thr Glu Lys Leu Asp Thr Arg Leu
            275                 280                 285

Ala Ser Ala Glu Lys Ser Ile Thr Glu His Gly Thr Arg Leu Asn Gly
290                 295                 300

Leu Asp Arg Thr Val Ser Asp Leu Arg Lys Glu Thr Arg Gln Gly Leu
305                 310                 315                 320

Ala Glu Gln Ala Ala Leu Ser Gly Leu Phe Gln Pro Tyr Asn Val Gly
                325                 330                 335

Arg Phe Asn Val Thr Ala Ala Val Gly Gly Tyr Lys Ser Glu Ser Ala
                340                 345                 350

Val Ala Ile Gly Thr Gly Phe Arg Phe Thr Glu Asn Phe Ala Ala Lys
            355                 360                 365

Ala Gly Val Ala Val Gly Thr Ser Ser Gly Ser Ser Ala Ala Tyr His
            370                 375                 380

Val Gly Val Asn Tyr Glu Trp
385                 390

<210> SEQ ID NO 8
<211> LENGTH: 393
<212> TYPE: PRT
<213> ORGANISM: Neisseria species
<220> FEATURE:
<221> NAME/KEY: MISC_FEATURE
<223> OTHER INFORMATION: variant allele 2 of NadA (first-ATG start) in
      strain 1881024

<400> SEQUENCE: 8

Met Ser Met Lys His Phe Pro Ser Lys Val Leu Thr Thr Ala Ile Leu
1               5                   10                  15

```
Ala Thr Phe Cys Ser Gly Ala Leu Ala Ala Thr Asn Asp Asp Val
             20                  25                  30

Lys Lys Ala Ala Thr Val Ala Ile Ala Ala Tyr Asn Asn Gly Gln
 35                  40                  45

Glu Ile Asn Gly Phe Lys Ala Gly Glu Thr Ile Tyr Asp Ile Asp Glu
 50                  55                  60

Asp Gly Thr Ile Thr Lys Lys Asp Ala Thr Ala Ala Asp Val Glu Ala
 65                  70                  75                  80

Asp Asp Phe Lys Gly Leu Gly Leu Lys Lys Val Val Thr Asn Leu Thr
                 85                  90                  95

Lys Thr Val Asn Glu Asn Lys Gln Asn Val Asp Ala Lys Val Lys Ala
                100                 105                 110

Ala Glu Ser Glu Ile Glu Lys Leu Thr Thr Lys Leu Ala Asp Thr Asp
            115                 120                 125

Ala Ala Leu Asp Ala Thr Thr Asn Ala Leu Asn Lys Leu Gly Glu Asn
        130                 135                 140

Ile Thr Thr Phe Ala Glu Glu Thr Lys Thr Asn Ile Val Lys Ile Asp
145                 150                 155                 160

Glu Lys Leu Glu Ala Val Ala Asp Thr Val Asp Lys His Ala Glu Ala
                165                 170                 175

Phe Asn Asp Ile Ala Asp Ser Leu Asp Glu Thr Asn Thr Lys Ala Asp
            180                 185                 190

Glu Ala Val Lys Thr Ala Asn Glu Ala Lys Gln Thr Ala Glu Glu Thr
        195                 200                 205

Lys Gln Asn Val Asp Ala Lys Val Lys Ala Ala Glu Thr Ala Ala Gly
210                 215                 220

Thr Ala Asn Thr Ala Ala Asp Lys Ala Glu Ala Val Ala Ala Lys Val
225                 230                 235                 240

Thr Asp Ile Lys Ala Asp Ile Ala Thr Asn Lys Asp Asn Ile Ala Lys
                245                 250                 255

Lys Ala Asn Ser Ala Asp Val Tyr Thr Arg Glu Glu Ser Asp Ser Lys
            260                 265                 270

Phe Val Arg Ile Asp Gly Leu Asn Ala Thr Thr Glu Lys Leu Asp Thr
        275                 280                 285

Arg Leu Ala Ser Ala Glu Lys Ser Ile Thr Glu His Gly Thr Arg Leu
290                 295                 300

Asn Gly Leu Asp Arg Thr Val Ser Asp Leu Arg Lys Glu Thr Arg Gln
305                 310                 315                 320

Gly Leu Ala Glu Gln Ala Ala Leu Ser Gly Leu Phe Gln Pro Tyr Asn
                325                 330                 335

Val Gly Arg Phe Asn Val Thr Ala Ala Val Gly Gly Tyr Lys Ser Glu
            340                 345                 350

Ser Ala Val Ala Ile Gly Thr Gly Phe Arg Phe Thr Glu Asn Phe Ala
        355                 360                 365

Ala Lys Ala Gly Val Ala Val Gly Thr Ser Ser Gly Ser Ser Ala Ala
370                 375                 380

Tyr His Val Gly Val Asn Tyr Glu Trp
385                 390
```

<210> SEQ ID NO 9
<211> LENGTH: 404
<212> TYPE: PRT
<213> ORGANISM: Neisseria species
<220> FEATURE:
<221> NAME/KEY: MISC_FEATURE
<223> OTHER INFORMATION: variant allele 3 of NadA in strains 973-1720 and 188759

<400> SEQUENCE: 9

```
Met Gln His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Met Tyr Asn Asn Gly Gln Glu Ile Asn
            35                  40                  45

Gly Phe Lys Ala Gly Glu Thr Ile Tyr Asp Ile Asp Glu Asp Gly Thr
    50                  55                  60

Ile Thr Lys Lys Asp Ala Thr Ala Ala Asp Val Glu Ala Asp Asp Phe
65                  70                  75                  80

Lys Gly Leu Gly Leu Lys Lys Val Val Thr Asn Leu Thr Lys Thr Val
                85                  90                  95

Asn Glu Asn Lys Gln Asn Val Asp Ala Lys Val Lys Ala Ala Glu Ser
                100                 105                 110

Glu Ile Glu Lys Leu Thr Thr Lys Leu Ala Asp Thr Asp Ala Ala Leu
            115                 120                 125

Ala Asp Thr Asp Ala Ala Leu Asp Ala Thr Thr Asn Ala Leu Asn Lys
        130                 135                 140

Leu Gly Glu Asn Ile Thr Thr Phe Ala Glu Thr Lys Thr Asn Ile
145                 150                 155                 160

Val Lys Ile Asp Glu Lys Leu Glu Ala Val Ala Asp Thr Val Asp Lys
                165                 170                 175

His Ala Glu Ala Phe Asn Asp Ile Ala Asp Ser Leu Asp Glu Thr Asn
            180                 185                 190

Thr Lys Ala Asp Glu Ala Val Lys Thr Ala Asn Glu Ala Lys Gln Thr
        195                 200                 205

Ala Glu Glu Thr Lys Gln Asn Val Asp Ala Lys Val Lys Ala Ala Glu
    210                 215                 220

Thr Ala Ala Gly Lys Ala Glu Ala Ala Gly Thr Ala Asn Thr Ala
225                 230                 235                 240

Ala Asp Lys Ala Glu Ala Val Ala Ala Lys Val Thr Asp Ile Lys Ala
                245                 250                 255

Asp Ile Ala Thr Asn Lys Asp Asn Ile Ala Lys Lys Ala Asn Ser Ala
            260                 265                 270

Asp Val Tyr Thr Arg Glu Glu Ser Asp Ser Lys Phe Val Arg Ile Asp
        275                 280                 285

Gly Leu Asn Ala Thr Thr Glu Lys Leu Asp Thr Arg Leu Ala Ser Ala
    290                 295                 300

Glu Lys Ser Ile Ala Asp His Asp Thr Arg Leu Asn Gly Leu Asp Lys
305                 310                 315                 320

Thr Val Ser Asp Leu Arg Lys Glu Thr Arg Gln Gly Leu Ala Glu Gln
                325                 330                 335

Ala Ala Leu Ser Gly Leu Phe Gln Pro Tyr Asn Val Gly Arg Phe Asn
            340                 345                 350

Val Thr Ala Ala Val Gly Gly Tyr Lys Ser Glu Ser Ala Val Ala Ile
        355                 360                 365

Gly Thr Gly Phe Arg Phe Thr Glu Asn Phe Ala Ala Lys Ala Gly Val
    370                 375                 380

Ala Val Gly Thr Ser Ser Gly Ser Ser Ala Ala Tyr His Val Gly Val
385                 390                 395                 400
```

Asn Tyr Glu Trp

<210> SEQ ID NO 10
<211> LENGTH: 407
<212> TYPE: PRT
<213> ORGANISM: Neisseria species
<220> FEATURE:
<221> NAME/KEY: MISC_FEATURE
<223> OTHER INFORMATION: variant allele 3 of NadA (first-ATG start) in
      strains 973-1720 and 188759

<400> SEQUENCE: 10

Met Ser Met Gln His Phe Pro Ser Lys Val Leu Thr Thr Ala Ile Leu
 1               5                  10                  15

Ala Thr Phe Cys Ser Gly Ala Leu Ala Ala Thr Asn Asp Asp Asp Val
            20                  25                  30

Lys Lys Ala Ala Thr Val Ala Ile Ala Ala Tyr Asn Asn Gly Gln
         35                  40                  45

Glu Ile Asn Gly Phe Lys Ala Gly Glu Thr Ile Tyr Asp Ile Asp Glu
 50                  55                  60

Asp Gly Thr Ile Thr Lys Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Ala Thr Thr Asn Ala
130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Asp Asn Ile Ala Lys Lys Ala
            260                 265                 270

Asn Ser Ala Asp Val Tyr Thr Arg Glu Glu Ser Asp Ser Lys Phe Val
        275                 280                 285

Arg Ile Asp Gly Leu Asn Ala Thr Thr Glu Lys Leu Asp Thr Arg Leu
    290                 295                 300

Ala Ser Ala Glu Lys Ser Ile Ala Asp His Asp Thr Arg Leu Asn Gly
305                 310                 315                 320

Leu Asp Lys Thr Val Ser Asp Leu Arg Lys Glu Thr Arg Gln Gly Leu
                325                 330                 335

Ala Glu Gln Ala Ala Leu Ser Gly Leu Phe Gln Pro Tyr Asn Val Gly

```
            340                 345                 350
Arg Phe Asn Val Thr Ala Ala Val Gly Gly Tyr Lys Ser Glu Ser Ala
            355                 360                 365

Val Ala Ile Gly Thr Gly Phe Arg Phe Thr Glu Asn Phe Ala Ala Lys
        370                 375                 380

Ala Gly Val Ala Val Gly Thr Ser Ser Gly Ser Ser Ala Ala Tyr His
385                 390                 395                 400

Val Gly Val Asn Tyr Glu Trp
                405

<210> SEQ ID NO 11
<211> LENGTH: 355
<212> TYPE: PRT
<213> ORGANISM: Neisseria species
<220> FEATURE:
<221> NAME/KEY: MISC_FEATURE
<223> OTHER INFORMATION: NadA allele 1/2 chimera (strain 95330)

<400> SEQUENCE: 11

Met Lys His Phe Pro Ser Lys Val Leu Thr Thr Ala Ile Leu Ala Thr
 1               5                  10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Asp Ala Thr Thr Asn Ala Leu Asn Lys Leu Gly Glu Asn Ile Thr
    130                 135                 140

Thr Phe Ala Glu Glu Thr Lys Thr Asn Ile Val Lys Ile Asp Glu Lys
145                 150                 155                 160

Leu Glu Ala Val Ala Asp Thr Val Asp Lys His Ala Glu Ala Phe Asn
                165                 170                 175

Asp Ile Ala Asp Ser Leu Asp Glu Thr Asn Thr Lys Ala Asp Glu Ala
            180                 185                 190

Val Lys Thr Ala Asn Glu Ala Lys Gln Thr Ala Glu Glu Thr Lys Gln
        195                 200                 205

Asn Val Asp Ala Lys Val Lys Ala Ala Glu Thr Ala Ala Gly Lys Ala
    210                 215                 220

Glu Ala Ala Ala Gly Thr Ala Asn Thr Ala Ala Asp Lys Ala Glu Ala
225                 230                 235                 240

Val Ala Ala Lys Val Thr Asp Ile Lys Ala Asp Ile Ala Thr Asn Lys
                245                 250                 255

Ala Asp Ile Ala Lys Asn Ser Ala Arg Ile Asp Ser Leu Asp Lys Asn
            260                 265                 270

Val Ala Asn Leu Arg Lys Glu Thr Arg Gln Gly Leu Ala Glu Gln Ala
        275                 280                 285
```

```
Ala Leu Ser Gly Leu Phe Gln Pro Tyr Asn Val Gly Arg Phe Asn Val
    290                 295                 300

Thr Ala Ala Val Gly Gly Tyr Lys Ser Glu Ser Ala Val Ala Ile Gly
305                 310                 315                 320

Thr Gly Phe Arg Phe Thr Glu Asn Phe Ala Ala Lys Ala Gly Val Ala
                325                 330                 335

Val Gly Thr Ser Ser Gly Ser Ser Ala Ala Tyr His Val Gly Val Asn
            340                 345                 350

Tyr Glu Trp
        355

<210> SEQ ID NO 12
<211> LENGTH: 357
<212> TYPE: PRT
<213> ORGANISM: Neisseria species
<220> FEATURE:
<221> NAME/KEY: MISC_FEATURE
<223> OTHER INFORMATION: NadA allele 1/2 chimera (strain 95330)
      (first-ATG start)

<400> SEQUENCE: 12

Met Ser Met Lys His Phe Pro Ser Lys Val Leu Thr Thr Ala Ile Leu
1               5                   10                  15

Ala Thr Phe Cys Ser Gly Ala Leu Ala Ala Thr Asn Asp Asp Asp Val
            20                  25                  30

Lys Lys Ala Ala Thr Val Ala Ile Ala Ala Tyr Asn Asn Gly Gln
        35                  40                  45

Glu Ile Asn Gly Phe Lys Ala Gly Glu Thr Ile Tyr Asp Ile Asp Glu
50                  55                  60

Asp Gly Thr Ile Thr Lys Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Asp Ala Thr Thr Asn Ala Leu Asn Lys Leu Gly Glu Asn
130                 135                 140

Ile Thr Thr Phe Ala Glu Glu Thr Lys Thr Asn Ile Val Lys Ile Asp
145                 150                 155                 160

Glu Lys Leu Glu Ala Val Ala Asp Thr Val Asp Lys His Ala Glu Ala
                165                 170                 175

Phe Asn Asp Ile Ala Asp Ser Leu Asp Glu Thr Asn Thr Lys Ala Asp
            180                 185                 190

Glu Ala Val Lys Thr Ala Asn Glu Ala Lys Gln Thr Ala Glu Glu Thr
        195                 200                 205

Lys Gln Asn Val Asp Ala Lys Val Lys Ala Ala Glu Thr Ala Ala Gly
210                 215                 220

Lys Ala Glu Ala Ala Ala Gly Thr Ala Asn Thr Ala Ala Asp Lys Ala
225                 230                 235                 240

Glu Ala Val Ala Ala Lys Val Thr Asp Ile Lys Ala Asp Ile Ala Thr
                245                 250                 255

Asn Lys Ala Asp Ile Ala Lys Asn Ser Ala Arg Ile Asp Ser Leu Asp
            260                 265                 270

Lys Asn Val Ala Asn Leu Arg Lys Glu Thr Arg Gln Gly Leu Ala Glu
```

```
            275                 280                 285
Gln Ala Ala Leu Ser Gly Leu Phe Gln Pro Tyr Asn Val Gly Arg Phe
        290                 295                 300

Asn Val Thr Ala Ala Val Gly Gly Tyr Lys Ser Glu Ser Ala Val Ala
305                 310                 315                 320

Ile Gly Thr Gly Phe Arg Phe Thr Glu Asn Phe Ala Ala Lys Ala Gly
                325                 330                 335

Val Ala Val Gly Thr Ser Ser Gly Ser Ser Ala Ala Tyr His Val Gly
            340                 345                 350

Val Asn Tyr Glu Trp
            355

<210> SEQ ID NO 13
<211> LENGTH: 323
<212> TYPE: PRT
<213> ORGANISM: Neisseria species
<220> FEATURE:
<221> NAME/KEY: MISC_FEATURE
<223> OTHER INFORMATION: NadA allele C

<400> SEQUENCE: 13

Met Lys His Phe Pro Ser Lys Val Leu Thr Ala Ala Ile Leu Ala Ala
1               5                   10                  15

Leu Ser Gly Ser Ala Met Ala Asp Asn Ala Pro Thr Ala Asp Glu Ile
            20                  25                  30

Ala Lys Ala Ala Leu Val Asn Ser Tyr Asn Asn Thr Gln Asp Ile Asn
        35                  40                  45

Gly Phe Thr Val Gly Asp Thr Ile Tyr Asp Ile Lys Asn Asp Lys Ile
    50                  55                  60

Thr Lys Lys Glu Ala Thr Glu Ala Asp Val Glu Ala Asp Asp Phe Lys
65                  70                  75                  80

Gly Leu Gly Leu Lys Glu Val Val Ala Gln His Asp Gln Ser Leu Ala
                85                  90                  95

Asp Leu Thr Glu Thr Val Asn Glu Asn Ser Glu Ala Leu Val Lys Thr
            100                 105                 110

Ala Ala Val Val Asn Asp Ile Ser Ala Asp Val Lys Ala Asn Thr Ala
        115                 120                 125

Ala Ile Gly Glu Asn Lys Ala Ala Ile Ala Thr Lys Ala Asp Lys Thr
    130                 135                 140

Glu Leu Asp Lys Val Ser Gly Lys Val Thr Glu Asn Glu Thr Ala Ile
145                 150                 155                 160

Gly Lys Lys Ala Asn Ser Ala Asp Val Tyr Thr Lys Ala Glu Val Tyr
                165                 170                 175

Thr Lys Gln Glu Ser Asp Asn Arg Phe Val Lys Ile Ser Asp Gly Ile
            180                 185                 190

Gly Asn Leu Asn Thr Thr Ala Asn Gly Leu Glu Thr Arg Leu Ala Ala
        195                 200                 205

Ala Glu Gln Ser Val Ala Asp His Gly Thr Arg Leu Ala Ser Ala Glu
    210                 215                 220

Lys Ser Ile Thr Glu His Gly Thr Arg Leu Asn Gly Leu Asp Arg Thr
225                 230                 235                 240

Val Ser Asp Leu Arg Lys Glu Thr Arg Gln Gly Leu Ala Glu Gln Ala
                245                 250                 255

Ala Leu Ser Gly Leu Phe Gln Pro Tyr Asn Val Gly Arg Phe Asn Val
            260                 265                 270
```

Thr Ala Ala Val Gly Gly Tyr Lys Ser Glu Ser Ala Val Ala Ile Gly
            275                 280                 285

Thr Gly Phe Arg Phe Thr Glu Asn Phe Ala Ala Lys Ala Gly Val Ala
290                 295                 300

Val Gly Thr Ser Ser Gly Ser Ser Ala Ala Tyr His Val Gly Val Asn
305                 310                 315                 320

Tyr Glu Trp

<210> SEQ ID NO 14
<211> LENGTH: 325
<212> TYPE: PRT
<213> ORGANISM: Neisseria species
<220> FEATURE:
<221> NAME/KEY: MISC_FEATURE
<223> OTHER INFORMATION: NadA allele C (first-ATG start)

<400> SEQUENCE: 14

Met Ser Met Lys His Phe Pro Ser Lys Val Leu Thr Ala Ala Ile Leu
1               5                   10                  15

Ala Ala Leu Ser Gly Ser Ala Met Ala Asp Asn Ala Pro Thr Ala Asp
            20                  25                  30

Glu Ile Ala Lys Ala Ala Leu Val Asn Ser Tyr Asn Asn Thr Gln Asp
        35                  40                  45

Ile Asn Gly Phe Thr Val Gly Asp Thr Ile Tyr Asp Ile Lys Asn Asp
    50                  55                  60

Lys Ile Thr Lys Lys Glu Ala Thr Glu Ala Asp Val Glu Ala Asp Asp
65                  70                  75                  80

Phe Lys Gly Leu Gly Leu Lys Glu Val Val Ala Gln His Asp Gln Ser
                85                  90                  95

Leu Ala Asp Leu Thr Glu Thr Val Asn Glu Asn Ser Glu Ala Leu Val
            100                 105                 110

Lys Thr Ala Ala Val Val Asn Asp Ile Ser Ala Asp Val Lys Ala Asn
        115                 120                 125

Thr Ala Ala Ile Gly Glu Asn Lys Ala Ala Ile Ala Thr Lys Ala Asp
    130                 135                 140

Lys Thr Glu Leu Asp Lys Val Ser Gly Lys Val Thr Glu Asn Glu Thr
145                 150                 155                 160

Ala Ile Gly Lys Lys Ala Asn Ser Ala Asp Val Tyr Thr Lys Ala Glu
                165                 170                 175

Val Tyr Thr Lys Gln Glu Ser Asp Asn Arg Phe Val Lys Ile Ser Asp
            180                 185                 190

Gly Ile Gly Asn Leu Asn Thr Thr Ala Asn Gly Leu Glu Thr Arg Leu
        195                 200                 205

Ala Ala Ala Glu Gln Ser Val Ala Asp His Gly Thr Arg Leu Ala Ser
    210                 215                 220

Ala Glu Lys Ser Ile Thr Glu His Gly Thr Arg Leu Asn Gly Leu Asp
225                 230                 235                 240

Arg Thr Val Ser Asp Leu Arg Lys Glu Thr Arg Gln Gly Leu Ala Glu
                245                 250                 255

Gln Ala Ala Leu Ser Gly Leu Phe Gln Pro Tyr Asn Val Gly Arg Phe
            260                 265                 270

Asn Val Thr Ala Ala Val Gly Gly Tyr Lys Ser Glu Ser Ala Val Ala
        275                 280                 285

Ile Gly Thr Gly Phe Arg Phe Thr Glu Asn Phe Ala Ala Lys Ala Gly
    290                 295                 300

Val Ala Val Gly Thr Ser Ser Gly Ser Ser Ala Ala Tyr His Val Gly
305                 310                 315                 320

Val Asn Tyr Glu Trp
            325

<210> SEQ ID NO 15
<211> LENGTH: 971
<212> TYPE: DNA
<213> ORGANISM: Neisseria species
<220> FEATURE:
<221> NAME/KEY: misc_feature
<223> OTHER INFORMATION: coding sequence for SEQ ID NO 13

<400> SEQUENCE: 15

| | | |
|---|---|---|
| atgaaacact tccatccaa gtactgacc gcagccatcc ttgccgccct cagcggcagc | 60 |
| gcaatggcag acaacgcccc caccgctgac gaaattgcca agccgccct agttaactcc | 120 |
| tacaacaata cccaagacat caacggattc acagtcggag acaccatcta cgacattaaa | 180 |
| aatgacaaga ttccaaaaaa agaagcaaca gaagccgatg ttgaagctga cgactttaaa | 240 |
| ggtctgggtc tgaaagaagt cgtggctcaa cacgaccaaa gccttgccga cctgaccgam | 300 |
| ccgtcaatga aaacagcgaa gcattggtaa aaaccgccgc ggttgtcaat gacatcagtg | 360 |
| ccgatgtcaa agccaacaca gcagctatcg gggaaaacaa agctgctatc gctacaaaag | 420 |
| cagacaaaac cgaactggat aaagtgtccg gcaaagtaac cgagaacgag actgctatcg | 480 |
| gtaaaaaagc aaacagtgcc gacgtgtaca ctaaagctga ggtgtacacc aaacaagagt | 540 |
| ctgacaacag atttgtcaaa attagtacg gaatcggtaa tctgaacact actgccaatg | 600 |
| gattggagac acgcttggcc gctgccgaac aatccgttgc agaccacggt acgcgcttgg | 660 |
| cttctgccga aaaatccatt accgaacacg gtacgcgcct gaacggtttg gatagaacag | 720 |
| tgtcagacct gcgtaaagaa acccgccaag gccttgcaga caagccgcg ctctccggtc | 780 |
| tgttccaacc ttacaacgtg ggtcggttca atgtaacggc tgcagtcggc ggctacaaat | 840 |
| ccgaatcggc agtcgccatc ggtaccggct tccgctttac cgaaaacttt gccgccaaag | 900 |
| caggcgtggc agtcggcact tcgtccggtt cttccgcagc ctaccatgtc ggcgtcaatt | 960 |
| acgagtggta a | 971 |

<210> SEQ ID NO 16
<211> LENGTH: 22
<212> TYPE: DNA
<213> ORGANISM: Artificial Sequence
<220> FEATURE:
<221> NAME/KEY: misc_feature
<223> OTHER INFORMATION: forward primer

<400> SEQUENCE: 16
gtcgacgtcc tcgattacga ag                                        22

<210> SEQ ID NO 17
<211> LENGTH: 22
<212> TYPE: DNA
<213> ORGANISM: Artificial Sequence
<220> FEATURE:
<221> NAME/KEY: misc_feature
<223> OTHER INFORMATION: reverse primer

<400> SEQUENCE: 17
cgaggcgatt gtcaaaccgt tc                                        22

<210> SEQ ID NO 18

```
<211> LENGTH: 32
<212> TYPE: DNA
<213> ORGANISM: Artificial Sequence
<220> FEATURE:
<221> NAME/KEY: misc_feature
<223> OTHER INFORMATION: forward primer

<400> SEQUENCE: 18
cgcggatccg ctagcggaca cacttatttc gg                              32

<210> SEQ ID NO 19
<211> LENGTH: 29
<212> TYPE: DNA
<213> ORGANISM: Artificial Sequence
<220> FEATURE:
<221> NAME/KEY: misc_feature
<223> OTHER INFORMATION: reverse primer

<400> SEQUENCE: 19
cccgctcgag ccagcggtag cctaatttg                                  29

<210> SEQ ID NO 20
<211> LENGTH: 33
<212> TYPE: DNA
<213> ORGANISM: Artificial Sequence
<220> FEATURE:
<221> NAME/KEY: misc_feature
<223> OTHER INFORMATION: forward primer

<400> SEQUENCE: 20
cgcggatccg ctagcaaaac aaccgacaaa cgg                             33

<210> SEQ ID NO 21
<211> LENGTH: 32
<212> TYPE: DNA
<213> ORGANISM: Artificial Sequence
<220> FEATURE:
<221> NAME/KEY: misc_feature
<223> OTHER INFORMATION: reverse primer

<400> SEQUENCE: 21
cccgctcgag ttaccagcgg tagcctaatt tg                              32

<210> SEQ ID NO 22
<211> LENGTH: 41
<212> TYPE: DNA
<213> ORGANISM: Artificial Sequence
<220> FEATURE:
<221> NAME/KEY: misc_feature
<223> OTHER INFORMATION: mutagenesis primer

<400> SEQUENCE: 22
ctcatttggc gacgctggct caccaatgtt tatctatgat g                    41

<210> SEQ ID NO 23
<211> LENGTH: 41
<212> TYPE: DNA
<213> ORGANISM: Artificial Sequence
<220> FEATURE:
<221> NAME/KEY: misc_feature
<223> OTHER INFORMATION: mutagenesis primer

<400> SEQUENCE: 23
catcatagat aaacattggt gagccagcgt cgccaaatga g                    41

<210> SEQ ID NO 24
<211> LENGTH: 32
```

```
<212> TYPE: DNA
<213> ORGANISM: Artificial Sequence
<220> FEATURE:
<221> NAME/KEY: misc_feature
<223> OTHER INFORMATION: forward primer

<400> SEQUENCE: 24
cgcggatccg ctagcggaca cacttatttc gg                          32

<210> SEQ ID NO 25
<211> LENGTH: 26
<212> TYPE: DNA
<213> ORGANISM: Artificial Sequence
<220> FEATURE:
<221> NAME/KEY: misc_feature
<223> OTHER INFORMATION: reverse primer

<400> SEQUENCE: 25
cccgctcgag cagcgcgtca aggctt                                 26

<210> SEQ ID NO 26
<211> LENGTH: 124
<212> TYPE: DNA
<213> ORGANISM: Artificial Sequence
<220> FEATURE:
<221> NAME/KEY: misc_feature
<223> OTHER INFORMATION: forward primer

<400> SEQUENCE: 26
gggaattcca tatgaaagcc aaacgtttta aaattaacgc catatcctta tccatctttc     60
ttgcctatgc ccttacgcca tactcagaag cggctagcga caacgcgcaa agccttgacg    120
cgct                                                                124

<210> SEQ ID NO 27
<211> LENGTH: 32
<212> TYPE: DNA
<213> ORGANISM: Artificial Sequence
<220> FEATURE:
<221> NAME/KEY: misc_feature
<223> OTHER INFORMATION: reverse primer

<400> SEQUENCE: 27
cccgctcgag ttaccagcgg tagcctaatt tg                          32

<210> SEQ ID NO 28
<211> LENGTH: 24
<212> TYPE: DNA
<213> ORGANISM: Artificial Sequence
<220> FEATURE:
<221> NAME/KEY: misc_feature
<223> OTHER INFORMATION: knockout primer

<400> SEQUENCE: 28
gctctagagg aggctgtcga aacc                                   24

<210> SEQ ID NO 29
<211> LENGTH: 26
<212> TYPE: DNA
<213> ORGANISM: Artificial Sequence
<220> FEATURE:
<221> NAME/KEY: misc_feature
<223> OTHER INFORMATION: knockout primer

<400> SEQUENCE: 29
tcccccgggc ggttgtccgt ttgtcg                                 26
```

<210> SEQ ID NO 30
<211> LENGTH: 27
<212> TYPE: DNA
<213> ORGANISM: Artificial Sequence
<220> FEATURE:
<221> NAME/KEY: misc_feature
<223> OTHER INFORMATION: knockout primer

<400> SEQUENCE: 30
tcccccgggg cgggcatcaa attaggc                              27

<210> SEQ ID NO 31
<211> LENGTH: 27
<212> TYPE: DNA
<213> ORGANISM: Artificial Sequence
<220> FEATURE:
<221> NAME/KEY: misc_feature
<223> OTHER INFORMATION: knockout primer

<400> SEQUENCE: 31
cccgctcgag cgcaaccgtc cgctgac                              27

<210> SEQ ID NO 32
<211> LENGTH: 1455
<212> TYPE: PRT
<213> ORGANISM: Neisseria species
<220> FEATURE:
<221> NAME/KEY: MISC_FEATURE
<223> OTHER INFORMATION: SEQ ID NO 650 from WO99/24578

<400> SEQUENCE: 32

```
Met Lys Thr Thr Asp Lys Arg Thr Thr Glu Thr His Arg Lys Ala Pro
 1               5                  10                  15

Lys Thr Gly Arg Ile Arg Phe Ser Pro Ala Tyr Leu Ala Ile Cys Leu
             20                  25                  30

Ser Phe Gly Ile Leu Pro Gln Ala Trp Ala Gly His Thr Tyr Phe Gly
         35                  40                  45

Ile Asn Tyr Gln Tyr Tyr Arg Asp Phe Ala Glu Asn Lys Gly Lys Phe
     50                  55                  60

Ala Val Gly Ala Lys Asp Ile Glu Val Tyr Asn Lys Lys Gly Glu Leu
 65                  70                  75                  80

Val Gly Lys Ser Met Thr Lys Ala Pro Met Ile Asp Phe Ser Val Val
                 85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220
```

-continued

```
Ser Trp Leu Val Gly Gly Asn Thr Phe Ala Gln Asn Gly Ser Gly
225                 230                 235                 240

Gly Thr Val Asn Leu Gly Ser Glu Lys Ile Lys His Ser Pro Tyr Gly
            245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
            325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
            405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
            485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
            565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
```

645                 650                 655
His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Trp Ser Arg Asn Val Ala Lys Val Lys Gly Asp Trp
    690                 695                 700

His Leu Ser Asn His Ala Gln Ala Val Phe Gly Val Ala Pro His Gln
705                 710                 715                 720

Ser His Thr Ile Cys Thr Arg Ser Asp Trp Thr Gly Leu Thr Asn Cys
            725                 730                 735

Val Glu Lys Thr Ile Thr Asp Lys Val Ile Ala Ser Leu Thr Lys
        740                 745                 750

Thr Asp Ile Ser Gly Asn Val Asp Leu Ala Asp His Ala His Leu Asn
    755                 760                 765

Leu Thr Gly Leu Ala Thr Leu Asn Gly Asn Leu Ser Ala Asn Gly Asp
770                 775                 780

Thr Arg Tyr Thr Val Ser His Asn Ala Thr Gln Asn Gly Asn Leu Ser
785                 790                 795                 800

Leu Val Gly Asn Ala Gln Ala Thr Phe Asn Gln Ala Thr Leu Asn Gly
            805                 810                 815

Asn Thr Ser Ala Ser Gly Asn Ala Ser Phe Asn Leu Ser Asp His Ala
        820                 825                 830

Val Gln Asn Gly Ser Leu Thr Leu Ser Gly Asn Ala Lys Ala Asn Val
    835                 840                 845

Ser His Ser Ala Leu Asn Gly Asn Val Ser Leu Ala Asp Lys Ala Val
850                 855                 860

Phe His Phe Glu Ser Ser Arg Phe Thr Gly Gln Ile Ser Gly Gly Lys
865                 870                 875                 880

Asp Thr Ala Leu His Leu Lys Asp Ser Glu Trp Thr Leu Pro Ser Gly
            885                 890                 895

Thr Glu Leu Gly Asn Leu Asn Leu Asp Asn Ala Thr Ile Thr Leu Asn
        900                 905                 910

Ser Ala Tyr Arg His Asp Ala Ala Gly Ala Gln Thr Gly Ser Ala Thr
    915                 920                 925

Asp Ala Pro Arg Arg Ser Arg Arg Ser Arg Ser Leu Leu Ser
930                 935                 940

Val Thr Pro Pro Thr Ser Val Glu Ser Arg Phe Asn Thr Leu Thr Val
945                 950                 955                 960

Asn Gly Lys Leu Asn Gly Gln Gly Thr Phe Arg Phe Met Ser Glu Leu
            965                 970                 975

Phe Gly Tyr Arg Ser Asp Lys Leu Lys Leu Ala Glu Ser Ser Glu Gly
        980                 985                 990

Thr Tyr Thr Leu Ala Val Asn Asn Thr Gly Asn Glu Pro Ala Ser Leu
    995                 1000                1005

Glu Gln Leu Thr Trp Glu Gly Lys Asp Asn Lys Pro Leu Ser Glu Asn
    1010                1015                1020

Leu Asn Phe Thr Leu Gln Asn Glu His Val Asp Ala Gly Ala Trp Arg
1025                1030                1035                1040

Tyr Gln Leu Ile Arg Lys Asp Gly Glu Phe Arg Leu His Asn Pro Val
            1045                1050                1055

Lys Glu Gln Glu Leu Ser Asp Lys Leu Gly Lys Ala Glu Ala Lys Lys
        1060                1065                1070

```
Gln Ala Glu Lys Asp Asn Ala Gln Ser Leu Asp Ala Leu Ile Ala Ala
        1075                1080                1085

Gly Arg Asp Ala Val Glu Lys Thr Glu Ser Val Ala Glu Pro Ala Arg
    1090                1095                1100

Gln Ala Gly Gly Glu Asn Val Gly Ile Met Gln Ala Glu Glu Lys
1105                1110                1115                1120

Lys Arg Val Gln Ala Asp Lys Asp Thr Ala Leu Ala Lys Gln Arg Glu
        1125                1130                1135

Ala Glu Thr Arg Pro Ala Thr Thr Ala Phe Pro Arg Ala Arg Arg Ala
        1140                1145                1150

Arg Arg Asp Leu Pro Gln Leu Gln Pro Gln Pro Gln Pro Gln
        1155                1160                1165

Arg Asp Leu Ile Ser Arg Tyr Ala Asn Ser Gly Leu Ser Glu Phe Ser
        1170                1175                1180

Ala Thr Leu Asn Ser Val Phe Ala Val Gln Asp Glu Leu Asp Arg Val
1185                1190                1195                1200

Phe Ala Glu Asp Arg Arg Asn Ala Val Trp Thr Ser Gly Ile Arg Asp
        1205                1210                1215

Thr Lys His Tyr Arg Ser Gln Asp Phe Arg Ala Tyr Arg Gln Gln Thr
        1220                1225                1230

Asp Leu Arg Gln Ile Gly Met Gln Lys Asn Leu Gly Ser Gly Arg Val
        1235                1240                1245

Gly Ile Leu Phe Ser His Asn Arg Thr Glu Asn Thr Phe Asp Asp Gly
        1250                1255                1260

Ile Gly Asn Ser Ala Arg Leu Ala His Gly Ala Val Phe Gly Gln Tyr
1265                1270                1275                1280

Gly Ile Asp Arg Phe Tyr Ile Gly Ile Ser Ala Gly Ala Gly Phe Ser
        1285                1290                1295

Ser Gly Ser Leu Ser Asp Gly Ile Gly Gly Lys Ile Arg Arg Arg Val
        1300                1305                1310

Leu His Tyr Gly Ile Gln Ala Arg Tyr Arg Ala Gly Phe Gly Gly Phe
        1315                1320                1325

Gly Ile Glu Pro His Ile Gly Ala Thr Arg Tyr Phe Val Gln Lys Ala
        1330                1335                1340

Asp Tyr Arg Tyr Glu Asn Val Asn Ile Ala Thr Pro Gly Leu Ala Phe
1345                1350                1355                1360

Asn Arg Tyr Arg Ala Gly Ile Lys Ala Asp Tyr Ser Phe Lys Pro Ala
        1365                1370                1375

Gln His Ile Ser Ile Thr Pro Tyr Leu Ser Leu Ser Tyr Thr Asp Ala
        1380                1385                1390

Ala Ser Gly Lys Val Arg Thr Arg Val Asn Thr Ala Val Leu Ala Gln
        1395                1400                1405

Asp Phe Gly Lys Thr Arg Ser Ala Glu Trp Gly Val Asn Ala Glu Ile
        1410                1415                1420

Lys Gly Phe Thr Leu Ser Leu His Ala Ala Ala Lys Gly Pro Gln
1425                1430                1435                1440

Leu Glu Ala Gln His Ser Ala Gly Ile Lys Leu Gly Tyr Arg Trp
        1445                1450                1455

<210> SEQ ID NO 33
<211> LENGTH: 956
<212> TYPE: PRT
<213> ORGANISM: Neisseria species
<220> FEATURE:
```

-continued

<221> NAME/KEY: MISC_FEATURE
<223> OTHER INFORMATION: App domain derivative

<400> SEQUENCE: 33

```
Met Lys Thr Thr Asp Lys Arg Thr Thr Glu Thr His Arg Lys Ala Pro
 1               5                  10                  15

Lys Thr Gly Arg Ile Arg Phe Ser Pro Ala Tyr Leu Ala Ile Cys Leu
             20                  25                  30

Ser Phe Gly Ile Leu Pro Gln Ala Trp Ala Gly His Thr Tyr Phe Gly
         35                  40                  45

Ile Asn Tyr Gln Tyr Tyr Arg Asp Phe Ala Glu Asn Lys Gly Lys Phe
     50                  55                  60

Ala Val Gly Ala Lys Asp Ile Glu Val Tyr Asn Lys Lys Gly Glu Leu
 65                  70                  75                  80

Val Gly Lys Ser Met Thr Lys Ala Pro Met Ile Asp Phe Ser Val Val
                 85                  90                  95

Ser Arg Asn Gly Val Ala Ala Leu Val Gly Asp Gln Tyr Ile Val Ser
             100                 105                 110

Val Ala His Asn Gly Gly Tyr Asn Asn Val Asp Phe Gly Ala Glu Gly
         115                 120                 125

Arg Asn Pro Asp Gln His Arg Phe Thr Tyr Lys Ile Val Lys Arg Asn
     130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                 165                 170                 175

Thr Ser Tyr Met Asp Gly Arg Lys Tyr Ile Asp Gln Asn Asn Tyr Pro
             180                 185                 190

Asp Arg Val Arg Ile Gly Ala Gly Arg Gln Tyr Trp Arg Ser Asp Glu
         195                 200                 205

Asp Glu Pro Asn Asn Arg Glu Ser Ser Tyr His Ile Ala Ser Ala Tyr
     210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                 245                 250                 255

Phe Leu Pro Thr Gly Gly Ser Phe Gly Asp Ser Gly Ser Pro Met Phe
             260                 265                 270

Ile Tyr Asp Ala Gln Lys Gln Lys Trp Leu Ile Asn Gly Val Leu Gln
         275                 280                 285

Thr Gly Asn Pro Tyr Ile Gly Lys Ser Asn Gly Phe Gln Leu Val Arg
     290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                 325                 330                 335

Asn Gly Thr Gly Lys Ile Asn Ala Lys His Glu His Asn Ser Leu Pro
             340                 345                 350

Asn Arg Leu Lys Thr Arg Thr Val Gln Leu Phe Asn Val Ser Leu Ser
         355                 360                 365

Glu Thr Ala Arg Glu Pro Val Tyr His Ala Ala Gly Gly Val Asn Ser
     370                 375                 380

Tyr Arg Pro Arg Leu Asn Asn Gly Glu Asn Ile Ser Phe Ile Asp Glu
385                 390                 395                 400
```

-continued

```
Gly Lys Gly Glu Leu Ile Leu Thr Ser Asn Ile Asn Gln Gly Ala Gly
                405                 410                 415
Gly Leu Tyr Phe Gln Gly Asp Phe Thr Val Ser Pro Glu Asn Asn Glu
            420                 425                 430
Thr Trp Gln Gly Ala Gly Val His Ile Ser Glu Asp Ser Thr Val Thr
        435                 440                 445
Trp Lys Val Asn Gly Val Ala Asn Asp Arg Leu Ser Lys Ile Gly Lys
    450                 455                 460
Gly Thr Leu His Val Gln Ala Lys Gly Glu Asn Gln Gly Ser Ile Ser
465                 470                 475                 480
Val Gly Asp Gly Thr Val Ile Leu Asp Gln Gln Ala Asp Asp Lys Gly
                485                 490                 495
Lys Lys Gln Ala Phe Ser Glu Ile Gly Leu Val Ser Gly Arg Gly Thr
            500                 505                 510
Val Gln Leu Asn Ala Asp Asn Gln Phe Asn Pro Asp Lys Leu Tyr Phe
        515                 520                 525
Gly Phe Arg Gly Gly Arg Leu Asp Leu Asn Gly His Ser Leu Ser Phe
    530                 535                 540
His Arg Ile Gln Asn Thr Asp Glu Gly Ala Met Ile Val Asn His Asn
545                 550                 555                 560
Gln Asp Lys Glu Ser Thr Val Thr Ile Thr Gly Asn Lys Asp Ile Ala
                565                 570                 575
Thr Thr Gly Asn Asn Asn Ser Leu Asp Ser Lys Lys Glu Ile Ala Tyr
            580                 585                 590
Asn Gly Trp Phe Gly Glu Lys Asp Thr Thr Lys Thr Asn Gly Arg Leu
        595                 600                 605
Asn Leu Val Tyr Gln Pro Ala Ala Glu Asp Arg Thr Leu Leu Leu Ser
    610                 615                 620
Gly Gly Thr Asn Leu Asn Gly Asn Ile Thr Gln Thr Asn Gly Lys Leu
625                 630                 635                 640
Phe Phe Ser Gly Arg Pro Thr Pro His Ala Tyr Asn His Leu Asn Asp
                645                 650                 655
His Trp Ser Gln Lys Glu Gly Ile Pro Arg Gly Glu Ile Val Trp Asp
            660                 665                 670
Asn Asp Trp Ile Asn Arg Thr Phe Lys Ala Glu Asn Phe Gln Ile Lys
        675                 680                 685
Gly Gly Gln Ala Val Val Ser Arg Asn Val Ala Lys Val Lys Gly Asp
    690                 695                 700
Trp His Leu Ser Asn His Ala Gln Ala Val Phe Gly Val Ala Pro His
705                 710                 715                 720
Gln Ser His Thr Ile Cys Thr Arg Ser Asp Trp Thr Gly Leu Thr Asn
                725                 730                 735
Cys Val Glu Lys Thr Ile Thr Asp Asp Lys Val Ile Ala Ser Leu Thr
            740                 745                 750
Lys Thr Asp Ile Ser Gly Asn Val Asp Leu Ala Asp His Ala His Leu
        755                 760                 765
Asn Leu Thr Gly Leu Ala Thr Leu Asn Gly Asn Leu Ser Ala Asn Gly
    770                 775                 780
Asp Thr Arg Tyr Thr Val Ser His Asn Ala Thr Gln Asn Gly Asn Leu
785                 790                 795                 800
Ser Leu Val Gly Asn Ala Gln Ala Thr Phe Asn Gln Ala Thr Leu Asn
                805                 810                 815
```

```
Gly Asn Thr Ser Ala Ser Gly Asn Ala Ser Phe Asn Leu Ser Asp His
                820                 825                 830

Ala Val Gln Asn Gly Ser Leu Thr Leu Ser Gly Asn Ala Lys Ala Asn
    835                 840                 845

Val Ser His Ser Ala Leu Asn Gly Asn Val Ser Leu Ala Asp Lys Ala
850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
                900                 905                 910

Asn Ser Ala Tyr Arg His Asp Ala Ala Gly Ala Gln Thr Gly Ser Ala
                915                 920                 925

Thr Asp Ala Pro Arg Arg Ser Arg Arg Ser Arg Arg Ser Leu Leu
                930                 935                 940

Ser Val Thr Pro Pro Thr Ser Val Glu Ser Arg Phe
945                 950                 955

<210> SEQ ID NO 34
<211> LENGTH: 1178
<212> TYPE: PRT
<213> ORGANISM: Neisseria species
<220> FEATURE:
<221> NAME/KEY: MISC_FEATURE
<223> OTHER INFORMATION: App domain derivative

<400> SEQUENCE: 34

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
                20                  25                  30

Ser Phe Gly Ile Leu Pro Gln Ala Trp Ala Gly His Thr Tyr Phe Gly
            35                  40                  45

Ile Asn Tyr Gln Tyr Tyr Arg Asp Phe Ala Glu Asn Lys Gly Lys Phe
50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
                100                 105                 110

Val Ala His Asn Gly Gly Tyr Asn Asn Val Asp Phe Gly Ala Glu Gly
            115                 120                 125

Arg Asn Pro Asp Gln His Arg Phe Thr Tyr Lys Ile Val Lys Arg Asn
                130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
                195                 200                 205

Asp Glu Pro Asn Asn Arg Glu Ser Ser Tyr His Ile Ala Ser Ala Tyr
            210                 215                 220
```

```
Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
            245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640
```

-continued

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
    690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
        755                 760                 765

Asn Leu Thr Gly Leu Ala Thr Leu Asn Gly Asn Leu Ser Ala Asn Gly
    770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
        835                 840                 845

Val Ser His Ser Ala Leu Asn Gly Asn Val Ser Leu Ala Asp Lys Ala
    850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
        915                 920                 925

Thr Asp Ala Pro Arg Arg Ser Arg Arg Ser Arg Ser Leu Leu
    930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
            980                 985                 990

Gly Thr Tyr Thr Leu Ala Val Asn Asn Thr Gly Asn Glu Pro Ala Ser
        995                 1000                1005

Leu Glu Gln Leu Thr Val Val Glu Gly Lys Asn Lys Pro Leu Ser
    1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala

```
              1060           1065           1070
Lys Lys Gln Ala Glu Lys Asp Asn Ala Gln Ser Leu Asp Ala Leu Ile
        1075              1080              1085

Ala Ala Gly Arg Asp Ala Val Glu Lys Thr Glu Ser Val Ala Glu Pro
        1090              1095              1100

Ala Arg Gln Ala Gly Gly Glu Asn Val Gly Ile Met Gln Ala Glu Glu
1105              1110              1115              1120

Glu Lys Lys Arg Val Gln Ala Asp Lys Asp Thr Ala Leu Ala Lys Gln
                 1125              1130              1135

Arg Glu Ala Glu Thr Arg Pro Ala Thr Thr Ala Phe Pro Arg Ala Arg
            1140              1145              1150

Arg Ala Arg Arg Asp Leu Pro Gln Leu Gln Pro Gln Pro Gln Pro Gln
        1155              1160              1165

Pro Gln Arg Asp Leu Ile Ser Arg Tyr Ala
        1170              1175

<210> SEQ ID NO 35
<211> LENGTH: 914
<212> TYPE: PRT
<213> ORGANISM: Neisseria species
<220> FEATURE:
<221> NAME/KEY: MISC_FEATURE
<223> OTHER INFORMATION: App domain derivative

<400> SEQUENCE: 35

Gly His Thr Tyr Phe Gly Ile Asn Tyr Gln Tyr Tyr Arg Asp Phe Ala
1               5                   10                  15

Glu Asn Lys Gly Lys Phe Ala Val Gly Ala Lys Asp Ile Glu Val Tyr
            20                  25                  30

Asn Lys Lys Gly Glu Leu Val Gly Lys Ser Met Thr Lys Ala Pro Met
        35                  40                  45

Ile Asp Phe Ser Val Val Ser Arg Asn Gly Val Ala Ala Leu Val Gly
50                  55                  60

Asp Gln Tyr Ile Val Ser Val Ala His Asn Gly Gly Tyr Asn Asn Val
65                  70                  75                  80

Asp Phe Gly Ala Glu Gly Arg Asn Pro Asp Gln His Arg Phe Thr Tyr
                85                  90                  95

Lys Ile Val Lys Arg Asn Asn Tyr Lys Ala Gly Thr Lys Gly His Pro
            100                 105                 110

Tyr Gly Gly Asp Tyr His Met Pro Arg Leu His Lys Phe Val Thr Asp
        115                 120                 125

Ala Glu Pro Val Glu Met Thr Ser Tyr Met Asp Gly Arg Lys Tyr Ile
130                 135                 140

Asp Gln Asn Asn Tyr Pro Asp Arg Val Arg Ile Gly Ala Gly Arg Gln
145                 150                 155                 160

Tyr Trp Arg Ser Asp Glu Asp Glu Pro Asn Asn Arg Glu Ser Ser Tyr
                165                 170                 175

His Ile Ala Ser Ala Tyr Ser Trp Leu Val Gly Gly Asn Thr Phe Ala
            180                 185                 190

Gln Asn Gly Ser Gly Gly Thr Val Asn Leu Gly Ser Glu Lys Ile
        195                 200                 205

Lys His Ser Pro Tyr Gly Phe Leu Pro Thr Gly Gly Ser Phe Gly Asp
    210                 215                 220

Ser Gly Ser Pro Met Phe Ile Tyr Asp Ala Gln Lys Gln Lys Trp Leu
225                 230                 235                 240
```

```
Ile Asn Gly Val Leu Gln Thr Gly Asn Pro Tyr Ile Gly Lys Ser Asn
            245                 250                 255

Gly Phe Gln Leu Val Arg Lys Asp Trp Phe Tyr Asp Glu Ile Phe Ala
        260                 265                 270

Gly Asp Thr His Ser Val Phe Tyr Glu Pro Arg Gln Asn Gly Lys Tyr
            275                 280                 285

Ser Phe Asn Asp Asp Asn Asn Gly Thr Gly Lys Ile Asn Ala Lys His
        290                 295                 300

Glu His Asn Ser Leu Pro Asn Arg Leu Lys Thr Arg Thr Val Gln Leu
305                 310                 315                 320

Phe Asn Val Ser Leu Ser Glu Thr Ala Arg Glu Pro Val Tyr His Ala
                325                 330                 335

Ala Gly Gly Val Asn Ser Tyr Arg Pro Arg Leu Asn Asn Gly Glu Asn
            340                 345                 350

Ile Ser Phe Ile Asp Glu Gly Lys Gly Glu Leu Ile Leu Thr Ser Asn
            355                 360                 365

Ile Asn Gln Gly Ala Gly Gly Leu Tyr Phe Gln Gly Asp Phe Thr Val
        370                 375                 380

Ser Pro Glu Asn Asn Glu Thr Trp Gln Gly Ala Gly Val His Ile Ser
385                 390                 395                 400

Glu Asp Ser Thr Val Thr Trp Lys Val Asn Gly Val Ala Asn Asp Arg
                405                 410                 415

Leu Ser Lys Ile Gly Lys Gly Thr Leu His Val Gln Ala Lys Gly Glu
            420                 425                 430

Asn Gln Gly Ser Ile Ser Val Gly Asp Gly Thr Val Ile Leu Asp Gln
        435                 440                 445

Gln Ala Asp Asp Lys Gly Lys Lys Gln Ala Phe Ser Glu Ile Gly Leu
450                 455                 460

Val Ser Gly Arg Gly Thr Val Gln Leu Asn Ala Asp Asn Gln Phe Asn
465                 470                 475                 480

Pro Asp Lys Leu Tyr Phe Gly Phe Arg Gly Gly Arg Leu Asp Leu Asn
                485                 490                 495

Gly His Ser Leu Ser Phe His Arg Ile Gln Asn Thr Asp Glu Gly Ala
            500                 505                 510

Met Ile Val Asn His Asn Gln Asp Lys Glu Ser Thr Val Thr Ile Thr
        515                 520                 525

Gly Asn Lys Asp Ile Ala Thr Thr Gly Asn Asn Ser Leu Asp Ser
530                 535                 540

Lys Lys Glu Ile Ala Tyr Asn Gly Trp Phe Gly Glu Lys Asp Thr Thr
545                 550                 555                 560

Lys Thr Asn Gly Arg Leu Asn Leu Val Tyr Gln Pro Ala Ala Glu Asp
                565                 570                 575

Arg Thr Leu Leu Leu Ser Gly Gly Thr Asn Leu Asn Gly Asn Ile Thr
            580                 585                 590

Gln Thr Asn Gly Lys Leu Phe Phe Ser Gly Arg Pro Thr Pro His Ala
        595                 600                 605

Tyr Asn His Leu Asn Asp His Trp Ser Gln Lys Glu Gly Ile Pro Arg
610                 615                 620

Gly Glu Ile Val Trp Asp Asn Asp Trp Ile Asn Arg Thr Phe Lys Ala
625                 630                 635                 640

Glu Asn Phe Gln Ile Lys Gly Gly Gln Ala Val Val Ser Arg Asn Val
                645                 650                 655

Ala Lys Val Lys Gly Asp Trp His Leu Ser Asn His Ala Gln Ala Val
```

```
                660             665             670
Phe Gly Val Ala Pro His Gln Ser His Thr Ile Cys Thr Arg Ser Asp
            675                 680             685

Trp Thr Gly Leu Thr Asn Cys Val Glu Lys Thr Ile Thr Asp Asp Lys
690                 695                 700

Val Ile Ala Ser Leu Thr Lys Thr Asp Ile Ser Gly Asn Val Asp Leu
705                 710                 715                 720

Ala Asp His Ala His Leu Asn Leu Thr Gly Leu Ala Thr Leu Asn Gly
                725                 730                 735

Asn Leu Ser Ala Asn Gly Asp Thr Arg Tyr Thr Val Ser His Asn Ala
                740                 745                 750

Thr Gln Asn Gly Asn Leu Ser Leu Val Gly Asn Ala Gln Ala Thr Phe
                755                 760                 765

Asn Gln Ala Thr Leu Asn Gly Asn Thr Ser Ala Ser Gly Asn Ala Ser
                770                 775                 780

Phe Asn Leu Ser Asp His Ala Val Gln Asn Gly Ser Leu Thr Leu Ser
785                 790                 795                 800

Gly Asn Ala Lys Ala Asn Val Ser His Ser Ala Leu Asn Gly Asn Val
                805                 810                 815

Ser Leu Ala Asp Lys Ala Val Phe His Phe Glu Ser Ser Arg Phe Thr
                820                 825                 830

Gly Gln Ile Ser Gly Lys Asp Thr Ala Leu His Leu Lys Asp Ser
                835                 840                 845

Glu Trp Thr Leu Pro Ser Gly Thr Glu Leu Gly Asn Leu Asn Leu Asp
                850                 855                 860

Asn Ala Thr Ile Thr Leu Asn Ser Ala Tyr Arg His Asp Ala Ala Gly
865                 870                 875                 880

Ala Gln Thr Gly Ser Ala Thr Asp Ala Pro Arg Arg Ser Arg Arg
                885                 890                 895

Ser Arg Arg Ser Leu Leu Ser Val Thr Pro Pro Thr Ser Val Glu Ser
                900                 905                 910

Arg Phe
```

<210> SEQ ID NO 36
<211> LENGTH: 1136
<212> TYPE: PRT
<213> ORGANISM: Neisseria species
<220> FEATURE:
<221> NAME/KEY: MISC_FEATURE
<223> OTHER INFORMATION: App domain derivative

<400> SEQUENCE: 36

```
Gly His Thr Tyr Phe Gly Ile Asn Tyr Gln Tyr Tyr Arg Asp Phe Ala
1               5                   10                  15

Glu Asn Lys Gly Lys Phe Ala Val Gly Ala Lys Asp Ile Glu Val Tyr
                20                  25                  30

Asn Lys Lys Gly Glu Leu Val Gly Lys Ser Met Thr Lys Ala Pro Met
            35                  40                  45

Ile Asp Phe Ser Val Val Ser Arg Asn Gly Val Ala Ala Leu Val Gly
50                  55                  60

Asp Gln Tyr Ile Val Ser Val Ala His Asn Gly Tyr Asn Asn Val
65                  70                  75                  80

Asp Phe Gly Ala Glu Gly Arg Asn Pro Asp Gln His Arg Phe Thr Tyr
                85                  90                  95

Lys Ile Val Lys Arg Asn Asn Tyr Lys Ala Gly Thr Lys Gly His Pro
```

```
                100                 105                 110
        Tyr Gly Gly Asp Tyr His Met Pro Arg Leu His Lys Phe Val Thr Asp
                    115                 120                 125
        Ala Glu Pro Val Glu Met Thr Ser Tyr Met Asp Gly Arg Lys Tyr Ile
        130                 135                 140
        Asp Gln Asn Asn Tyr Pro Asp Arg Val Arg Ile Gly Ala Gly Arg Gln
        145                 150                 155                 160
        Tyr Trp Arg Ser Asp Glu Asp Pro Asn Asn Arg Glu Ser Ser Tyr
                    165                 170                 175
        His Ile Ala Ser Ala Tyr Ser Trp Leu Val Gly Gly Asn Thr Phe Ala
                    180                 185                 190
        Gln Asn Gly Ser Gly Gly Thr Val Asn Leu Gly Ser Glu Lys Ile
                    195                 200                 205
        Lys His Ser Pro Tyr Gly Phe Leu Pro Thr Gly Gly Ser Phe Gly Asp
                    210                 215                 220
        Ser Gly Ser Pro Met Phe Ile Tyr Asp Ala Gln Lys Gln Lys Trp Leu
        225                 230                 235                 240
        Ile Asn Gly Val Leu Gln Thr Gly Asn Pro Tyr Ile Gly Lys Ser Asn
                    245                 250                 255
        Gly Phe Gln Leu Val Arg Lys Asp Trp Phe Tyr Asp Glu Ile Phe Ala
                    260                 265                 270
        Gly Asp Thr His Ser Val Phe Tyr Glu Pro Arg Gln Asn Gly Lys Tyr
                    275                 280                 285
        Ser Phe Asn Asp Asp Asn Asn Gly Thr Gly Lys Ile Asn Ala Lys His
                    290                 295                 300
        Glu His Asn Ser Leu Pro Asn Arg Leu Lys Thr Arg Thr Val Gln Leu
        305                 310                 315                 320
        Phe Asn Val Ser Leu Ser Glu Thr Ala Arg Glu Pro Val Tyr His Ala
                    325                 330                 335
        Ala Gly Gly Val Asn Ser Tyr Arg Pro Arg Leu Asn Asn Gly Glu Asn
                    340                 345                 350
        Ile Ser Phe Ile Asp Glu Gly Lys Gly Glu Leu Ile Leu Thr Ser Asn
                    355                 360                 365
        Ile Asn Gln Gly Ala Gly Gly Leu Tyr Phe Gln Gly Asp Phe Thr Val
                    370                 375                 380
        Ser Pro Glu Asn Glu Thr Trp Gln Gly Ala Gly Val His Ile Ser
        385                 390                 395                 400
        Glu Asp Ser Thr Val Thr Trp Lys Val Asn Gly Val Ala Asn Asp Arg
                    405                 410                 415
        Leu Ser Lys Ile Gly Lys Gly Thr Leu His Val Gln Ala Lys Gly Glu
                    420                 425                 430
        Asn Gln Gly Ser Ile Ser Val Gly Asp Gly Thr Val Ile Leu Asp Gln
                    435                 440                 445
        Gln Ala Asp Asp Lys Gly Lys Lys Gln Ala Phe Ser Glu Ile Gly Leu
                    450                 455                 460
        Val Ser Gly Arg Gly Thr Val Gln Leu Asn Ala Asp Asn Gln Phe Asn
        465                 470                 475                 480
        Pro Asp Lys Leu Tyr Phe Gly Phe Arg Gly Arg Leu Asp Leu Asn
                    485                 490                 495
        Gly His Ser Leu Ser Phe His Arg Ile Gln Asn Thr Asp Glu Gly Ala
                    500                 505                 510
        Met Ile Val Asn His Asn Gln Asp Lys Glu Ser Thr Val Thr Ile Thr
                    515                 520                 525
```

-continued

```
Gly Asn Lys Asp Ile Ala Thr Thr Gly Asn Asn Ser Leu Asp Ser
            530                 535                 540
Lys Lys Glu Ile Ala Tyr Asn Gly Trp Phe Gly Glu Lys Asp Thr Thr
545                 550                 555                 560
Lys Thr Asn Gly Arg Leu Asn Leu Val Tyr Gln Pro Ala Ala Glu Asp
                565                 570                 575
Arg Thr Leu Leu Leu Ser Gly Gly Thr Asn Leu Asn Gly Asn Ile Thr
            580                 585                 590
Gln Thr Asn Gly Lys Leu Phe Phe Ser Gly Arg Pro Thr Pro His Ala
            595                 600                 605
Tyr Asn His Leu Asn Asp His Trp Ser Gln Lys Glu Gly Ile Pro Arg
            610                 615                 620
Gly Glu Ile Val Trp Asp Asn Asp Trp Ile Asn Arg Thr Phe Lys Ala
625                 630                 635                 640
Glu Asn Phe Gln Ile Lys Gly Gly Gln Ala Val Val Ser Arg Asn Val
                645                 650                 655
Ala Lys Val Lys Gly Asp Trp His Leu Ser Asn His Ala Gln Ala Val
            660                 665                 670
Phe Gly Val Ala Pro His Gln Ser His Thr Ile Cys Thr Arg Ser Asp
            675                 680                 685
Trp Thr Gly Leu Thr Asn Cys Val Glu Lys Thr Ile Thr Asp Asp Lys
690                 695                 700
Val Ile Ala Ser Leu Thr Lys Thr Asp Ile Ser Gly Asn Val Asp Leu
705                 710                 715                 720
Ala Asp His Ala His Leu Asn Leu Thr Gly Leu Ala Thr Leu Asn Gly
            725                 730                 735
Asn Leu Ser Ala Asn Gly Asp Thr Arg Tyr Thr Val Ser His Asn Ala
            740                 745                 750
Thr Gln Asn Gly Asn Leu Ser Leu Val Gly Asn Ala Gln Ala Thr Phe
            755                 760                 765
Asn Gln Ala Thr Leu Asn Gly Asn Thr Ser Ala Ser Gly Asn Ala Ser
            770                 775                 780
Phe Asn Leu Ser Asp His Ala Val Gln Asn Gly Ser Leu Thr Leu Ser
785                 790                 795                 800
Gly Asn Ala Lys Ala Asn Val Ser His Ser Ala Leu Asn Gly Asn Val
            805                 810                 815
Ser Leu Ala Asp Lys Ala Val Phe His Phe Glu Ser Ser Arg Phe Thr
            820                 825                 830
Gly Gln Ile Ser Gly Gly Lys Asp Thr Ala Leu His Leu Lys Asp Ser
            835                 840                 845
Glu Trp Thr Leu Pro Ser Gly Thr Glu Leu Gly Asn Leu Asn Leu Asp
850                 855                 860
Asn Ala Thr Ile Thr Leu Asn Ser Ala Tyr Arg His Asp Ala Ala Gly
865                 870                 875                 880
Ala Gln Arg Gly Ser Ala Thr Asp Ala Pro Arg Arg Ser Arg Arg
            885                 890                 895
Ser Arg Arg Ser Leu Leu Ser Val Thr Pro Pro Thr Ser Val Glu Ser
            900                 905                 910
Arg Phe Asn Thr Leu Thr Val Asn Gly Lys Leu Asn Gly Gln Gly Thr
            915                 920                 925
Phe Arg Phe Met Ser Glu Leu Phe Gly Tyr Arg Ser Asp Lys Leu Lys
            930                 935                 940
```

```
Leu Ala Glu Ser Ser Glu Gly Thr Tyr Thr Leu Ala Val Asn Asn Thr
945                 950                 955                 960

Gly Asn Glu Pro Ala Ser Leu Glu Gln Leu Thr Val Val Glu Gly Lys
            965                 970                 975

Asp Asn Lys Pro Leu Ser Glu Asn Leu Asn Phe Thr Leu Gln Asn Glu
            980                 985                 990

His Val Asp Ala Gly Ala Trp Arg Tyr Gln Leu Ile Arg Lys Asp Gly
        995                1000                1005

Glu Phe Arg Leu His Asn Pro Val Lys Glu Gln Glu Leu Ser Asp Lys
    1010                1015                1020

Leu Gly Lys Ala Glu Ala Lys Lys Gln Ala Glu Lys Asp Asn Ala Gln
1025                1030                1035                1040

Ser Leu Asp Ala Leu Ile Ala Ala Gly Arg Asp Ala Val Glu Lys Thr
                1045                1050                1055

Glu Ser Val Ala Glu Pro Ala Arg Gln Ala Gly Gly Glu Asn Val Gly
                1060                1065                1070

Ile Met Gln Ala Glu Glu Lys Lys Arg Val Gln Ala Asp Lys Asp
                1075                1080                1085

Thr Ala Leu Ala Lys Gln Arg Glu Ala Glu Thr Arg Pro Ala Thr Thr
    1090                1095                1100

Ala Phe Pro Arg Ala Arg Arg Ala Arg Asp Leu Pro Gln Leu Gln
1105                1110                1115                1120

Pro Gln Pro Gln Pro Gln Pro Arg Asp Leu Ile Ser Arg Tyr Ala
                1125                1130                1135

<210> SEQ ID NO 37
<211> LENGTH: 221
<212> TYPE: PRT
<213> ORGANISM: Neisseria species
<220> FEATURE:
<221> NAME/KEY: MISC_FEATURE
<223> OTHER INFORMATION: App domain derivative

<400> SEQUENCE: 37

Asn Thr Leu Thr Val Asn Gly Lys Leu Asn Gly Gln Gly Thr Phe Arg
 1               5                  10                  15

Phe Met Ser Glu Leu Phe Gly Tyr Arg Ser Asp Lys Leu Lys Leu Ala
                20                  25                  30

Glu Ser Ser Glu Gly Thr Tyr Thr Leu Ala Val Asn Asn Thr Gly Asn
            35                  40                  45

Glu Pro Ala Ser Leu Glu Gln Leu Thr Trp Glu Gly Lys Asp Asn Lys
        50                  55                  60

Pro Leu Ser Glu Asn Leu Asn Phe Thr Leu Gln Asn Glu His Val Asp
65                  70                  75                  80

Ala Gly Ala Trp Arg Tyr Gln Leu Ile Arg Lys Asp Gly Glu Phe Arg
                85                  90                  95

Leu His Asn Pro Val Lys Glu Gln Glu Leu Ser Asp Lys Leu Gly Lys
            100                 105                 110

Ala Glu Ala Lys Lys Gln Ala Glu Lys Asp Asn Ala Gln Ser Leu Asp
        115                 120                 125

Ala Leu Ile Ala Ala Gly Arg Asp Ala Val Glu Lys Thr Glu Ser Val
    130                 135                 140

Ala Glu Pro Ala Arg Gln Ala Gly Gly Glu Asn Val Gly Ile Met Gln
145                 150                 155                 160

Ala Glu Glu Glu Lys Lys Arg Val Gln Ala Asp Lys Asp Thr Ala Leu
                165                 170                 175
```

```
Ala Lys Gln Arg Glu Ala Glu Thr Arg Pro Ala Thr Ala Phe Pro
            180                 185                 190

Arg Ala Arg Arg Ala Arg Arg Asp Leu Pro Gln Leu Gln Pro Gln Pro
            195                 200                 205

Gln Pro Gln Pro Gln Arg Asp Leu Ile Ser Arg Tyr Ala
    210                 215                 220

<210> SEQ ID NO 38
<211> LENGTH: 279
<212> TYPE: PRT
<213> ORGANISM: Neisseria species
<220> FEATURE:
<221> NAME/KEY: MISC_FEATURE
<223> OTHER INFORMATION: App domain derivative

<400> SEQUENCE: 38

Asn Ser Gly Leu Ser Glu Phe Ser Ala Thr Leu Asn Ser Val Phe Ala
1               5                   10                  15

Val Gln Asp Glu Leu Asp Arg Val Phe Ala Glu Asp Arg Arg Asn Ala
            20                  25                  30

Val Trp Thr Ser Gly Ile Arg Asp Thr Lys His Tyr Arg Ser Gln Asp
        35                  40                  45

Phe Arg Ala Tyr Arg Gln Gln Thr Asp Leu Arg Gln Ile Gly Met Gln
    50                  55                  60

Lys Asn Leu Gly Ser Gly Arg Val Gly Ile Leu Phe Ser His Asn Arg
65                  70                  75                  80

Thr Glu Asn Thr Phe Asp Asp Gly Ile Gly Asn Ser Ala Arg Leu Ala
            85                  90                  95

His Gly Ala Val Phe Gly Gln Tyr Gly Ile Asp Arg Phe Tyr Ile Gly
            100                 105                 110

Ile Ser Ala Gly Ala Gly Phe Ser Ser Gly Ser Leu Ser Asp Gly Ile
        115                 120                 125

Gly Gly Lys Ile Arg Arg Arg Val Leu His Tyr Gly Ile Gln Ala Arg
    130                 135                 140

Tyr Arg Ala Gly Phe Gly Gly Phe Gly Ile Glu Pro His Ile Gly Ala
145                 150                 155                 160

Thr Arg Tyr Phe Val Gln Lys Ala Asp Tyr Arg Tyr Glu Asn Val Asn
                165                 170                 175

Ile Ala Thr Pro Gly Leu Ala Phe Asn Arg Tyr Arg Ala Gly Ile Lys
            180                 185                 190

Ala Asp Tyr Ser Phe Lys Pro Ala Gln His Ile Ser Ile Thr Pro Tyr
        195                 200                 205

Leu Ser Leu Ser Tyr Thr Asp Ala Ala Ser Gly Lys Val Arg Thr Arg
    210                 215                 220

Val Asn Thr Ala Val Leu Ala Gln Asp Phe Gly Lys Thr Arg Ser Ala
225                 230                 235                 240

Glu Trp Gly Val Asn Ala Glu Ile Lys Gly Phe Thr Leu Ser Leu His
                245                 250                 255

Ala Ala Ala Ala Lys Gly Pro Gln Leu Glu Ala Gln His Ser Ala Gly
            260                 265                 270

Ile Lys Leu Gly Tyr Arg Trp
        275

<210> SEQ ID NO 39
<211> LENGTH: 501
<212> TYPE: PRT
```

<213> ORGANISM: Neisseria species
<220> FEATURE:
<221> NAME/KEY: MISC_FEATURE
<223> OTHER INFORMATION: App domain derivative

<400> SEQUENCE: 39

| | | | | | | | | | | | | | | |
|---|---|---|---|---|---|---|---|---|---|---|---|---|---|---|
| Asn | Thr | Leu | Thr | Val | Asn | Gly | Lys | Leu | Asn | Gly | Gln | Gly | Thr | Phe | Arg |
| 1 | | | | 5 | | | | | 10 | | | | | 15 | |
| Phe | Met | Ser | Glu | Leu | Phe | Gly | Tyr | Arg | Ser | Asp | Lys | Leu | Lys | Leu | Ala |
| | | | 20 | | | | | 25 | | | | | 30 | | |
| Glu | Ser | Ser | Glu | Gly | Thr | Tyr | Thr | Leu | Ala | Val | Asn | Asn | Thr | Gly | Asn |
| | | | 35 | | | | | 40 | | | | | 45 | | |
| Glu | Pro | Ala | Ser | Leu | Glu | Gln | Leu | Thr | Val | Val | Glu | Gly | Lys | Asp | Asn |
| 50 | | | | | 55 | | | | | 60 | | | | | |
| Lys | Pro | Leu | Ser | Glu | Asn | Leu | Asn | Phe | Thr | Leu | Gln | Asn | Glu | His | Val |
| 65 | | | | | 70 | | | | | 75 | | | | | 80 |
| Asp | Ala | Gly | Ala | Trp | Arg | Tyr | Gln | Leu | Ile | Arg | Lys | Asp | Gly | Glu | Phe |
| | | | | 85 | | | | | 90 | | | | | 95 | |
| Arg | Leu | His | Asn | Pro | Val | Lys | Glu | Gln | Glu | Leu | Ser | Asp | Lys | Leu | Gly |
| | | | | 100 | | | | | 105 | | | | | 110 | |
| Lys | Ala | Glu | Ala | Lys | Lys | Gln | Ala | Glu | Lys | Asp | Asn | Ala | Gln | Ser | Leu |
| | | | | 115 | | | | | 120 | | | | | 125 | |
| Asp | Ala | Leu | Ile | Ala | Ala | Gly | Arg | Asp | Ala | Val | Glu | Lys | Thr | Glu | Ser |
| | 130 | | | | | 135 | | | | | 140 | | | | |
| Val | Ala | Glu | Pro | Ala | Arg | Gln | Ala | Gly | Gly | Glu | Asn | Val | Gly | Ile | Met |
| 145 | | | | | 150 | | | | | 155 | | | | | 160 |
| Gln | Ala | Glu | Glu | Glu | Lys | Lys | Arg | Val | Gln | Ala | Asp | Lys | Asp | Thr | Ala |
| | | | | 165 | | | | | 170 | | | | | 175 | |
| Leu | Ala | Lys | Gln | Arg | Glu | Ala | Glu | Thr | Arg | Pro | Ala | Thr | Thr | Ala | Phe |
| | | | | 180 | | | | | 185 | | | | | 190 | |
| Pro | Arg | Ala | Arg | Arg | Ala | Arg | Arg | Asp | Leu | Pro | Gln | Leu | Gln | Pro | Gln |
| | | | 195 | | | | | 200 | | | | | 205 | | |
| Pro | Gln | Pro | Gln | Pro | Gln | Arg | Asp | Leu | Ile | Ser | Arg | Tyr | Ala | Asn | Ser |
| 210 | | | | | 215 | | | | | 220 | | | | | |
| Gly | Leu | Ser | Glu | Phe | Ser | Ala | Thr | Leu | Asn | Ser | Val | Phe | Ala | Val | Gln |
| 225 | | | | | 230 | | | | | 235 | | | | | 240 |
| Asp | Glu | Leu | Asp | Arg | Val | Phe | Ala | Glu | Asp | Arg | Arg | Asn | Ala | Val | Trp |
| | | | | 245 | | | | | 250 | | | | | 255 | |
| Thr | Ser | Gly | Ile | Arg | Asp | Thr | Lys | His | Tyr | Arg | Ser | Gln | Asp | Phe | Arg |
| | | | 260 | | | | | 265 | | | | | 270 | | |
| Ala | Tyr | Arg | Gln | Gln | Thr | Asp | Leu | Arg | Gln | Ile | Gly | Met | Gln | Lys | Asn |
| | | 275 | | | | | 280 | | | | | 285 | | | |
| Leu | Gly | Ser | Gly | Arg | Val | Gly | Ile | Leu | Phe | Ser | His | Asn | Arg | Thr | Glu |
| | 290 | | | | | 295 | | | | | 300 | | | | |
| Asn | Thr | Phe | Asp | Asp | Gly | Ile | Gly | Asn | Ser | Ala | Arg | Leu | Ala | His | Gly |
| 305 | | | | | 310 | | | | | 315 | | | | | 320 |
| Ala | Val | Phe | Gly | Gln | Tyr | Gly | Ile | Asp | Arg | Phe | Tyr | Ile | Gly | Ile | Ser |
| | | | | 325 | | | | | 330 | | | | | 335 | |
| Ala | Gly | Ala | Gly | Phe | Ser | Ser | Gly | Ser | Leu | Ser | Asp | Gly | Ile | Gly | Gly |
| | | | | 340 | | | | | 345 | | | | | 350 | |
| Lys | Ile | Arg | Arg | Arg | Val | Leu | His | Tyr | Gly | Ile | Gln | Ala | Arg | Tyr | Arg |
| | | | | 355 | | | | | 360 | | | | | 365 | |
| Ala | Gly | Phe | Gly | Gly | Phe | Gly | Ile | Glu | Pro | His | Ile | Gly | Ala | Thr | Arg |
| | | | 370 | | | | | 375 | | | | | 380 | | |

```
Tyr Phe Val Gln Lys Ala Asp Tyr Arg Tyr Glu Asn Val Asn Ile Ala
385                 390                 395                 400

Thr Pro Gly Leu Ala Phe Asn Arg Tyr Arg Ala Gly Ile Lys Ala Asp
                405                 410                 415

Tyr Ser Phe Lys Pro Ala Gln His Ile Ser Ile Thr Pro Tyr Leu Ser
            420                 425                 430

Leu Ser Tyr Thr Asp Ala Ala Ser Gly Lys Val Arg Thr Arg Val Asn
        435                 440                 445

Thr Ala Val Leu Ala Gln Asp Phe Gly Lys Thr Arg Ser Ala Glu Trp
    450                 455                 460

Gly Val Asn Ala Glu Ile Lys Gly Phe Thr Leu Ser Leu His Ala Ala
465                 470                 475                 480

Ala Ala Lys Gly Pro Gln Leu Glu Ala Gln His Ser Ala Gly Ile Lys
                485                 490                 495

Leu Gly Tyr Arg Trp
            500

<210> SEQ ID NO 40
<211> LENGTH: 36
<212> TYPE: PRT
<213> ORGANISM: Neisseria species
<220> FEATURE:
<221> NAME/KEY: MISC_FEATURE
<223> OTHER INFORMATION: Residues of NadA

<400> SEQUENCE: 40

Ile Glu Lys Leu Thr Thr Lys Leu Ala Asp Thr Asp Ala Ala Leu Ala
1               5                   10                  15

Asp Thr Asp Ala Ala Leu Asp Glu Thr Thr Asn Ala Leu Asn Lys Leu
            20                  25                  30

Gly Glu Asn Ile
        35

<210> SEQ ID NO 41
<211> LENGTH: 270
<212> TYPE: DNA
<213> ORGANISM: Neisseria species
<220> FEATURE:
<221> NAME/KEY: misc_feature
<223> OTHER INFORMATION: partial coding sequence for NadA

<400> SEQUENCE: 41
acccatatcc tgacaaaatt aagacacgac accggcagaa ttgacatcag cataatatgc      60
acatattaac agatattaat gccgaactac ctaactgcaa gaattaaata ataaataaa     120 taaataaata aataaataaa ttgcgacaat gtattgtata tatgcctcct ttcatatata    180
ctttaatatg taaacaaact tggtggggat aaaatactta caaagatttt ccgccccatt    240
ttttatccac tcacaaaggt aatgagcatg                                     270

<210> SEQ ID NO 42
<211> LENGTH: 16
<212> TYPE: DNA
<213> ORGANISM: Neisseria species
<220> FEATURE:
<221> NAME/KEY: misc_feature
<223> OTHER INFORMATION: Partial sequence of MenA genome

<400> SEQUENCE: 42
tttccattcc aaacgc                                                     16
```

```
<210> SEQ ID NO 43
<211> LENGTH: 28
<212> TYPE: PRT
<213> ORGANISM: Neisseria species
<220> FEATURE:
<221> NAME/KEY: MISC_FEATURE
<223> OTHER INFORMATION: N. meningitidis

<400> SEQUENCE: 43

Arg Arg Ser Arg Arg Ser Leu Leu Ser Val Thr Pro Pro Ala Ser Ala
 1               5                  10                  15

Glu Ser His Phe Asn Thr Leu Thr Val Asn Gly Lys
            20                  25

<210> SEQ ID NO 44
<211> LENGTH: 33
<212> TYPE: PRT
<213> ORGANISM: Neisseria species
<220> FEATURE:
<221> NAME/KEY: MISC_FEATURE
<223> OTHER INFORMATION: N. meningitidis

<400> SEQUENCE: 44

Arg Arg Ala Arg Arg Asp Leu Pro Gln Pro Gln Pro Gln Pro Gln Pro
 1               5                  10                  15

Gln Pro Gln Arg Asp Glu Lys Leu Ile Ser Arg Tyr Ala Asn Ser Gly
            20                  25                  30

Leu

<210> SEQ ID NO 45
<211> LENGTH: 21
<212> TYPE: PRT
<213> ORGANISM: Haemophilus species
<220> FEATURE:
<221> NAME/KEY: MISC_FEATURE
<223> OTHER INFORMATION: H. influenzae

<400> SEQUENCE: 45

Arg Arg Ala Ala Arg Ala Ala Phe Pro Asp Thr Leu Pro Asp Gln Ser
 1               5                  10                  15

Leu Leu Asn Ala Leu
            20

<210> SEQ ID NO 46
<211> LENGTH: 26
<212> TYPE: PRT
<213> ORGANISM: Neisseria species
<220> FEATURE:
<221> NAME/KEY: MISC_FEATURE
<223> OTHER INFORMATION: N. gonorrhoeae

<400> SEQUENCE: 46

Arg Arg Arg Arg Arg Ala Ile Leu Pro Arg Pro Ala Pro Val Phe
 1               5                  10                  15

Ser Leu Asp Asp Tyr Asp Ala Lys Asp Asn
            20                  25

<210> SEQ ID NO 47
<211> LENGTH: 28
<212> TYPE: PRT
<213> ORGANISM: Bordetella species
<220> FEATURE:
<221> NAME/KEY: MISC_FEATURE
<223> OTHER INFORMATION: B. pertussis

<400> SEQUENCE: 47
```

```
Arg Arg Ala Arg Arg Ala Leu Arg Gln Asp Phe Phe Thr Pro Gly Ser
1               5                   10                  15

Val Val Arg Ala Gln Gly Asn Val Thr Val Gly Arg
            20                  25

<210> SEQ ID NO 48
<211> LENGTH: 4
<212> TYPE: PRT
<213> ORGANISM: Bordetella species
<220> FEATURE:
<221> NAME/KEY: MISC_FEATURE
<223> OTHER INFORMATION: B. bronchiseptica

<400> SEQUENCE: 48

Ser Asn Ala Leu
1

<210> SEQ ID NO 49
<211> LENGTH: 4
<212> TYPE: PRT
<213> ORGANISM: Serratia species
<220> FEATURE:
<221> NAME/KEY: MISC_FEATURE
<223> OTHER INFORMATION: S. marcescens

<400> SEQUENCE: 49

Leu Asn Ser Gly
1

<210> SEQ ID NO 50
<211> LENGTH: 4
<212> TYPE: PRT
<213> ORGANISM: Bordetella species
<220> FEATURE:
<221> NAME/KEY: MISC_FEATURE
<223> OTHER INFORMATION: B. pertussis

<400> SEQUENCE: 50

Val Asn Ala Ala
1

<210> SEQ ID NO 51
<211> LENGTH: 4
<212> TYPE: PRT
<213> ORGANISM: Haemophilus species
<220> FEATURE:
<221> NAME/KEY: MISC_FEATURE
<223> OTHER INFORMATION: H. influenzae

<400> SEQUENCE: 51

Leu Asn Ala Leu
1

<210> SEQ ID NO 52
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 4, 5, 6, 7, 9, 10, 11, 12, 13, 14, 16, 17, 18, 19,
      20, 21
<223> OTHER INFORMATION: Xaa = Any Amino Acid

<400> SEQUENCE: 52

Leu Xaa Xaa Xaa Xaa Xaa Xaa Leu Xaa Xaa Xaa Xaa Xaa Xaa Leu Xaa
```

```
      1               5                   10                  15
Xaa Xaa Xaa Xaa Xaa Leu
                20

<210> SEQ ID NO 53
<211> LENGTH: 5
<212> TYPE: PRT
<213> ORGANISM: N. meningitidis

<400> SEQUENCE: 53

Arg Arg Ser Arg Arg
 1               5

<210> SEQ ID NO 54
<211> LENGTH: 5
<212> TYPE: PRT
<213> ORGANISM: N. meningitidis

<400> SEQUENCE: 54

Arg Arg Ala Arg Arg
 1               5

<210> SEQ ID NO 55
<211> LENGTH: 12
<212> TYPE: PRT
<213> ORGANISM: N. meningitidis

<400> SEQUENCE: 55

Pro Gln Pro Gln Pro Gln Pro Gln Pro Gln Pro Gln
 1               5                   10

<210> SEQ ID NO 56
<211> LENGTH: 31
<212> TYPE: PRT
<213> ORGANISM: N. meningitidis

<400> SEQUENCE: 56

Arg Arg Ala Arg Arg Asp Leu Pro Gln Pro Gln Pro Gln Pro Gln Pro
 1               5                   10                  15

Gln Pro Gln Arg Asp Leu Ile Ser Arg Tyr Ala Asn Ser Gly Leu
            20                  25                  30

<210> SEQ ID NO 57
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 3
<223> OTHER INFORMATION: Xaa = Ala or Ser
<220> FEATURE:
<221> NAME/KEY: VARIANT
<222> LOCATION: 4
<223> OTHER INFORMATION: Xaa = Gly, Ala, Val, Leu, Ile, Pro, Phe, Met,
      or Trp

<400> SEQUENCE: 57

Xaa Asn Xaa Xaa
 1
```

MENINGOCOCCUS ADHESINS NADA, APP AND ORF 40

CROSS-REFERENCE TO RELATED APPLICATIONS

This application is a Continuation of Ser. No. 12/775,457, filed May 6, 2010, now abandoned, which is a Continuation of Ser. No. 10/484,703, filed Mar. 7, 2005, now abandoned, which is the National Phase of PCT Application PCT/IB02/03396, filed Jul. 26, 2002, which claims the benefit of GB Application 0211025.2, filed May 14, 2002, GB Application 0121591.2, filed Sep. 6, 2001, and GB Application 0118401.9, filed Jul. 27, 2001, all of which are incorporated herein by reference in their entirety.

TECHNICAL FIELD

This invention is in the field of biochemistry and, in particular, the biochemistry of the pathogenic bacteria in the genus *Neisseria* (e.g. *N. meningitidis* and *N. gonorrhea*).

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002100702SUBSEQLISTING2.TXT, date recorded: Apr. 30, 2015, size: 109 KB).

BACKGROUND

International patent applications WO99/24578, WO99/36544, WO99/57280 and WO00/22430 disclose proteins from *Neisseria meningitidis* and *Neisseria gonorrhea*. The complete genome sequence of serogroup B *N. meningitidis* has been published [Tettelin et al. (2000) *Science* 287:1809-1815] and has been subjected to analysis in order to identify vaccine antigens [Pizza et al. (2000) *Science* 287:1816-1820]. Approaches to expression of the proteins are disclosed in WO01/64922. The complete genome sequence of serogroup A *N. meningitidis* is also known [Parkhill et al. (2000) *Nature* 404:502-506].

Sequence data alone, however, does not reveal everything about this pathogen. Objects of the present invention include: (a) to provide ways of intervening in *Neisseria* biochemistry; (b) to provide new uses for known *Neisseria* proteins; (c) to provide alternative and improved forms of known *Neisseria* proteins, such as enzymatically inactive forms of known proteins or proteolytic products of known proteins; and (d) to provide materials useful for studying and modulating Neisserial adhesion.

DISCLOSURE OF THE INVENTION

Nomenclature Used Herein

'ORF40' is disclosed in example 1 of WO99/36544. Sequences from serogroups A and B of *N. meningitidis* are disclosed (SEQ IDs 1 to 6 therein). Other forms of the protein are disclosed in WO99/31132 and WO99/58683, and can also be found in GenBank (see gi accession numbers: 11352902, 7228562, 14578015, 12958107, 7228586, 7228572, 7228594, 7228588, 14578013, 7228568, 7228546, 7228548, 7228592, 14578009, 7228558, 7228600, 7228596, 7228542, 7228574, 7228552, 7228554, 14578023, 14578021, 11354080, 7228584 & 7228590). 'App' (adhesion and penetration protein) is disclosed as 'ORF1' in example 77 of WO99/24578. Sequences from serogroups A and B of *N. meningitidis* and from *N. gonorrhea* are disclosed (SEQ IDs 647 to 654 therein). Other forms of the protein are disclosed in WO99/55873, and can also be found in GenBank (see gi accession numbers: 11280386, 7227246, 11071865, 6977941, 11071863, 11280387, 7379205).

'NadA' (Neisserial adhesin A) from serogroup B of *N. meningitidis* is disclosed as protein '961' in WO99/57280 (SEQ IDs 2943 & 2944) and as 'NMB1994' by Tettelin et al. (see also GenBank accession numbers: 11352904 & 7227256) and in FIG. 9 herein. These proteins are preferably expressed other than as a fusion protein (e.g. without GST, MBP, his-tag or similar).

Preferred proteins for use according to the invention are those of serogroup B *N. meningitidis* strain MC58, strain 2996 or strain 394/98 (a New Zealand strain). It will be appreciated, however, that the invention is not in general limited by strain references to a particular protein (e.g. 'ORF40', 'App' etc.) may be taken to include that protein from any strain. In general, therefore, reference to any particular protein includes proteins which share sequence identity with one of the sequences disclosed above. The degree of 'sequence identity' is preferably greater than 50% (eg. 60%, 70%, 80%, 90%, 95%, 99% or more). This includes mutants and allelic variants. In the context of the present invention, sequence identity is preferably determined by the Smith-Waterman homology search algorithm as implemented in the MPSRCH program (Oxford Molecular), using an sane gap search with parameters gap open penalty=12 and gap extension penalty=1. Typically, 50% identity or more between two proteins is considered to be an indication of functional equivalence.

The naming conventions used in WO99/24578, WO99/36544 and WO99/57280 are also used herein (e.g. 'ORF4', 'ORF40', 'ORF40-1' etc. as used in V099/24578 and WO99/36544, 'm919', 'g919' and 'a919' etc. as used in WO99/57280).

Secreted App

It has been found that, when expressed in *E. coli* without a GST or his-tag fusion partner, App is exported to the outer membrane as a precursor of about 160 kDa, where it is processed and secreted into the culture.

The invention therefore provides a method for purifying processed App protein, comprising the steps of: expressing a gene encoding App protein in a non-Neisserial host cell; and purifying processed App protein from the culture medium.

The invention also provides purified protein obtainable by this process.

The App protein preferably includes its wild-type 42 residue signal peptide at the N-terminus i.e. no N-terminus fusion partner is used. It is also preferred not to include a C-terminus fusion partner.

To purify the protein front the culture medium the culture can be centrifuged and the protein can be recovered from the supernatant.

The non-Neisserial host cell is preferably a bacterium and is most preferably *E. coli*.

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5) to the RNA polymerase binding sequencer example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic, enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistake." In interferon 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tar promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sri.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of seine genes in prokaryotes. The bacteriophage T7 RNA polymerase/promoter system is an example of a coupled promote system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is railed the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokatyotic genes with weak ribosome-binding site [Sambrook et al. (1989) "Expression of cloned genes in *Escherichia coli*." In *Molecular Cloning: A Laboratory Manual*].

A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vivo incubation with a bacterial methionine N-terminal peptidase (EP-A-0219237).

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200 and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least ene sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0127328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter aria, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature*, 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbio. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990), *J. Bacteriol.* 172949, *Campylobacter*], [Cohen et al. (1973) *Proc. Natl. Acad. Sci.* 69:2110; Dower et al. (1988) *Nucleic Acids Res.* 16:6121; Kushner (1978) "An improved method for transformation of *Escherichia coli* with ColE1-derived plasmids. In *Genetic Engineering: Proceedings of the International Symposium on Genetic Engineering* (eds. H. W. Bayer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

Adherence Proteins

Example 22 of international patent application WO01/64922 discloses that *E. coli* which expresses protein NadA can adhere to human epithelial cells. This adherence activity has been further studied and it had also been found for App and ORF40.

The invention provides methods for preventing the attachment of Neisserial cells to epithelial cells.

References to a "Neisserial cell" in this section include any species of the bacterial genus *Neisseria*, including *N. gonorrhoeae* and *N. lactamica*. Preferably, however, the species is *N. meningitidis*. The *N. meningitidis* may be from any serogroup, including serogroups A, C, W135 and Y. Most preferably, however, it is *N. meningitidis* serogroup B.

References to an "epithelial cell" in this section include any cell found in or derived from the epithelium of a mammal. The cell may be in vitro (e.g. in cell culture) or in vivo. Preferred epithelial cells are from the nasopharynx. The cells are most preferably human cells.

Blocking the *Neisseria*-Epithelium Interaction

The invention provides a method for preventing the attachment of a Neisserial cell to an epithelial cell, wherein the ability of one or more App, ORF40 and/or NadA to bind to the epithelial cell is blocked.

The ability to bind may be blocked in various ways but, most conveniently, an antibody specific for App, ORF40 and/or NadA is used. The invention also provides antibody which is specific for App, ORF40 or NadA. This antibody preferably has an affinity for App, ORF40 and/or NadA of at least $10^{-7}$ M e.g. $10^{-8}$ M, $10^{-9}$ M, $10^{-10}$ M or tighter.

Antibodies for use in accordance with the invention may be polyclonal, but are preferably monoclonal. It will be appreciated that the term "antibody" includes whole antibodies (e.g. IgG, IgA etc), derivatives of whole antibodies which retain the antigen-binding sites (e.g. $F_{ab}$, $F_{ab'}$, $F_{(ab')2}$ etc.), single chain antibodies (e.g. sFv), chimeric antibodies, CDR-grafted antibodies, humanised antibodies, univalent antibodies, human monoclonal antibodies [e.g. Green (1999) *J. Immunol Methods* 231:11-23; Kipriyanov & Little (1999) *Mol. Biotechnol* 12:173-201 etc.] and the like. Humanised antibodies may be preferable to those which are fully human [e.g. Fletcher (2001) *Nature Biotechnology* 19:395-96].

As an alternative to using antibodies, antagonists of the interaction between App, ORF40 or NadA and its receptor on the epithelial cell may be used. As a further alternative, a soluble form of the epithelial cell receptor may be used as a decoy. These can be produced by removing the receptor's transmembrane and, optionally, cytoplasmic regions [e.g. EP-B2-0139417, EP-A-0609580 etc.].

The antibodies, antagonists and soluble receptors of the invention may be used as medicaments to prevent the attachment of a Neisserial cell to an epithelial cell.

Inhibiting Expression of the Neisserial Gene

The invention provides a method for preventing the attachment of a Neisserial cell to an epithelial cell, wherein protein expression from one or more of App, ORF40 and/or NadA is inhibited. The inhibition may be at the level of transcription and/or translation.

A preferred technique for inhibiting expression of the gene is antisense [e.g. Piddock (1998) *Curr Opin Microbiol* 1:502-8; Nielsen (2001) *Expert Opin Investig Drugs* 10:331-41; Good & Nielsen (1998) *Nature Biotechnol* 16:355-358; Rabman et al. (1991) *Antisense Res Dev* 1:319-327; *Methods in Enzymology* volumes 313 & 314; *Manual of Antisense Methodology* (eds. Hartmann & Endres); *Antisense Therapeutics* (ed. Agrawal) etc.]. Antibacterial antisense techniques are disclosed in, for example, international patent applications WO99/02673 and WO99/13893.

The invention also provides nucleic acid comprising a fragment of x or more nucleotides from nucleic acid which encodes App, ORF40 or NadA, wherein x is at least 8 (e.g. 8, 10, 12, 14, 16, 18, 20, 25, 30 or more). The nucleic acid will typically be single-stranded.

The nucleic acid is preferably of the formula 5'-$(N)_a$—(X)—$(N)_b$-3', wherein $0 \geq a \geq 15$, $0 \geq b \geq 15$, N is any nucleotide, and X is a fragment of a nucleic acid which encodes App, ORF40 or NadA. X preferably comprises at least 8 nucleotides (e.g. 8, 10, 12, 14, 16, 18, 20, 25, 30 or more). The values of a and b may independently be 0, 1, 2, 3, 4, 5, 6, 7, 8, 9, 10, 11, 12, 13, 14 or 15. Each individual nucleotide N in the —$(N)_a$— and —$(N)_b$— portions of the nucleic acid may be the same or different. The length of the nucleic acid (i.e. a+b+length of X) is preferably less than 100 (e.g. less than 90, 80, 70, 60, 50, 40, 30 etc.).

It will be appreciated that the term "nucleic acid" includes DNA, RNA, DNA/RNA hybrids, DNA and RNA analogues such as those containing modified backbones (with modifications in the sugar and/or phosphates e.g. phosphorothioates, phosphoramidites etc.), and also peptide nucleic acids (PNA) and any other polymer comprising purine and pyrimidine bases or other natural, chemically or biochemically modified, non-natural, or derivatized nucleotide bases etc. Nucleic acid according to the invention can be prepared in many ways (e.g. by chemical synthesis, from genomic or cDNA libraries, from the organism itself etc.) and can take various for (e.g. single stranded, double stranded, vectors, probes etc.).

The antisense nucleic acids of the invention may be used as medicaments to prevent the attachment of a Neisserial cell to an epithelial cell.

Knockout of the Neisserial gene

The invention provides a method far preventing the attachment of a Neisserial cell to an epithelial cell, wherein one or more of App, ORF40 and/or NadA is knocked out.

The invention also provides a *Neisseria* bacterium in which one or more of App, ORF40 and/or NadA has been knocked out.

Techniques for producing knockout bacteria are well known, and knockout *Neisseria* have been reported [e.g. Moe et al. (2001) *Infect. Immun.* 69:3762-3771; Seifert (1997) *Gene* 188:215-220; Zhu et al. (2000) *J. Bacteriol.* 182:439-447 etc.].

The knockout mutation may be situated in the coding region of the gene or may lie within its transcriptional control regions (e.g. within its promoter).

The knockout mutation will reduce the level of mRNA encoding App, ORF40 and/or NadA to <1% of that produced by the wild-type bacterium, preferably <0.5%, more preferably <0.1%, and most preferably to 0%.

The knockout mutants of the invention may be used as immunogenic compositions (e.g. as vaccines) to prevent Neisserial infection. Such a vaccine may include the mutant as a live attenuated bacterium.

Mutagenesis of the Neisserial Gene

The invention provides a method for preventing the attachment of a Neisserial cell to an epithelial cell, wherein one or more of App, ORF40 and/or NadA has a mutation which inhibits its activity.

The invention also provides a mutant protein, wherein the mutant protein comprises the amino acid sequence of App, ORF40 and/or NadA, or a fragment thereof, but wherein one or more amino acids of said amino acid sequence is/are mutated (e.g. see below for App).

The amino acids which is/are mutated preferably result in the reduction or removal of an activity of App, ORF40 and/or NadA which is responsible directly or indirectly for adhesion to epithelial cells.

For example, the mutation may inhibit an enzymatic activity or may remove a binding site in the protein.

The invention also provides nucleic acid encoding this mutant protein.

The invention also provides a method for producing this nucleic acid, comprising the steps of: (a) providing source nucleic acid encoding App, ORF40 or NadA, and (b) performing mutagenesis (e.g. site-directed mutagenesis) on said source nucleic acid to provide nucleic acid encoding a mutant protein.

Mutation may involve deletion, substitution, and/or insertion, any of which may be involve one or more amino acids. As an alternative, the mutation may involve truncation.

Mutagenesis of virulence factors is a well-established science for many bacteria [e.g. toxin mutagenesis described in WO93/13202; Rappuoli & Pizza, Chapter 1 of *Sourcebook of Bacterial Protein Toxins* (ISBN 0-12-053078-3); Pizza et al. (2001) *Vaccine* 19:2554-41; Alape-Giron et al. (2000) *Eur J Biochem* 267:5191-5197; Kitten et al. (2000) *Infect Immun* 68:4441-4451; Gubba et al. (2000) *Infect Immun* 68:3716-3719; Boulnois et al. (1991) *Mol Microbiol* 5:2611-2616 etc.] including *Neisseria* [e.g. Power et al. (2000) *Microbiology* 146:967-979; Forest et al. (1999) *Mol Microbiol* 31:743-752; Comelissen et al. (1998) *Mol Microbiol* 27:611-616; Lee et al. (1995) *Infect Immun* 63:2508-2515; Robertson et al. (1993) *Mol Microbiol* 8:891-901 etc.].

Mutagenesis may be specifically targeted to nucleic acid encoding App, ORF40 and/or NadA. Alternatively, mutagenesis may be global or random (e.g. by irradiation, chemical mutagenesis etc.), which will typically be followed by screening bacteria for those in which a mutation has been introduced into App, ORF40 and/or NadA. Such screening may be by hybridisation assays (e.g. Southern or Northern blots etc.), printer-based amplification (e.g. PCR), sequencing, proteomics, aberrant SDS-PAGE gel migration etc.

The mutant proteins and nucleic acids of the invention may be used as immunogenic compositions (e.g., as vaccines) to prevent Neisserial infection.

Screening Methods

The invention also provides methods for screening compounds to identify those (antagonists) which inhibit the binding of a Neisserial cell to an epithelial cell.

Potential antagonists for screening include small organic molecules, peptides, peptoids, polypeptides, lipids, metals, nucleotides, nucleosides, polyamines, antibodies, and derivatives thereof. Small organic molecules have a molecular weight between 50 and about 2,500 daltons, and most preferably in the range 200-800 daltons. Complex mixtures of substances, such as extracts containing natural products, compound libraries or the products of mixed combinatorial syntheses also contain potential antagonists.

Typically, App, ORF40 and/or NadA protein is incubated with an epithelial cell and a test compound, and the mixture is then tested to see if the interaction between the protein and the epithelial cell has been inhibited.

Inhibition will, of course, be determined relative to a standard (e.g. the native protein/cell interaction). Preferably, the standard is a control value measured in the absence of the test compound. It will be appreciated that the standard may have been determined before performing the method, or may be determined during or after the method has been performed. It may also be an absolute standard.

The protein, cell and compound may be mixed in any order.

For preferred high-throughput screening methods, all the biochemical steps for this assay are performed in a single solution in, for instance, a test tube or microtitre plate, and the test compounds are analysed initially at a single compound concentration. For the purposes of high throughput screening, the experimental conditions are adjusted to achieve a proportion of test compounds identified as "positive" compounds from amongst the total compounds screened.

Other methods which may be used include, for example, reverse two hybrid screening [e.g. Vidal & Endoh (1999) *TIBTECH* 17:374-381] in which the inhibition of the *Neisseria*:receptor interaction is reported as a failure to activate transcription.

The method may also simply involve incubating one or more test compound(s) with App, ORF40 and/or NadA and determining if they interact. Compounds that interact with the protein can then be tested for their ability to block an interaction between the protein and an epithelial cell.

The invention also provides a compound identified using the method. These can be used to treat or prevent Neisserial infection. The compound preferably has an affinity for App, ORF40 and/or NadA of at least $10^{-7}$ M e.g. $10^{-8}$ M, $10^{-9}$ M, $10^{-10}$ M or tighter.

The invention also provides a composition comprising (a) an *E. coli* bacterium which expresses App and/or ORF40 (and, optionally, NadA) and (b) an epithelial coil (e.g. a human epithelial cell).

Expression in Eater Membrane Vesicles (OMVs)

International patent application WO01/52885 discloses that the addition of further defined components to OMV vaccines significantly broadens their efficacy.

The preparation of OMVs from NmB is well-known in the art. Methods for obtaining suitable preparations are disclosed in, for instance: Claassen et al. [*Vaccine* (1996) 14:1001-1008]; Cartwright et al. [*Vaccine* (1999) 17:2612-2619]; Peeters et al. [*Vaccine* (1996) 14:1009-1015]; Fu et al. [*Biotechnology NY* (1995) 12:170-74]; Davies et al. [*J. Immunol. Meth.* (1990) 134:215-225]; Saunders et al. (*Infect. Immun.* (1999) 67:113-119); Draabick et al. [*Vaccine* (2000) 18:160-172]; Moreno et al. [*Infect. Immun.* (1985) 47:527-533]; Milagres et al. [*Infect. Immun.* (1994) 62:4419-4424]; Naess et al. [*Infect. Immun.* (1998) 66:959-965]; Rosengvist et al. [*Dev. Biol. Stand.* (1998) 92:323-333]; Haneberg et al. [*Infect. Immun.* (1998) 66:1334-41]; Andersen at al. [*Vaccine* (1997) 15:1225-34]; Bjune et al. [*Lancet* (1991) 338:1093-96] etc.

It has now been found that OMVs prepared from *E. coli* which express a heterologous *Neisseria* gene can give better results in standard immunogenicity tests than the antigens in purified form.

The invention therefore provides a method for preparing an OMV from a non-Neisserial host cell, characterised in that said cell expresses a gene encoding App, ORF40 or NadA protein.

The invention also provides (a) OMVs obtainable by this process, and (b) an outer membrane vesicle from a non-Neisserial host cell, characterised in that said cell expresses a gene encoding App, ORF40 or NadA protein.

The non-Neisserial host cell is preferably a bacterium and is most preferably *E. coli*.

More generally, the invention provides a method for preparing an OMV from a non-Neisserial host cell, characterised in that said cell expresses a gene encoding one or more of the following proteins:
(A) Even SEQ IDs 2-892 from WO99/24578;
(B) Even SEQ IDs 2-90 from WO99/36544;
(C) Even SEQ IDs 2-3020 from WO99/57280;
(D) Even SEQ IDS 3040-3114 from WO99/57280;
(E) SEQ IDs 3115-3241 from WO99/57280;
(F) The 2160 proteins NMB0001 to NMB2160 from Tettelin et al. [supra];
(G) A protein comprising the amino acid sequence of one or more of (A) to (F);
(H) A protein sharing sequence identity with the amino acid sequence of one or more of (A) to (F); and
(I) A protein comprising a fragment of one or more of (A) to (F).

Similarly, the invention also provides (a) OMVs obtainable by this process, and (b) an outer membrane vesicle from a non-Neisserial host cell, characterised in that said cell expresses a gene encoding one or more of proteins (A) to (I) described above.

The degree of 'sequence identity' referred to in (H) is preferably greater than 50% (eg. 60%, 70%, 80%, 90%, 95%, 99% or more) and this includes mutants and allelic variants The 'fragment' referred to in (I) should comprise at least n consecutive amino acids from one or more of (A) to (F) and, depending on the particular sequence, n is 7 or more (eg. 8, 10, 12, 14, 16, 18, 20, 25, 30, 35, 40, 50, 60, 70, 80, 90, 100 or more). Preferably the fragment comprises an epitope from one or more of (A) to CF). Preferred fragments are those disclosed in WO00/71574 and WO01/04316.

Preferred proteins for (A) to (F) are found in *N. meningitidis* serogroup B.

Mutants of App

Amino acid 267 of SEQ ID 650 of WO99/24578 (SEQ ID 32 herein) is a serine. App is believed to be a serine protease and this serine is believed to be a catalytic residue at its active site. It will be appreciated that standard sequence alignment techniques will reveal the amino acid corresponding to this Ser-267 for any other App sequence (e.g. Ser-260 in SEQ ID 652 of WO99/24578, Ser-267 in SEQ ID 654 etc.).

The invention provides a protein comprising the amino acid sequence of App, except that one or more of amino acids Ser-267, Asp-158 and His-115 (numbered according to SEQ ID 32) is/are mutated. The mutation may be a deletion, an insertion or, preferably, a substitution. The substitution is preferably with one of the 19 other naturally-occurring amino acids and is more preferably with glycine, alanine, tyrosine or lysine.

App is believed to cleaved at a site between amino acids 1063 and 1171 (numbered according to SEQ ID 32). It will be appreciated that standard sequence alignment techniques will reveal the amino acids corresponding to these two residues for any other App sequence.

The invention provides a protein comprising the amino acid sequence of App, except that one or more amino acid(s) between Ser-1064 and Arg-1171 (numbered according to SEQ ID 32) is mutated. The mutation may be a deletion, an insertion, truncation or, preferably, a substitution. The substitution is preferably with one of the 19 other naturally-occurring amino acids. The residue which is mutated is preferably S-1064, D-1065, K-1066, L-1067, G-1068, K-1069, A-1076, E-1071, A-1072, K-1073, K-1074, Q-1075, A-1076, E-1077, K-1078, D-2079, N-1080, A-1081, Q-1082, S-1083, L-1084, D-1085, A-1086, L-1087, I-1088, A-1089, A-1090, G-1091, R-1092, D-1093, A-1094, V-1095, E-1096, K-1097, T-1098, E-1099, S-100, V-1101, A-1102, E-1103, P-1104, A-1105, R-1106, Q-1107, A-1108, G-1109, G-1110, E-1111, N-1112, V-1113, G-1114, I-1115, M-1116, Q-1117, A-1118, E-1119, E-1120, E-1121, K-1122, K-1123, R-1124, V-1125, Q-1126, A-1127, D-1128, K-1129, D-1130, T-1131, A-1132, L-1133, A-1134, K-1135, Q-1136, R-1137, E-1138, 1139, E-1140, T-1141, R-1142, P-1143, A-1144, T-1145, T-1146, A-1147, F-1148, P-1149, R-1150, A-1151, R-1152, R-1153, A-1154, R-1155, R-1156, D-1157, L-1158, P-1159, Q-1160, L-1161, Q-1162, P-1163, Q-1164, P-1165, Q-1166, P-1167, Q-1168, P-1169, Q-1170 and/or R-1171.

App is alternatively believed to cleaved at amino acid 956 and/or amino acid 1178 (numbered according SEQ ID 32). It will be appreciated that standard sequence alignment techniques will reveal the amino acids corresponding to these residues for any other App sequence.

The invention provides a protein comprising the amino acid sequence of App, except that one or more of amino acids Phe-956, Asn-957, Ala-1178 & Asn-1179 (numbered according to SEQ ID 32) is mutated. The mutation may be a deletion, an insertion, truncation or, preferably, a substitution. The substitution is preferably with one of the 19 other naturally-occurring amino acids.

The invention also provides nucleic acid encoding these mutant proteins.

The invention also provides a method for producing this nucleic acid, comprising the steps of: (a) providing source nucleic acid encoding App, ORF40 or NadA, and (b) performing mutagenesis (e.g. site-directed mutagenesis) on said souses nucleic acid to provide nucleic acid encoding a mutant protein.

The invention provides mature App.

The invention also provides a protein comprising the amino acid sequence of a processed App, wherein said processed App does not comprise the C-terminus domain which is downstream of an autoproteloytic cleavage site in full-length App. Per example, based on SEQ ID 32 as full-length App, the invention provides SEQ IDs 33 to 36. C-terminus domains which may be removed during autoproteolysis are SEQ IDs 38 and 39.

The invention also provides a protein comprising the amino acid sequence of a processed App, wherein the C-terminus of said processed. App is Phe-956 (numbered according to SEQ ID 32). For example, the invention provides SEQ IDs 33 and 35. The amino acid corresponding to Phe-956 in other App sequences can be identified by standard sequence alignment techniques.

The invention also provides a protein comprising the amino acid sequence of a processed App, wherein the C-terminus of said processed App is Ala-1178 (numbered according to SEQ ID 32). For example, the invention provides SEQ IDs 34 and 36. The amino acid corresponding to Ala-1178 in other App sequences can be identified by standard sequence alignment techniques.

The invention also provides a protein comprising the amino acid sequence of a processed App, wherein said processed App does not comprise SEQ ID 37, 38 of 39.

The invention also provides a protein comprising an amino acid sequence selected from the group consisting of SEQ IDs 33, 34, 35, 36, 37, 38 & 39.

The invention also provides a protein comprising an amino acid sequence with at least p % sequence identity to one or more of SEQ IDs 33, 34, 35, 36, 37, 38 & 39. Depending on the particular sequence, the value of p is preferably 50 or more (e.g. 60, 70, 80, 90, 95, 99 or more). These proteins include homologs, orthologs, allelic variants and functional mutants. Typically, 50% identity or more between two proteins is considered to be an indication of functional equivalence. Identity between proteins is preferably determined by the Smith-Waterman homology search algorithm as implemented in the MPSRCH program (Oxford Molecular), using an affirm gap search with parameters gap open penalty=12 and gap extension penalty=1.

The invention further provides proteins comprising a fragment of one or more of SEQ IDs 33, 34, 35, 36, 37, 38 & 39. The fragments should comprise at least q consecutive amino acids from the sequences and, depending on the particular sequence, q is 7 or more (e.g. 8, 10, 12, 14, 16, 18, 20, 30, 40, 50, 60, 70, 80, 90, 100 or more). Preferably the fragments comprise one or more epitopes from the sequence.

The invention also provides nucleic acid encoding these proteins of the invention.

Alleles of NadA

The invention provides a protein comprising the amino acid sequence of one or more of SEQ IDs 1 to 14.

The invention also provides a protein comprising an amino acid sequence having at least x % sequence identity to one or more of SEQ IDs 1 to 14. The value of x is at least 50% (e.g. 60%, 70%, 80%, 85%, 90%, 95%, 97%, 98%, 99%, 99.5% or more). This includes variants e.g. allelic, variants, homologs, orthologs, paralogs, mutants, etc.

A preferred allele of NadA for use with the present invention is SEQ ID 3 (or SEQ ID 6).

The invention also provides a protein comprising a fragment of one or more of SEQ IDs 1 to 14. These should comprise at least n consecutive nucleotides from one or more of SEQ IDs 1 to 14, wherein n is 6 or more (e.g. 7, 8, 9, 10, 11, 12, 14, 15, 18, 20, 25, 30, 35, 40, 50, 60, 70, 80, 90, 100, 150, 200, 250, 300, 350 or more). The fragment may comprise a sequence which is common to SEQ IDs 1 to 14, or may comprise a sequence which is not common to SEQ IDs 1 to 14.

Preferred fragments comprise one or mare epitopes from SEQ IDs 1 to 14. Other preferred fragments are (a) the N-terminal leader peptides of SEQ IDs 1 to 14, (b) SEQ IDs 1 to 14, but without k N-terminal amino acid residue(s), wherein k is 1 or more (e.g. 2, 3, 4, 5, 6, 7, 8, 9, 10, 11, 12, 13, 14, 15, 20, 25, 30, 35, 40, 50 etc.), and (c) SEQ IDs 1 to 14, but without l C-terminal amino acid residue(s), wherein l is 1 or more (e.g. 2, 3, 4, 5, 6, 7, 8, 9, 10, 11, 12, 13, 14, 15, 20, 25, 30, 35, 40, 50 etc.). Preferred fragments fall within both (b) and (c) i.e. truncation at both C- and N-termini.

Preferred fragments within category (b) lack the N-terminal leader peptide. For SEQ IDs 1, 2, 3, 7, 9, 11 & 13 the value of k is thus 23; for SEQ IDs 4, 5, 6, 8, 10, 12 & 14 the value of k is 2.5. The leader peptide may be replaced with the leader peptide from another protein, by another protein (i.e. to form a fusion protein) or by an alternative N-terminus sequence to allow efficient expression.

Preferred fragments within category (c) lack the C-terminal membrane anchor. The value of l is the 54. Minor variants of this C-terminal deletion may be used (e.g. when l is 45, 46, 47, 48, 49, 50, 51, 52, 53, 55, 56, 57, 58, 59, 60, 61, 62, 63, 64, 65, 66).

Proteins with the N-terminus sequence MKH or MQH are preferred to those with N-terminus sequence MSM.

The protein of the invention may include the heptad sequence $(AA_1AA_2AA_3AA_4AA_5AA_6AA_7)_r$ wherein: $AA_1$ is Leu, Ile, Val or Met; each of $AA_2AA_3AA_4AA_5AA_6$ and $AA_7$ may independently be any amino acid; r is an integer of 1 or more (e.g. 1, 2, 3, 4, 5, 6, 7, 8, 9, 10 etc.). Where r is 2 or more, the meaning of each $AA_1AA_2AA_3AA_4AA_5AA_6$ and $AA_7$ may be the same or different in each of the r heptad repeats. The heptad(s) can form a leucine-zipper domain.

Proteins of the invention can be prepared in many ways e.g. by chemical synthesis (at least in part), by digesting longer polypeptides using proteases, by translation from RNA, by purification from cell culture (e.g. from recombinant expression), from the organism itself (e.g. isolation from prostate tissue), from a cell line source, etc.

Proteins of the invention can be prepared in various forms e.g. native, fusions, glycosylated, non-glycosylated, lipidated, non-lipidated etc.

The protein is preferably in the form of an oligomer.

Proteins of the invention may be attached or immobilised to a solid support.

Proteins of the invention may comprise a detectable label e.g. a radioactive label, a fluorescent label, or a biotin label. This is particularly useful in immunoassay techniques.

Proteins of the invention are preferably in isolated or substantially isolated form.

In general, the proteins of the invention are provided in a non-naturally occurring environment e.g. they are separated from their naturally-occurring environment. In certain embodiments, the subject protein is present in a composition that is enriched for the protein as compared to a control. As such, purified protein is provided, whereby purified is meant that the protein is present in a composition that is substantially free of other expressed proteins, where by substantially free is meant that less than 90%, usually less than 60% and more usually less than 50% of the composition is made up of other expressed proteins.

The term "protein" refers to amino acid polymers of any length. The polymer may be linear or branched, it comprise modified amino acids, and it may be interrupted by non-amino acids. The terms also encompass an amino acid polymer that has been modified naturally or by intervention; for example, disulfide bond formation, glycosylation lipidation, acetylation, phosphorylation, or any other manipulation or modification, such as conjugation with a labeling component. Also included within the definition are, for example proteins containing one or more analogs of an amino acid (including, for example, unnatural amino acids, etc.), as well as other modifications known in the art. Proteins can occur as single chains or associated chain.

Mutants can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. Variants can be designed so as to retain or have enhanced biological activity of a particular region of the polypeptide (e.g. a functional domain and/or, where the polypeptide is a member of a polypeptide family, a region associated with a consensus sequence). Selection of amino acid alterations for production of variants can be based upon the accessibility (interior vs. exterior) of the amino acid, the thermostability of the variant polypeptide, desired disulfide bridges, desired metal binding sites etc.

The invention also provides nucleic acid encoding a protein of the invention as defined above. The invention also provides nucleic acid comprising a fragment of at least n consecutive nucleotides from said nucleic acid, wherein n is 10 or more (e.g. 12, 14, 15, 18, 20, 25, 30, 35, 40, 50, 60, 70, 80, 90, 100, 150, 200, 500 or more).

Furthermore, the invention provides nucleic acid which can hybridise to nucleic acid encoding a protein of the invention, preferably under "high stringency" conditions (e.g. 65° C. in a 0.1×SSC, 0.5% SDS solution).

Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acids of the invention can be, prepared in many ways e.g. by chemical synthesis in whole or part, by digesting longer polynucleotides using nucleases (e.g. restriction enzymes), from genomic or cDNA libraries, from the bacterium itself, etc.

Nucleic acids of the invention can take various forms e.g. single-stranded, double-stranded, vectors, printers, probes, labelled, unlabelled, etc.

Nucleic acids of the invention are preferably in isolated or substantially isolated form.

The invention includes nucleic acid comprising sequences complementary to those described above e.g. for antisense or probing, or for use as primers.

The term "nucleic acid" includes DNA and RNA, and also their analogues, such as those containing modified backbones, and also peptide nucleic acids (PNA) etc.

Nucleic acid according to the invention may be labelled e.g. with a radioactive or fluorescent label. This is particularly useful where the nucleic acid is to be used in nucleic acid detection techniques e.g. Where the nuclei acid is a primer or as a probe for use in techniques such as PCR, LCR TMA, NASBA, etc.

The invention also provides vectors comprising nucleotide sequences of the invention (e.g. cloning or expression vectors, such as those suitable for nucleic acid immunisation) and host cells transformed with such vectors.

Immunisation

The invention provides an immunogenic composition comprising (a) a Neisserial NadA protein and/or (b) nucleic acid encoding NadA protein.

The invention also provides a method for raising an antibody response in a mammal, comprising administering an immunogenic composition of the invention to the mammal. The antibody response is preferably a protective antibody response. The protective antibody preferably blocks the attachment of NadA and/or App to epithelial cells.

The invention also provides a method for protecting a mammal against a Neisserial intention, comprising administering to the mammal an immunogenic composition of the invention.

The invention also provides Neisserial NadA protein for use as a medicament.

The invention also provides the use of a NadA protein in the manufacture of a medicament for preventing Neisserial infection in a mammal The invention also provides the use of nucleic acid encoding a NadA protein in the manufacture of a medicament for preventing Neisserial infection in a mammal.

The Mammal is preferably a human. The human may be an adult or, preferably, a child.

The NadA protein is preferably a N. meningitidis NadA. It preferably comprises the amino acid sequence of one or more of SEQ IDs 1 to 14, or an amino acid sequence having sequence identity thereto or comprising a fragment thereof (see above). The NadA protein is preferably in the form of an oligomer (e.g. a timer, trimer, tetramer or higher). Within SEQ IDs 1 to 14, SEQ IDs 1 to 12 are preferred, as antibodies against these NadA proteins are bactericidal across the various hypervirulent alleles. Where an immune response against a non-hypervirulent NadA$^+$ strain is desired, however, SEQ IDs 13 & 14 are preferred. Of course, NadA mixtures are also possible, particularly mixtures containing more than one NadA allele.

Immunogenic compositions of the invention may be used therapeutically (i.e. to treat an existing infection) or prophylactically (i.e. to prevent future infection).

The uses and methods of the invention are particularly useful for treating/protecting against infections of *Neisseria meningitidis*, including serogroups A, B, and C. They are particularly useful against strains of *N. meningitidis* from hypervirulent lineages ET-5, EY-37 and cluster A4.

The uses and methods are particularly useful for preventing/treating diseases including, but not limited to, meningitis (particularly bacterial meningitis) and bacteremia.

Efficacy of therapeutic treatment can be tested by monitoring Neisserial infection after administration of the composition of the invention. Efficacy of prophylactic treatment can be tested by monitoring immune responses against NadA after administration of the composition.

The composition of the invention may additionally comprise an antigen which, when administered to a mammal, elicits an immune response which is protective against a lineage III strain of *N. meningitidis*.

Compositions of the invention will generally be administered directly to a patient Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, or pulmonary administration.

The invention may be used to elicit systemic and/or mucosal immunity.

Dosage treatment can be a single dose schedule or a multiple dose schedule.

The immunogenic composition of the invention will generally include a pharmaceutically acceptable carrier, which can be any substance that does not itself induce the production of antibodies harmful to the patient receiving the composition, and which can be administered without undue toxicity. Suitable carriers can be large, slowly-metabolised macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers can include liquids such as water, saline, glycerol and ethanol. Auxiliary substances, such as wetting or emulsifying agents, pH buffering substances, and the like, can also be present in such vehicles. Liposomes are suitable carriers. A thorough discussion of pharmaceutical carriers is available in Gennaro (2000) *Remington: The Science and Practice of Pharmacy*. 20th edition, ISBN: 0683306472.

Neisserial infections affect various areas of the body and so the compositions of die invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a line powder or a spray. Tire composition may be prepared as a suppository or pessary. The composition may be prepared for nasal, aural or ocular administration e.g. as drops.

The composition is preferably sterile. It is preferably pyrogen-free. It is preferably buffered e.g. at between pH 6 and pH 8, generally around pH 7.

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

The immunogenic composition may include an adjuvant. Preferred adjuvants to enhance effectiveness of the composition include, but are not limited to (A) aluminium compounds (e.g. an aluminium hydroxide such as oxyhydroxide, or an aluminium phosphate such as hydroxyphosphate or orthophosphate, aluminium sulphate etc.), or mixtures of different aluminium compounds, with the compounds taking any suitable form (e.g. gel, crystalline, amorphous etc.), and with adsorption being preferred; (B) MP59 (5% Squalene, 0.5% Tween 80, and 0.5% Span 85, formulated into submicron particles using a microfluidizer); (C) liposomes; (D) ISCOMs, which may be devoid of additional detergent; (F) SAF, containing 10% Squalane, 0.4% Tween 80, 5% pluronic-block polymer L121, and thr-MDP, either microfluidized into a submicron emulsion or vortexed to generate a larger particle size emulsion; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21, also known as Stimulon™; (H) chitosan; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc.; (K) microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone etc.); (L) monophosphoryl lipid A (MPL) or 3-O-deacylated MPL (3dMPL); (M) combinations of 3dMPL with, for example, QS21 and/or oil-in-water emulsions; (N) oligonucleotides comprising CpG motifs i.e. containing at least one CG dinucleotide, with 5-methylcytosine optionally being used in place of cytosine; (O) a polyoxyethylene ether or a polyoxyethylene ester; (P) a polyoxyethylene sorbitan ester surfactant in combination with an octoxynol or a polyoxyethylene alkyl ether or ester surfactant in combination with at least one additional nonionic surfactant arch as an octoxynol; (Q) an immunostimulatory oligonucleotide (e.g., a CpG oligonucleotide) and a saponin; (R) an immunostimulant and a particle of metal salt; (S) a saponin and an oil-in-water emulsion; (T) a saponin (e.g. QS21)+3dMPL+IL-12 (optionally+a sterol); (U) *E. coli* heat-labile enterotoxin ("LT"), or detoxified mutants thereof, such as the K63 or R72 mutants; (V) cholera toxin ("CT"), or detoxified mutants thereof; (W) microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid) such as poly(lactide-co-glycolide), a polyhydroxybutyric acid, a polyorthoester, a polyanhydride, a polycaprolactone etc.); and (X) other substances that act as immunostimulating agents to enhance the effectiveness of the composition. Aluminium salts (aluminium phosphates and particularly hydroxyphosphates, and/or hydroxides and particularly oxyhydroxide) and MF59 are preferred adjuvants for parenteral immunisation. Toxin mutants are preferred mucosal adjuvants.

Muramyl peptides include N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

Compositions of the invention may comprise antigens (e.g. protective antigens against *N. meningitidis* or against other organisms) in addition to NadA e.g. DTP antigens, Hib antigen etc.

Immunogenic compositions of the invention may be used therapeutically (i.e. to treat an existing infection) or prophylactically (i.e. to prevent future infection). Therapeutic immunisation is particularly useful for treating *Candida* infection in immunocompromised subjects.

As an alternative to using proteins antigens in the immunogenic compositions of the invention, nucleic acid (preferably DNA e.g. in the form of a plasmid) encoding the antigen may be used.

Disclaimers

The invention preferably excludes: (a) amino acid and nucleic acid sequences available in public sequence databases (e.g. GenBank or GENESEQ) prior to 26 Jul. 2002 and, more preferably, prior to 27 Jul. 2001; (b) amino acid and nucleic acid sequences disclosed in patent applications having a filing date or, where applicable, a priority date prior to 26 Jul. 2002 and, more preferably, prior to 27 Jul. 2001. In particular, SEQ ID entries in the following patent applications may be excluded WO99/24578; WO99/36544; WO99/57280; WO00/22430; WO00/66741; WO00/66791; WO00/71574; WO00/71725; WO01/04316; WO01/31019; WO01/37863; WO01/38350; WO01/52885; WO01/64920; WO01/64922.

DEFINITIONS

The term "comprising" means "including" as well as "consisting" e.g. a composition "comprising" X may consist exclusively of X or may include something additional e.g. X+Y.

BRIEF DESCRIPTION OF DRAWINGS

FIG. 1A-FIG. 1C shows expression data for ORF40. FIG. 1A shows a whole cell Western blot for ORF40. FIG. 1B shows a whole cell immunoblot for ORF40. FIG. 1C shows FACS analysis of ORF40.

FIG. 2A-FIG. 2C shows expression data for App. FIG. 2A shows a Western blot for App. FIG. 2B shows a whole cell immunoblot for App. FIG. 2C shows FACS analysis of App.

FIG. 3A-FIG. 3C shows expression data for NadA. FIG. 3A shows SDS-PAGE analysis of NadA. FIG. 3B shows a whole cell immunoblot for NadA. FIG. 3C shows FACS analysis of NadA.

FIG. 4A-FIG. 4D show FACS analysis data. Adhesion of cells expressing ORF40 (FIG. 4A), App (FIG. 4B), NadA (FIG. 4C), or an HSF positive control (FIG. 4D) to human epithelial cells is shown.

FIG. 5A-FIG. 5D show FACS analysis data. Adhesion of ORF40 protein (FIG. 5A), App protein (FIG. 5B), NadA protein (FIG. 5C), or a GNA2132 negative control protein (FIG. 5D) to human epithelial cells is shown.

FIG. 6A-FIG. 6B shows binding of proteins to human epithelial cells. FIG. 6A shows binding of ORF40 (♦), App (•), NadA (♦) and GNA2132 (■) to human epithelial cells as a function of protein concentration. FIG. 6B shows binding of NadA (♦) and GNA2132 (■) to human epithelial cells as a function of protein concentration.

FIG. 9A-FIG. 9C show an alignment of NadA alleles 1 to 3. FIG. 9A shows a sequence alignment of NadA alleles 1 to 3 (SEQ ID NOS: 4-6) starting with the first Met residue in the open reading frame. FIG. 9B shows an alignment of NadA alleles 1 to 3 (SEQ ID NOS: 1-3) starting with the second Met residue in the open reading frame. FIG. 9C shows an alignment of allele C (SEQ ID NO: 14) with NadA alleles 1 to 3 (SEQ NOs: 4-6).

FIG. 12A shows analysis of sequences upstream and downstream of NadA (SEQ ID NO: 41). FIG. 12B shows alignment of the NadA locus in the MC58 and Z2491 strains (SEQ ID NO: 42).

FIG. 15A-FIG. 15B show variation of NadA expression with culture time. FIG. 15A shows a Western blot of NadA expression over time in the MC58 strain (left panel) with a corresponding analysis of strain growth rate (right panel). FIG. 15B shows a Western blot of NadA expression over time in the 2996 strain (left panel) with a corresponding analysis of strain growth rate (right panel).

FIG. 17A-FIG. 17D show immunofluorescence results obtained using anti-NadA against Chang cells (FIG. 17A, FIG. 17B, and FIG. 17C) or HeLa cells (FIG. 17D).

(FIG. 18A) or 4° C. (FIG. 18B).

FIG. 20A-FIG. 20C show immunofluorescence results obtained using monocytes. FIG. 20A shows NadA binding to monocytes. FIG. 20B shows NadA alone with no staining antibody. FIG. 20C shows NadA stained with pre-immune serum.

FIG. 34A and FIG. 34B show pET-App transformants incubated with epithelial cells. FIG. 34C and FIG. 34D show S267A mutants incubated with epithelial cells. FIG. 34E and FIG. 34F show Appβ transformants incubated with epithelial cells. FIG. 34G shows untransformed controls incubated with epithelial cells.

MODES FOR CARRYING OUT THE INVENTION

NadA Homology

NadA shows homology to (a) YadA of enteropathogenic *Yersinia*, a non-pilus associated adhesin implicated in virulence [Cornelis (1998) *Microbiol. Mol. Biol. Rev.* 62:1315-1352.] and (b) UspA2 of *Moraxella catarrhalis*, a protein involved in serum resistance and a protective antigen [Chen et al. (1999) *Infect. Immun.* 67:1310-1316]. Sequence similarity is mainly clustered in the carboxyl terminal region (56-63% identity in the last 70 amino acids). Outside this region the level of identity drops to 23-25%.

YadA and UspA2 have been identified as adhesins [Hoiczyk et al. (2000) *EMBO J* 19:5989-5999]. Both proteins form very stable and difficult-to-dissociate high molecular weight oligomers (150-200 kDa) anchored to the outer membrane. NadA has also been found to form very stable high molecular weight aggregates on the outer membrane of meningococcus.

Figure 11:
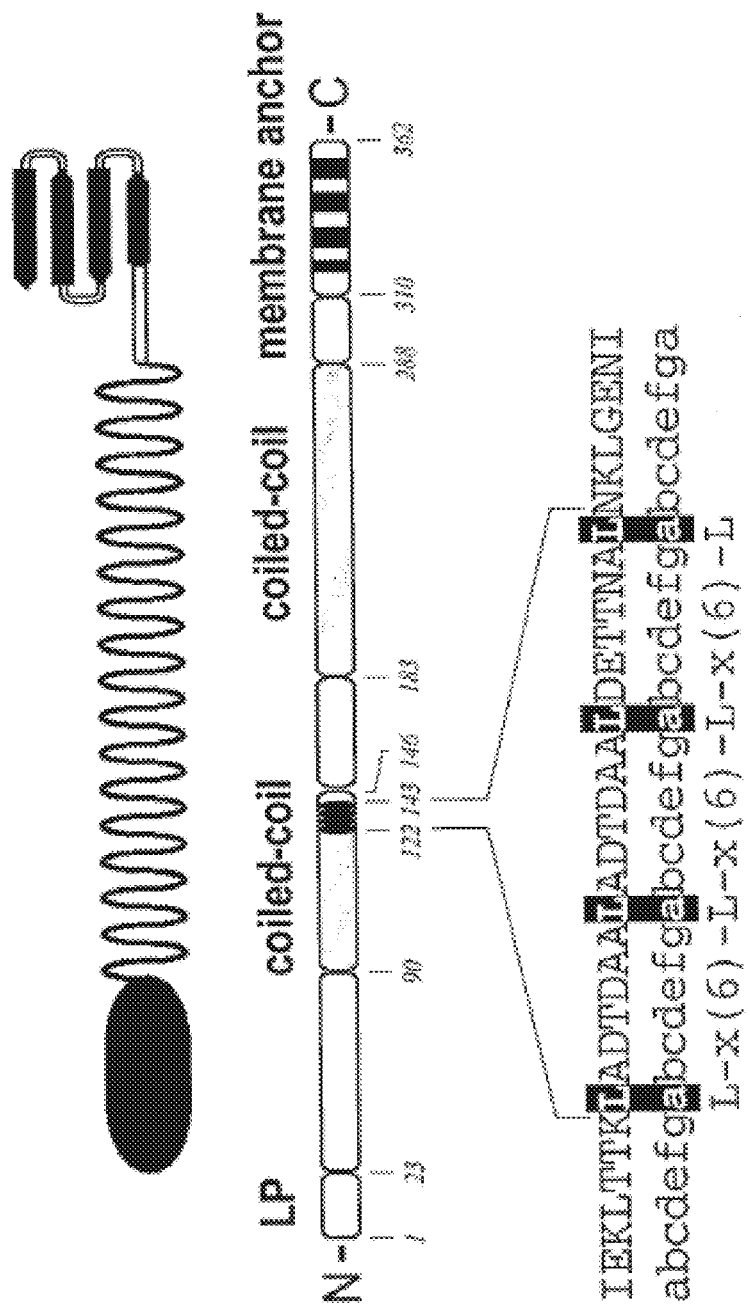
FIG. 11 shows predicted secondary structure for NadA, (SEQ ID NO: 40) (top) and (SEQ ID NO: 52) (bottom).

The amino acid sequence of NadA was analysed [Nielsen et al. (1997) *Protein Engineering* 10:1-6; Levin & Garner (1988) *Biochim. Biophys. Acta* 955:283-295; Berger et al. (1995) *PNAS USA* 92:8259-8263; Bornberg-Bauer et al. (1998) *Nucleic Acids Res.* 26:2740-2746]. Secondary structure analysis is shown in FIG. 11. The globular N-terminus and amphipathic C-terminus are indicated, as are the positions of the leader peptide (LP) and a membrane anchor. The carboxyl-terminal region (aa 310-362) has a predicted amphipatic β-structure (β-strands shown in black) and a terminal aromatic amino acid, which are typical features of outer membrane anchoring domains. The amino terminal region (aa 23-90) has no defined secondary structure, but the rest of the protein has mainly α-helix propensity (84.6%). Within this region, residues 90-146 and 183-288 have high probability of forming coiled coils. In addition, residues 122-143 contain four leucine residues in the "a" positions of the heptad repeats (L-x(6)-L-x(6)-L-x(6)-L) that may form a leucine zipper domain (•••). It is known that both coiled coils and leucine zipper sequences are involved in dimerization and may mediate oligomerisation of monomers via association of two or more alpha helices.

Even though primary structure similarity between NadA, YadA and UspA2 is clustered at the C-terminus, therefore, the overall similarity between the three proteins is conserved at secondary structure level. Putative leucine zippers are present in both NadA and UspA2. NadA, YadA and UspA2 have a carboxyl terminal membrane anchor made by four amphipathic β-strands and an internal α-helical region with propensity to form coiled-coils. In YadA and UspA2 these α-helices have been shown to form coiled-coils regions, which mediate oligomerisation of monomers [Hoiczyk et al. (2000) *EMBO J* 19:5989-5999; Cope et al. (1999) *J. Bacteriol.* 181:4026-4034].

The absence of cysteine residues in the mature forms of NadA is another feature shared with its homologues.

The Genomic Environment of NadA

Figures 12A, 12B:
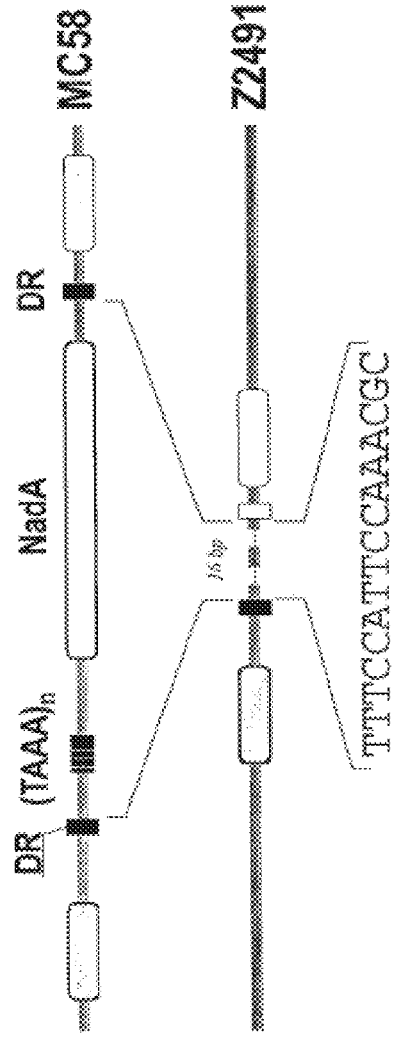
FIG. 12A-FIG. 12B show NadA sequence information.

The 1086 bp nadA coding region is flanked at the 3' end by a terminator sequence while at the 5' end (FIG. 12A) it shows a putative ribosome-binding site (RBS; 5'-AAGG-3') and a putative promoter region located 8 and 47 base pairs, respectively, upstream the ATG start codon.

130 bp upstream the coding region are nine repeats of the tetranucleotide TAAA (shaded black in FIG. 12A), preceded by a second putative promoter with −10 and −35 regions. Because of the presence of the TAAA repeats, the gene had been listed as one of those that may undergo phase variation, even though the repeats are not in the coding region [Tettelin et al.]. The homologous gene UspA2 has a tetranucleotide repeat (AGAT) located in the same position as in nadA, which varies in different strains [Cope et al. (1999) *J. Bacteriol.* 181:4026-4034].

The G+C content of the nadA gene and its upstream region is lower than average (45% against an average of the rest of the genome, 51.5%), suggesting acquisition of the gene by horizontal transfer.

The NadA gene and its upstream region are not present in the published sequence of the genome of serogroup A, strain Z2491 [Parkhill et al. (2000) *Nature* 404:502-506]. In the MenA genome, a short sequence of 16 nucleotides with no homologies in the database, replaces the nadA gene (FIG. 12B), whereas the upstream and downstream genes (nmb1993 and nmb1995) are well conserved (91% and 97% identity). Analysis of the sequences immediately adjacent to the nadA region and absent in the Z2491 serogroup A strain shows that the segment is flanked by the TCAGAC direct repeats. This may indicate a mechanism of recombination. In the A strain the stretch of 16 nucleotides has a disrupted pair of TCAGAC repeats flanking it.

Variation in NadA Genotype

Given the difference in nadA expression between serotypes A and B, 175 different strains of *N. meningitidis* were chosen for analysis −150 isolates representative of the five disease-associated serogroups (A, B, C, Y and W-135) and 25 strains isolated from healthy carriers. The analysis also included one strain each of *N. goriorrhoeae. N. cinerea* and *N. lactamica*.

Bacteria were grown overnight at 37° C. in a humidified atmosphere of 5% $CO_2$ in air on gonococcus (GC) medium agar (Difco) supplemented with Kellogg's supplement solution (0.22 M D-glucose, 0.03 M L-glutamine, 0.001 M ferric nitrate, and 0.02 M cocarboxylase) (Sigma-Aldrich Chemical Co, St. Louis, Mo.) as previously described [Knapp et al. (1988) *Antimicrob. Agents Chemother.* 32:765-767; Roberts et al. (1977) *J. Bacteriol.* 131:557-563]. One loopful of bacteria was dissolved in 500 µl of PBS and chromosomal DNA was prepared as previously described [Tinsley et al. (1996) *PNAS USA* 93:11109-11114].

The bacteria were screened by PCR and/or dot blot hybridization.

PCR amplification of the nadA genes was performed on 10 ng of chromosomal DNA using primers, mapping 350 nt upstream and downstream from the coding region (forward primer: SEQ ID 16; reverse primer: SEQ ID 17), and Platinum Hifi Taq Polymerase (GIBCO). PCR conditions were: 30 cycles of denaturation at 95° C. for 30 s, annealing at 60° C. for 30 s, and extension at 68° C. for 1 min. PCR products were analysed on 1% agarose gel and the sizes were determined using a molecular weight marker 1 Kb Plus DNA Ladder (GIBCO). The amplified fragments were purified on a Qiaquick column (Qiagen) and then automated cyclo-sequenced (Applied Biosystems model 377) by primer walking on both strands of the amplified fragment.

For dot blotting, the probe used was the whole nadA gene, as amplified from 2996 strain and labelled with digoxigenin using the Roche DIG High-Prime DNA Labelling and Detection Kit. 10 µl aliquot of cell suspension of each strain were boiled for 10 min. and spotted on nylon membrane (Boehringer). The membranes underwent cross-linking of DNA by 2' exposure to UV light and other standard procedures for preparation and signal detection as reported by the manufacturer.

The nadA gene was absent, in *N. gonorrhoeae* and in the commensal species *N. lactamica* and *N. cinerea*. In *N. meningitidis*, however, 47% of isolated were positive for its presence.

Figure 13:
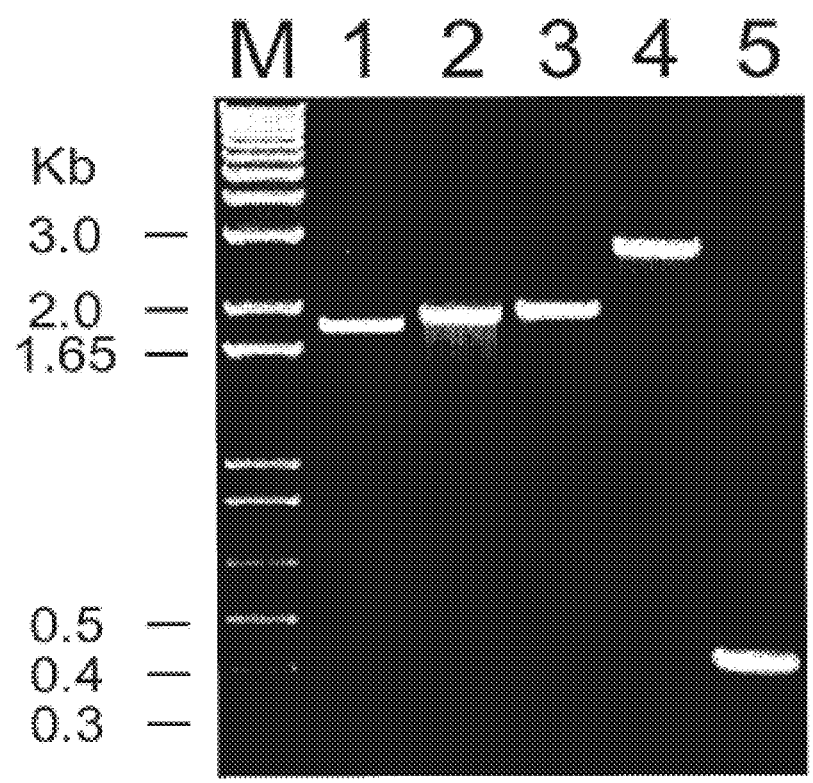
FIG. 13 shows PCR analysis of NadA expression in different strains of N. meningitidis.

PCR generated (FIG. 13) a product of 1800 bp in $NadA^+$ strains MC58 (lane 1), 90/18311 (lane 2) and 2996 (lane 3). It gave a product a 400 bp in $NadA^-$ strain Z2491 and NG3/88 (lane 5), Some strains (e.g. 93/4286, C4678, 2022, ISS1113) gave a PCR product of 2500 bp (lane 4: L93/4286).

The presence/absence of NadA in *N. meningitidis* was correlated with strain lineage. Strains isolated from invasive meningococcal disease have been classified by multilocus enzyme electrophoresis (MLEE) into a small number of hypervirulent lineages: Electrophoretic Types ET37, ET5, cluster A4, lineage III, subgroups I, III and IV-1 [Achtman (1995) *Global epidemiology of meningococcal disease.* In *Meningococcal disease* (Cartwright, ed), John Wiley and Sons, Chichester, England. 159-175; Caugant (1998) *APMIS* 106:505-25]. Recently, a sequence-based classification, multilocus sequence typing (MLST), has been introduced, which classifies the above strains into Sequence Types ST11, ST32, ST8, ST41, ST1, ST5, ST4, respectively [Malden et al. (1998) *PNAS USA* 95:3140-3145]. Strains isolated from healthy carriers fall into many different ET and ST types.

The nadA gene was present in 51 out of 53 strains (96%) of the hypervirulent lineages ET-5, ET-37 and cluster A4, whereas it was absent in all the tested lineage III strains. Seven of the 25 carrier strains tested were positive. Most of the serogroup C strains tested were positive even if not belonging to hypervirulent lineages. The same was true for the serogroup B strains with serotype 2a and 2b. For serogroup A, one strain belonging to subgroup III was positive where the other two strains belonging to subgroup IV-1 were negative.

Lineage III has only recently been introduced in Europe and USA and the geographic segregation in New Zealand for many years could have impaired its ability to acquire novel genes. For instance, mutations may have occurred in the surrounding chromosomal regions preventing Lineage III from further recombination events. Mother possible explanation is that ET-5, ET-37 and Cluster A4 strains need nadA to achieve peak fitness whereas Lineage III isolates cannot derive any significant benefit from nadA insertion, thus undergoing a negative selection.

NadA is thus over-represented in three hypervirulent *N. meningitidis* lineages. It appears to be a foreign gene present in a subset of hypervirulent strains.

NadA Alleles

As PCR products were differently sized (FIG. 13) and most of the $NadA^+$ strains could be grouped in three different sizes, genes were sequenced for 36 strains representative of each sizes: 26 positive strains, 4 strains with a long PCR product, and 6 $NadA^-$ strains.

In the negative strains, a 16 bp sequence was found which was identical to the sequence present in the published serogroup A genuine sequence.

Analysis of the sequence of the four long PCR product strains revealed an interruption by a single copy of IS1301, interrupting the protein after 162 amino acids with a stop codon. The insertion site was identical in all four strains, but the orientation of IS1301 differed, indicating independent events. The target consensus for IS1301, 5'-AY<u>TAG</u>-3' was found within the NadA gene at nucleotide 472, generated by, an A->G mutation, and was accompanied by a TA duplication.

Figure 10:
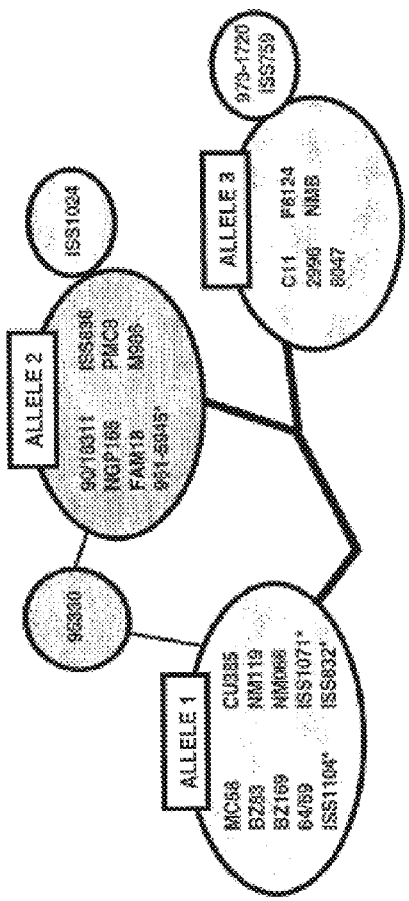
FIG. 10 shows the relationship of NadA alleles 1 to 3 (SEQ ID NOs: 4-6).

In $nadA^+$ strains gene size ranged from 1086 to 1215 bp, with consequent variation of the amino acid sequences of the encoded proteins flew 362 to 405 amino acids. It was possible to cluster 22 of the 26 NadA genes into three well-defined alleles (FIGS. 9 & 10; Table I). The sequence of the gene within each allele is identical and overall identity between the alleles ranges from 96% to 99%. This level of conservation is surprising and suggests weak selective pressure and/or a very recent acquisition of the nadA gene. The latter possibility is consistent with the low G+C content of the genome in this region (see above).

| Allele | Found in strains | SEQ IDs |
|---|---|---|
| 1 | MC58, BZ83, BZ169, NM066, NM119, CU385, ISS832, ISS1071, ISS1104 | 1, 4 |
| 2 | 90/18311, NGP165, PMC8, M986, ISS838 and 961-5945 | 2, 5 |
| 3 | C11, 973-1720, ISS759, F6124, 2996, 8047, NMB | 3, 6 |

The sequences shown in FIG. 9A assume that the N-terminus amino acid is the first Met in the open reading frame (SEQ IDs 4 to 6), but the second Met (residue 3 in SEQ IDs 4 to 6) has a better positioned Shine-Dalgarno motif (FIG. 9B). Sequences starting from the second Met codon are thus preferred (SEQ IDs 1 to 3).

Allele 1 codes for a protein of 362-amino acids (SEQ ID 1) and includes strain MC58 and all the ET-5 positive strains sequenced. The other five strains belonging to allele 1 were very recent isolates and they have not been FE-typed yet, although serotype and serosubtype classification (B15:P1.7 and B:4:P1.15) of these strains suggests affiliation of these strains to the ET-5 complex.

Allele 2 codes for a protein of 398 amino acids (SEQ ID 2) resulting from the addition of 2 as after residue 268 (numbering according to SEQ ID 1), addition of 41 as after residue 271, and deletion of 7 an after residue 122, resulting in the deletion of the first heptad repeat of the leucine zipper domain. Leucine residues at a fixed spacing of seven residues commonly identify leucine zippers. One leucine in the repeats has frequently been replaced mostly by Met, Val or Ile. In this case allele 2 could use the Ile upstream or downstream to form the leucine zipper motif.

Allele 3 codes for a protein of 405 amino acids (SEQ ID 3) and, like allele 2, contains 43 extra amino acids at residues 268 and 271 but differs from allele 2 by not having the 7aa deletion after residue 122. Allele 3 is found in serogroup A, B and C strains.

The remaining 4/26 positive strains (ISS1024, ISS759, 973-1720, 95330, marked with in Table 1) contain minor variants of alleles 1 to 3:

Serogroup C strain ISS1024 has a variant of allele 2 with a single heptad repeat deletion at residues 229-235 (SEQ IDs 7/8), This sequence was originally classified as a fourth allele but has been re-classified as a variant of allele 2. Allele 2 is thus found in all ET-37 strains, one strain of cluster A4 and three additional non-ET-typed serogroup C strains.

Serogroup C strains ISS759 and 973-1720 both contain a variant of allele 3 with a single amino acid mutation in the leader peptide (SEQ IDs 9/10) resulting from a single nucleotide mutation. Among all allele 3 strains, only 973-1720 belongs to a hypervirulent strain (cluster A4).

Serogroup B strain 95330 contains a recombinant (chimera) of alleles 1 and 2 (SEQ IDs 11/12), with nadA being a fusion between the N-terminal portion of allele 2 and the C-terminal segment of allele 1. The putative site of recombination is located approximately between residues 141 and 265 of the protein.

All insertions and deletions happen in the coiled-coil region and involve 7 or 41 amino acids which, representing 2 or 6 turns of the α-helix, allows for variations in length of the coiled coil region without disturbing the overall structure. Furthermore, the deletion in ISS1024 results in the loss of the first heptad repeat of the leucine zipper domain but does not destroy the domain because leucine residues at a fixed spacing of seven residues eau be replaced mostly by Met, Val or Ile. In this case allele 2 could use the Ile upstream or downstream to form the leucine zipper motif (FIG. 11).

Any of these various NadA sequences and alleles can be used in accordance with the invention.

When sequence analysis was extended to the putative promoter and terminator regions (50 bp upstream, 350 bp downstream), variations were found only in the in the 5' region. Three Italian strains (ISS1071, ISS832 and ISS1104) differed for a single base mutation while in strain 961-5945 there was a 7 base differences (indicated with * in FIG. 10). Variations were also found in the 5' regions where the TAAA tetranucleotide was repeated from 4 to 12 times in different strains (Table 1). The number of repeats was variable also within each allele (Table 1).

Further work was performed on carrier strains isolated from healthy individuals by oro-pharyngeal swab. Some strains, even if described as carriers, belong to hypervirulent clusters, and NadA was found in all such carrier strains as described above (i.e. allele 1 in the ET-5 strains and allele 2 in the ET-37 strains).

NadA was also found in five carrier strains (NGE28, 65/96, 149/96, 16269, 16282) which do not belong to a hypervirulent cluster. These five strains shared a sequence (SEQ IDs 13 & 14) which was not found in strains isolated from patients. This allele is referred to as 'allele C' (carrier).

Figure 9C:
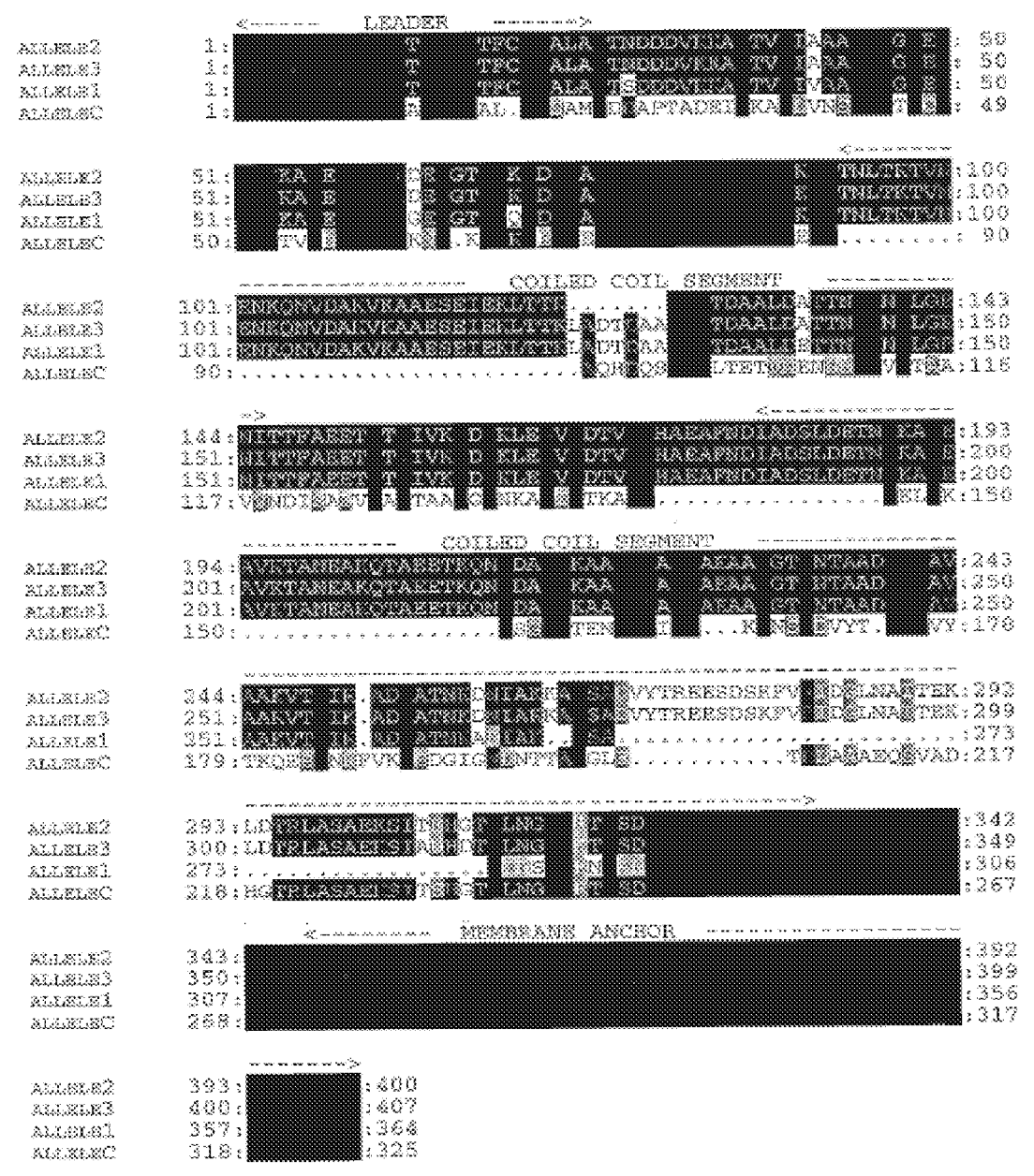

An alignment of allele C with alleles 1 to 3 is shown in FIG. 9C. Disruption in the coiled-coil segments of the protein is evident.

Unlike alleles 1 to 3, allele C protein does not readily form a high molecular aggregate when expressed in *E. coli*. Like alleles 1 to 3, however, allele C is exposed on the surface of *N. meningitidis*, because it is a target for bactericidal antibody raised against itself. However, these antibodies are not bactericidal against strains carrying alleles 1 to 3; similarly, antibodies raised against alleles 1 to 3 are not bactericidal against allele C strains.

NadA Oligomers on the Cell Surface

WO01/64922 reports that NadA forms oligomeric structures. To study NadA oligomers in more detail, whole cell lysates of *N. meningitidis* were probed by Western blot.

Bacterial colonies [strains MC58 (allele 1), 90/18311 (allele 2), 2996 (allele 3), L93/4286 (IS1301 insertion) and NG3/88 (nadA$^-$)] were grown to stationary phase in GC broth supplemented with 0.3% glucose. Samples, were taken at different times, pelleted by centrifugation at 3000×g for 10 min, and resuspended in PBS and thawed/frozen up to bacterial lysis. Equal amounts of proteins were subjected to SDS-PAGE on 12.5% Polyaerylamide gels and electrotransferred onto nitrocellulose membranes.

To prepare anti-NadA polyclonal serum, recombinant NadA was expressed and purified. Sequences encoding the three nadA alleles (allele 1: as 24-362; allele 2: as 24-343; allele 3: as 24-350), were amplified by PCR chromosomal DNA and cloned into pET21b+ vector (Novagen). The plasmids were transformed in *E. coli* BL21 (DE3) to express the proteins as C-terminal histidine fusions. Protein expression was induced at 30° C. by adding 1 mM IPTG at $OD_{600nm}$ 0.3 and growing the bacteria for an additional 3 h; expression was evaluated by SDS-PAGE. Recombinant lesion proteins were purified by affinity chromatography on $Ni^{2+}$-conjugated chelating fast-flow Sepharose 4B resin, 20 µg of purified protein was used to immunise six-week-old CD1 female mice (4 to 6 per group). Proteins were given intraperitoneally, with complete Freund's adjuvant (CFA) for the first dose and incomplete Freund's adjuvant (IFA) for the second (day 21) and third (day 35) booster doses. Bleed out samples were taken on day 49 and used for the serological analysis.

Figure 14:
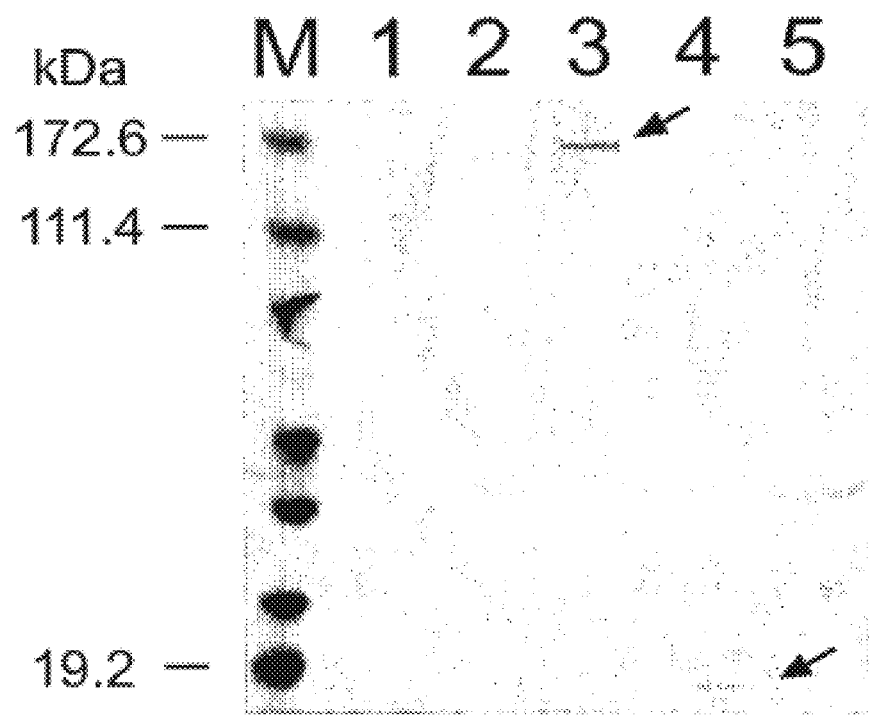
FIG. 14 shows immunoblot analysis of NadA expression in different strains of N. meningitidis.

The blots showed a high molecular weight reactive band in strains MC58 (FIG. 14, lane 1), 90/18311 (lane 2) and 2996 (lane 3). The band was absent in strain NG3/88 (lane 5). Boiling of the sample buffer up to 40 minutes did not change the pattern. The different size of the proteins was consistent with the size of the alleles. Given the expected size ranging from 35 to 40 kDa of monomeric proteins, the high MW of the observed band, could be explained by the presence of an oligomeric form of NadA. This possibility is supported by the fact that in a strain containing the IS1301 insertion, coding for a shorter protein of 162 amino acids and lacking most of the coiled-coil region, the high MW reactive band was absent and replaced by a band of 14.5 kDa (FIG. 14, lane 4), consistent with the predicted molecular weight of the processed monomeric protein.

Although the oligomeric protein was found in all strains containing a functional gene, expression levels varied from strain to strain (Table I). Moreover, the amount of NadA protein varied within the same strain during growth.

Four different strains (MC58, 2996, C11, F6124), chosen as representative of diverse overall NadA expression level, were followed during growth up to stationary phase. FIG. 15 shows growth of two of the tested strains (15A: MC58, with low NadA expression; 15B: 2996, with high NadA expression), with the curve showing $OD_{600}$. Western blots of samples taken at each point of the $OD_{600}$ growth curve showed that the NadA band was barely visible at the beginning of the growth and became more intense during growth, up to its maximum, at stationary phase. Alt strains analysed showed the same growth-phase dependent behaviour.

High MW NadA was also seen in western blots of outer membrane vesicles, consistent with NadA being anchored to the outer membrane.

Figure 16:
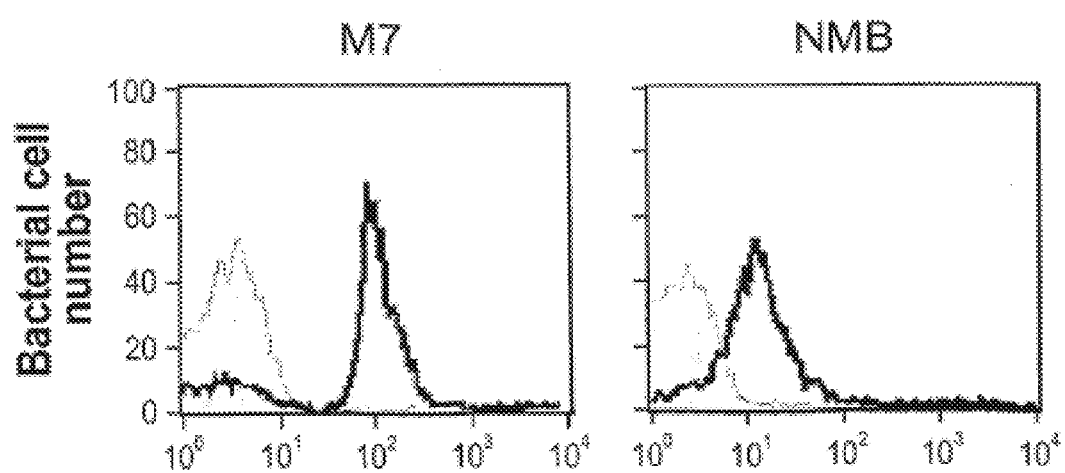
FIG. 16 shows NadA FACS of isogenic capsulated (NMB) and non-capsulated (M7) N. meningitidis cells.

Similarly, FACS analysis on live bacteria during log-phase growth showed that NadA was available for antibody binding on the surface of the FACS intensity in a strain with a polysaccharide capsule (strain NMB) was reduced 1 log in comparison to an isogenic non-encapsulated mutant strain (M7), but the protein was surface-exposed and available for binding in both strains (FIG. 16).

NadA forms surface-exposed oligomers, which are stable to heat, SDS and reduction with β-mercaptoethanol. As the mature form of the lacks cysteine residues, disulphide bond formation cannot be involved in this phenomenon; rather this is consistent with the predicted coiled-coil structure and the presence of leucine zipper motifs that might mediate inter-molecular interactions between monomers [Lupas (1996) *Trends Biochm. Sci.* 21:375-382; O'Shea et al. (1991) *Science* 254:539-544]. The size of the oligomers is approximately 170 kDa, suggesting a tetrameric structure [WO01/64922]. However, a rigid coiled-coil structure is likely to have an anomalous migration is SDS PAGE and therefore the 170 kDa form may be a trimer.

Protective Immunogenicity

Polyclonal anti-NadA serum was tested for bactericidal activity as previously described [Pizza et al. (2000); Peeters et al. (1999) *Vaccine* 17:2702-2712], with pooled baby rabbit serum (CedarLane) used as complement source. Serum bactericidal titer, was defined as the serum dilution resulting in a 50% decrease in colony forming units (CFU) per ml after 60 minutes incubation of bacteria in the reaction mixture, compared to control CPU per ml at time 0. Typically, bacteria incubated with the negative control antibody in the presence of complement showed a 150 to 200% increase in CPU/ml during the 60 min. of incubation.

Results were as follows:

| Strain | NadA expression | Allele | Bactericidal titre |
|---|---|---|---|
| 2996 | +++ | 3 | 32768 |
| C11 | +++ | 3 | 16384 |
| F6124 | + | 3 | 4096 |
| MC58 | + | 1 | 8192 |
| BZ232 | − | − | <4 |
| NGH38 | − | − | <4 |

As shown, the serum induced complement-mediated killing of all strains that have the nadA gene, and was inactive against the strains that do not have the gene. However, bactericidal titres varied between strains. Titres were higher against strains expressing higher amounts of protein. This result was confirmed when titres were determined in the early and late phase of growth (FIG. 15).

To check whether the differences in the bactericidal activity were due to different allele sequences, immune sera, raised, against the three NadA types, were produced and used in a cross bactericidal assay. The results obtained with the antisera were similar to those shown above, suggesting that the bactericidal activity is not influenced by the allele diversity but rather to the antigen expression level.

The ability of immune sera to protect animals from bacteremia during infection was also tested, using the infant rat model. The sera used were obtained by immunising guinea pigs with 50 µg purified rNadA (allele 3). Immunisation of outbred Wistar rats (5 to 7 days old) was performed subcutaneously together CFA for the first dose and IFA for the further three doses (days 28, 56, 84). Bleed out samples were taken on day 105 and used for the animal protection assay.

Two experiments were performed using two different MenB strains (8047 and 2996). Each strain has been serially passaged three times in infant rats. In experiment 1, groups of four rats were challenged intraperitoneally with 100 µl of a mix of (a) bacteria from strain 8047 ($7 \times 10^3$ CPU per rat) and (b) heat inactivated guinea pig antiserum or anti-capsule control mAb (SEAM 3 [Van Der Ley et al. (1992) *Infect. Immun.* 60:3156]). In experiment 2, group of six rats were treated with the control mAb or with different dilutions of guinea pig antiserum at time 0. Two hours later, they were challenged with the 2996 bacteria ($5.6 \times 10^3$ CPU per rat). In both experiments, blood cultures were obtained 18 h after the challenge by puncturing the heart with a syringe and needle containing approximately 25 U of heparin without preservative. Bacteria numbers in the blood cultures were obtained by plating out 1, 10, and 100 µl of blood onto chocolate agar overnight. For calculation of geometric mean CFU/ml, animals with sterile cultures were assigned a value of 1 CPU/ml.

Results were as follows:

| | | Blood culture at 18 hours | |
|---|---|---|---|
| $Exp^1$ | Treatment | Positive/Total | CFU/ml ($10^3$) |
| 1 | Anti-capsular mAb (2 µg/rat) | 0/4 | <0.001 |
| | Anti-NadA antiserum (1:5 dilution) | 0/4 | <0.001 |
| | PBS + 1% BSA | 5/5 | 40.17 |
| 2 | Anti-capsular mAb (20 µg/rat) | 1/6 | 0.003 |
| | Anti-NadA antiserum (1:5 dilution) | 1/6 | 0.002 |
| | Anti-NadA antiserum (1:25 dilution) | 3/6 | 0.035 |
| | Pre-immune NadA serum | 6/6 | 1.683 |

Thus anti-NadA antiserum is highly protective in this assay.

Overall, therefore, NadA has several attributes of being a good vaccine antigen: (i) it is a surface-exposed molecule, potentially involved in bacterial adhesion, (ii) it is present in at least 50% of the disease-associated strains and in almost 100% of three hypervirulent lineages; (iii) it elicits protective and bactericidal antibodies in laboratory ordinals; and (iv) each allele induces cross-bactericidal antibodies.

ORF40

Figure 7:
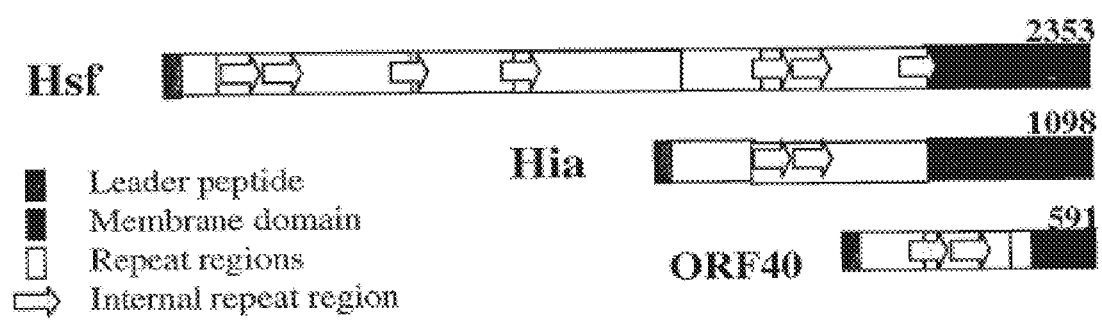
FIG. 7 shows homologies of ORF40.

ORF40 shows homology to Hsf and its allelic variant Hia, both adhesins of *Haemophilus influenzae*. The different size among Hia, Hsf and ORF40 is in part explained by the presence of three copies of a large repeated domain in Hsf, which is present in single copy in His and only partially in ORF40 (FIG. 7). In MenB, ORF40 is found on the outer membrane as a protein of about 200 kDa (cf. predicted MW of 59 kDa for mature protein).

App

Figure 8:
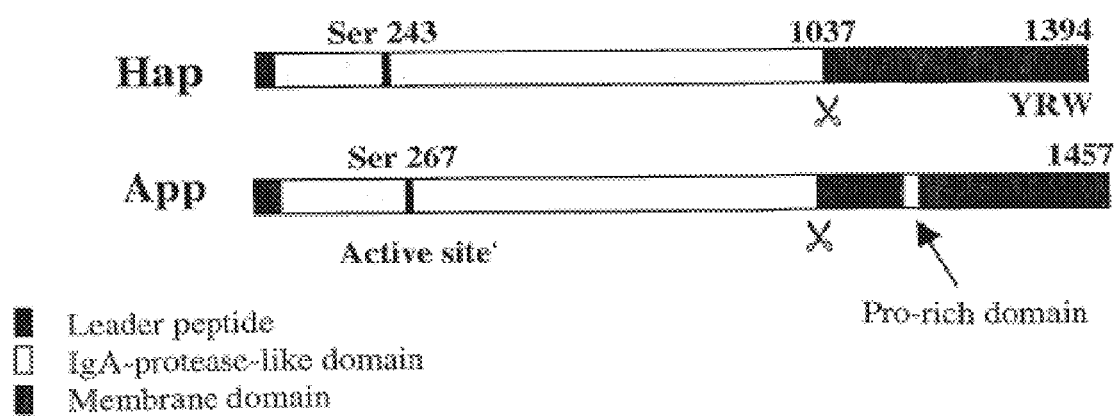
FIG. 8 shows homologies of App.

App shows homology (FIG. 8) to the adhesion and penetration protein Hap of *H. influenzae*, which is an adhesin with a serine-protease activity that undergoes autoproteolytic cleavage and extracellular release [Hendrixson et al. (1997) *Mol Microbiol* 26:505-518]. Uncleaved surface-associated Hap mediates adherence to epithelial cells and promotes bacterial aggregation and colonisation.

In *N. meningitidis*, App is exported to the outer membrane, processed and secreted. Both Hap and App belong to the autotransporter family which comprises proteins from gram-negative bacteria characterized by a distinct mechanism of secretion. This system was first described for IgA1 protease of *N. gonorrhoeae*, which is considered the prototype of this family. Proteins of the autotransporter family have been implicated in the virulence of many gram-negative pathogens [Henderson & Nataro (2001) *Infect Immun* 69:1231-1243]. They are synthesized as large precursor proteins comprising at least three functional domains: a typical N-terminal leader sequence, an internal domain (passenger domain) and a C-terminal domain (translocator domain or β-domain). The leader sequence mediates the export (sec-dependent) of the protein to the periplasm. Subsequently the translocator domain inserts into the outer membrane forming a β-barrel pore to allow the export of the passenger domain. Once at the bacterial surface, the passenger domain can be cleaved and released into the environment. Cleavage can occur by an autoproteolytic event directed by protease activity in the passenger domain itself. Passenger domains of autotransporters are widely divergent, reflecting their remarkably disparate roles. On the contrary the β-domains display high degree of conservation consistent with their conserved function.

App possesses the prevailing domains of the autotransporter proteins as well as the conserved serine protease motif (GDSGSP). It has been shown that this motif is responsible for cleavage of human IgA by the *Neisseria* IgA1 proteases and for autoproteolytic cleavage of Hap protein of *H. influenzae*, App has been shown to be a conserved antigen among meningococci, to be expressed during infection and carriage, to stimulate B cells and T cells, and to induces a bactericidal antibody response [Hadi et al. (2001) *Mol. Microbiol.* 41:611-623; Van Ulsen et al. (2001) *FEMS Immunol Med Microbiol* 324.53-64].

Figure 26:
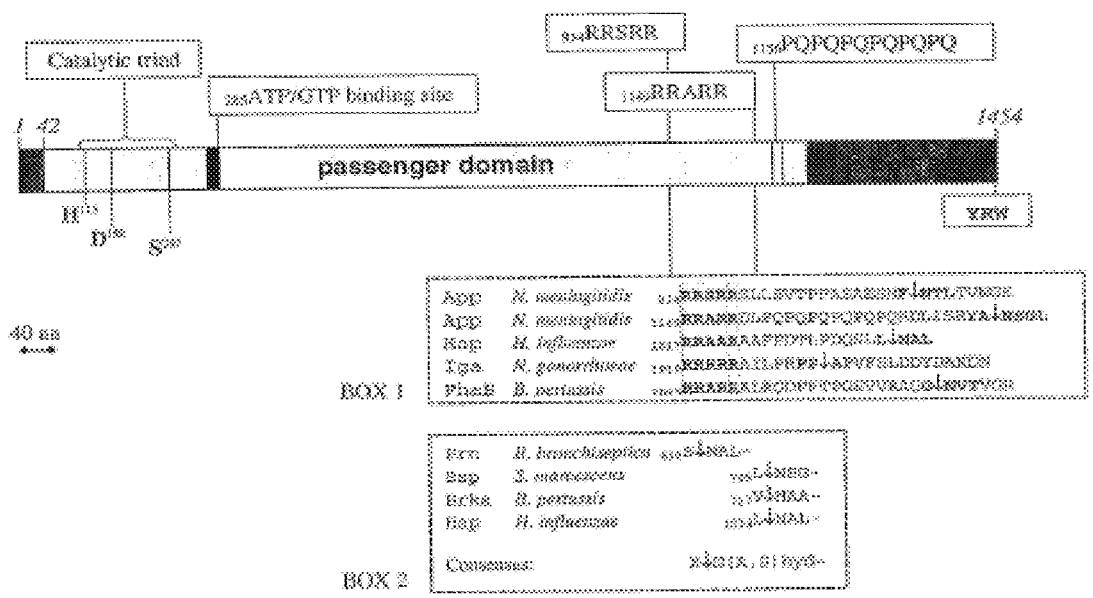
FIG. 26 is a schematic representation of App features. The N-terminal leader peptide, the passenger domain and the C-terminal β-domain are indicated. The positions of the serine protease active site, the ATP/GTP binding site, the two Arginine-rich sites (SEQ ID NO: 53) (starting at residue 934) and (SEQ ID NO: 54) (starting at residue 1149) and the Proline-rich region (SEQ ID NO: 55) are shown. In BOX 1, cleavage sites are shown. Sequences shown in BOX 1 correspond to (top to bottom): SEQ ID NO: 43, SEQ ID NO: 56, SEQ ID NO: 45, SEQ ID NO: 46, and SEQ ID NO: 47. In BOX 2 a comparison of known proteolytic sites of different autotransporters is shown (SEQ ID NOS: 48-51) (top to bottom) and a consensus signature is derived (SEQ ID NO: 57). Arrows identify the cleavages; X=any amino acid; hyd=hydrophobic residues; (A,S)=Alanine or Serine.

In serogroup B strain 2996, App has 1454 amino acids and a predicted MW of 19,965 Da. FIG. 26 shows the protein's predicted structural features. Three domains can be seen: domain 1 (amino acids 1-42) is the signal peptide; domain 2 is the passenger domain, which is the functionally active protein; domain 3 is the C-terminal translocator domain with β barrel structure.

At the N-terminus of the passenger domain, His-115, Asp-158 and Ser-267 correspond to the serine protease catalytic triad His-98, Asp-140 and Ser-243 from Hap [Fink et al. (2001) *J Biol Chem* 276:39492-39500]. Residues 285-302 are a putative ATP/GTP-binding site (P loop), which suggests a mechanism of energy coupling for outer membrane translocation. Towards the C-terminus of the passenger domain, two Arg-rich regions are present. The first (RRSRR) is residues 934-938 and the second (RRARR) begins at residue 1149. These motifs are reminiscent of known targets for trypsin-like proteolytic cleavage sites such as the one in diphtheria toxin and those upstream of the auto-cleavage sites of *H. influenzae* Hap, *N. gonorrhoeae* IgA-protease and *B. pertussis* FhaB (FIG. 26, box 1). Downstream of the Arg-rich regions are motifs $^{934}$NTL$^{956}$ and $^{1176}$NSG$^{1178}$, which are identical or similar to the cleavage sites in autotransporters Sap (*Serratia marcescens*), Pni (*Bordetella brinchiseptica*), Brka (*Bordetella pertussis*) [Jose et al., (1995) *Mol. Microbiol.* 380] and Hap (*H. influenzae*) (FIG. 26, box 2). Together, these sequence motifs suggest that the two motifs $^{954}$NTL$^{956}$ and $^{1176}$NSG$^{1178}$ and the RR(A,S,R)$_2$RR pattern could act as signals for correct localisation of downstream processing sites.

Further analysis of the App sequence shows a proline-rich region, where the dipeptide motif PQ is repeated four times beginning at residue 1156. A search for homology to known protein sequences reveals some similarity to the surface proteins of *S. pneumonie* PspA and PspC and to a proline-rich region of the *B. pertussis* outer membrane protein p69 pertactin, where the (PQP)$_5$ motif is located in a loop containing the major immunoprotective epitope.

Finally, the last three amino acids of App (YRW) are identical to those of Hap where they have been described as crucial for outer membrane localisation and protein stability [Hendrixson et al., 1997].

Expression in *E. coli* without Fusion Partners

ORF40, App and NadA full-length genes were cloned in pET21b+ vector and the plasmids were transformed in *E. coli* BL21(DE3) in order to express the genes under control of T7 promoter.

Expression was achieved activating the promoter with IPTG or under non-induced conditions. Localisation and surface-exposure of the proteins were assayed by cell-fractionation experiments (SDS-PAGE and Western blot), FACS analysis and whole-cell immunoblot. As shown in FIGS. 1 to 3, all the three proteins are translocated to the surface of *E. coli*:

ORF40 is expressed as monomeric form and possibly forms also multimers (FIG. 1).

App is exported to *E. coli* outer membrane as a precursor of about 160 kDa, that is processed and secreted in the culture supernatant (FIG. 2).

NadA is found to the be present in the outer membrane fraction as a single high molecular weight band of approximately 180 kDa. This probably corresponds to an oligomeric form of the protein. Such a band is absent in *E. coli* expressing intracellular NadA (FIG. 3).

App expression was studied in more detail.

Figure 27:
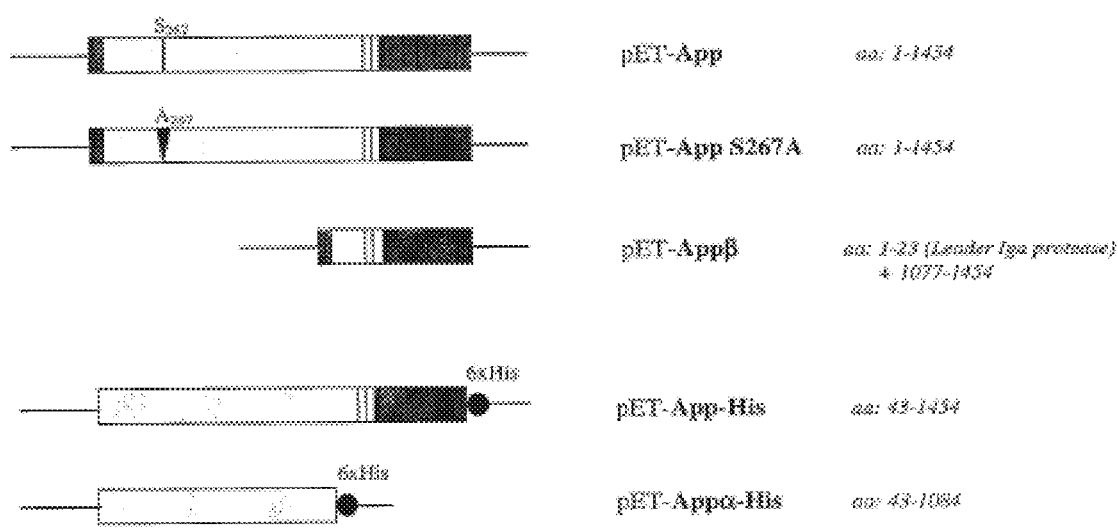
FIG. 27 is a schematic representation of the constructs used for studying App.

*N. meningitidis* strain 2996 genomic DNA was prepared as previously described [Tinsley & Nassif (1996) *PNAS USA* 93:11109-11114]. DNA devoid of the sequence coding for the signal peptide (amino acids 1 to 42) and of the STOP codon was amplified using PCR primers SEQ IDs 18 & 19 followed by digestion with NheI and XhoI and insertion into the NheI/XhoI sites of the pET-21b expression vector, to give 'pET-App-His' (FIG. 27). This plasmid was introduced into *E. coli* BL21(DE3) and used for the expression of C-terminal His-tagged fusion protein which was purified and used to raise antibodies. The full-length app gene was amplified and cloned in a similar way, using PCR primers SEQ IDs 20 & 21, to give plasmid 'pET-App'.

Figure 28:
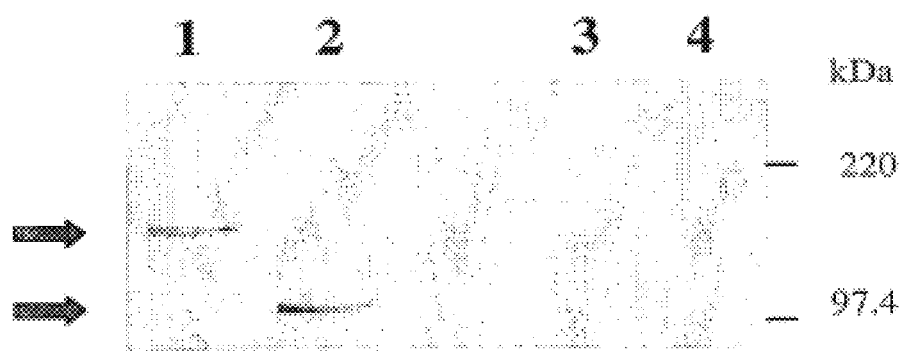
FIG. 28 shows a western blot of outer membrane and extracellular proteins in E. coli.

Plasmids were introduced into *E. coli* BL21(DE3) and expression induced by addition of 1 nM IPTG. The expressed protein was detected by western blotting (FIG. 28, lane 1). To verify that the protein was exported to the *E. coli* surface, FACS (FIG. 29) and immunofluorescence microscopy (FIG. 30) were used. The FACS analysis showed positive surface expression on the pET-App transformants (full-length gene) but no surface expression with App-His (no signal peptide) or with the empty vector. The immunofluorescence results agreed with FACS. Therefore expression of the full-length app gene resulted in the export of App to the surface of *E. coli*, but deletion of the first 42 amino acids abolished surface-localisation.

Western blot analysis of outer membrane proteins from pET-App transformants revealed a specific reactive band of ~0.160 kDa (FIG. 28, lane 1), corresponding to the predicted molecular weight of the full-length protein. A corresponding band was missing in the outer membrane fraction from transformed controls (lane 3). Western blot analysis of culture supernatants revealed a secreted protein of ~100 kDa with pET-App (lane 2) that was absent with the untransformed controls (lane 4). Sometimes a very weak band was also detected at ~140 kDa in pET-App transformants.

Therefore the full length app gene when introduced into *E. coli* induces expression of an App protein which is exported to the outer membrane, cleaved and released into the culture supernatant.

Native Expression can Influence the Quality of the Immune Response

To evaluate the role of protein conformation on induction of an immune response, outer membrane vesicles from *E. coli* expressing ORF40, App or NadA were isolated and used to immunise mice. Sera were tested for bactericidal activity and results compared with those obtained with the fusion proteins. The bactericidal response (strain 2996) was improved 5-10 fold when the proteins are produced in their "native" form in OMVs:

|  | Bactericidal titres* | |
| --- | --- | --- |
| Antigen | Fusion protein | *E. coli* OMV |
| ORF40 | 256 | 2048 |
| App | 64 | 1024 |
| NadA | 32768 | >65536 |

*Titres expressed as the reciprocal of the serum dilution yielding-50% bacteria killing App Autoproteolytic Cleavage

*E. coli* pET-App transformants secrete a 100 kDa product into culture supernatant and show a 160 kDa surface product. To test whether the secreted App product derives from an autoproteolytic process, one of the putative catalytic residues (Ser-267) was replaced with Ala.

The pET-AppS267A mutant was obtained by site-directed mutagenesis using the QuikChange kit (Stratagem) and primers SEQ IDs 22 & 23.

Figure 29:
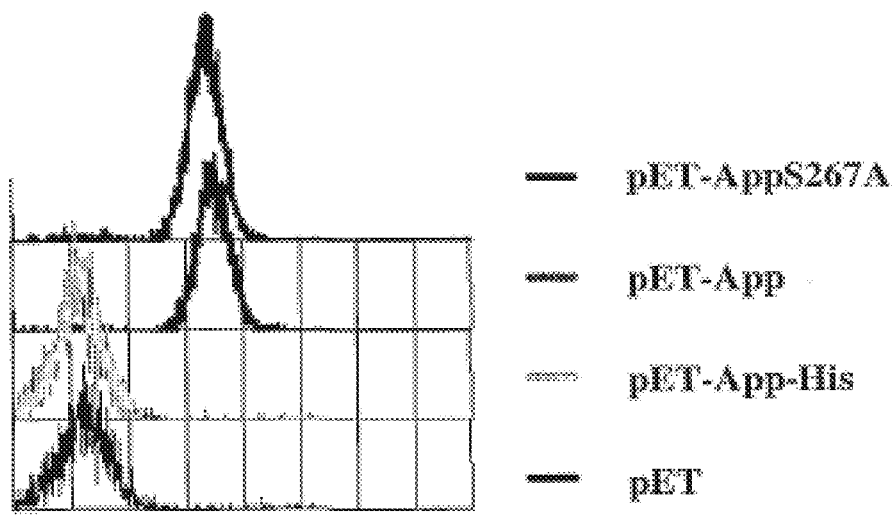
FIG. 29 shows FACS analysis of outer membrane and extracellular proteins in E. coli.
Figure 30A:
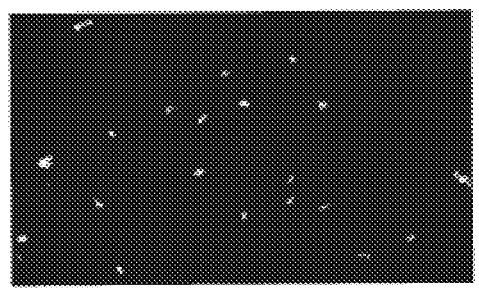
FIG. 30A-FIG. 30C show immunofluorescence of outer membrane and extracellular proteins in *E. coli* harboring pET-App (FIG. 30A), pET-App-His (FIG. 30B), or pET (FIG. 30C).
Figure 30B:
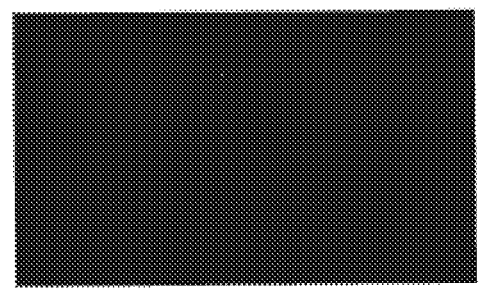
Figure 30C:
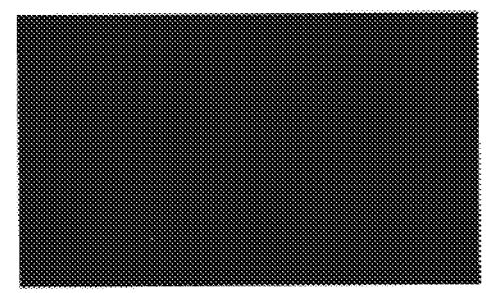
Figure 31:
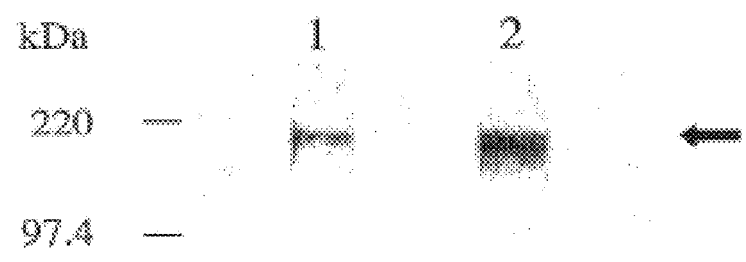
FIG. 31 shows total *E. coli* proteins analysed by SDS-PAGE.
Figure 32:
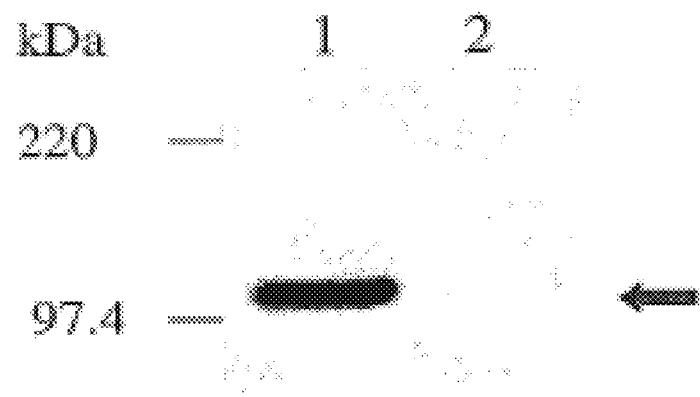
FIG. 32 shows an immunoblot of crude precipitated culture supernatants using mouse antiserum against App-his.

SDS-PAGE analysis of total proteins from pET-AppS267A transformants (FIG. 31) lane 2) showed protein similar in size to pET-App transformants (lane 1). The protein was shown to be surface exposed by FACS analysis (FIG. 29). Western blot analysis of culture supernatants showed App in pET-App transformants (FIG. 32, lane 1) but not in pET-AppS267A transformants (lane 2).

Mutation of Ser-267 to Ala thus abolishes processing and secretion of the App precursor, which remains cell-associated. These data suggest that App has a maim protease activity that is responsible for autoproteolytic preening and release in the supernatant of the secreted App domain.

Cleavage at $^{954}$NTL$^{956}$ would leave a fragment with predicted molecular weight of 104190 Da. Cleavage at $^{1176}$NSG$^{1378}$ would give a 128798 Da fragment. These two predicted fragments may match the two bands of ~140 and ~100 kDa observed in culture supernatants. Cleavage may occur first to give the ~140 kDa fragment and then second to give the 100 kDa fragment. The β domain of App would thus begin at residue 1177.

NadA, ORF40 and App Function as Adhesins

Example 22 of international patent application WO01/64922 discloses that NadA expression in *E. coli* makes the transformed bacterium adhere to human epithelial cells. The adherent phenotype has been further studied for NadA and also for App and ORF40.

*E. coli* BL21(DE3) bacteria (10$^8$ CFU), grown under non-induced or induced conditions, were inoculated onto Chang human epithelial monolayers (10$^5$ cells) and incubated at 37° C. for 1 or 2 hours. Cells were then incubated with rabbit anti-*E. coli* and PE-conjugate secondary antibody. Adhesion was detected by FACS as specific fluorescence intensity associated to Chang cells. Positive controls were *E. coli* DH5 expressing hsf (DH5/pDC601)); negative controls were BL21(DE3)/pET21b and DH5a/pT7-7. The results in FIG. 4 show that the ability of the recombinant *E. coli* strains to adhere to cultured epithelial cells is associated with expression of these three proteins.

To confirm that these three proteins are able to promote interaction with host cells, the recombinant proteins themselves were investigated for binding to epithelial cells. 10$^5$ Chang human epithelial cells (Wong-Kilbourne derivative, clone 1-5c-4, human conjunctiva) were incubated at 4° C. for 30 minutes with medium alone or with different concentration of ORF40 (150 μg/ml), App (150 μg/ml) or NadA (300 μg/ml), or with GNA2132 (300 μg/ml) as negative control [see Pizza (2000)]. Binding was detected by FACS using polyclonal antisera against the single recombinant proteins and a secondary PE-conjugate antibody. The FACS signal shifts (FIG. 5) show that the three proteins are able to bind to human epithelial cells, whereas purified GNA2132 (negative control) does not.

FIG. 6A shows that binding increases in a dose-dependent manner. Binding of NadA reaches a plateau at around 200 μg/ml. GNA2132 fails to bind even at 400 μg/ml (FIG. 6B). Data in FIG. 6 are mean fluorescent intensity (MFI) values plotted against protein concentration (μg/ml).

Using FACS, binding of NadA to cells was also seen with Hep-2 and MOLT-4 cells, but not with HeLa, A549, Hec-1B, Hep-G2, CHO or HUVBC cells. Adhesion to Chang cells could be abolished by treating the cells with pronase, indicating that the human receptor for NadA is a protein.

Adhesion of purified NadA protein to Chang conjunctiva cells was also observed using immunofluorescence microscopy. The protein (lacking its C-terminal anchor domain) was incubated with Chang cells at 37° C. in complete culture medium for 3 hours at various concentrations. Cells were then washed, fixed, and analysed by laser confocal microscopy after staining with anti-NadA mouse polyclonal antibodies and secondary Texas-red coupled anti-Mouse IgG antibodies. No binding was seen at 0 nM (FIG. 1A), but binding was evident at 170 nM (17B) and 280nM (17C), with clustering evident at higher concentrations. In contest, no binding of NadA was seen with HeLa cells, even at 280nM protein (17D).

Figure 18A:
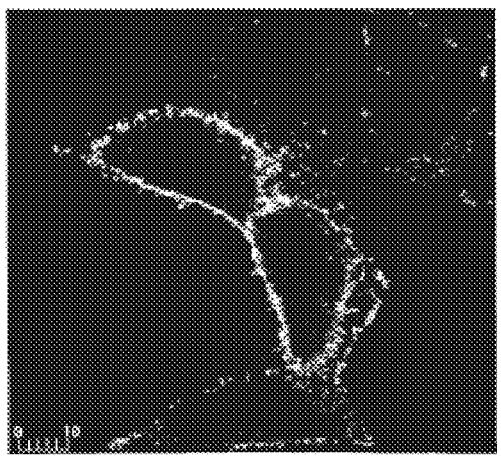
FIG. 18A-FIG. 18B show immunofluorescence results obtained using anti-NadA against Chang cells after incubation at 37° C.
Figure 18B:
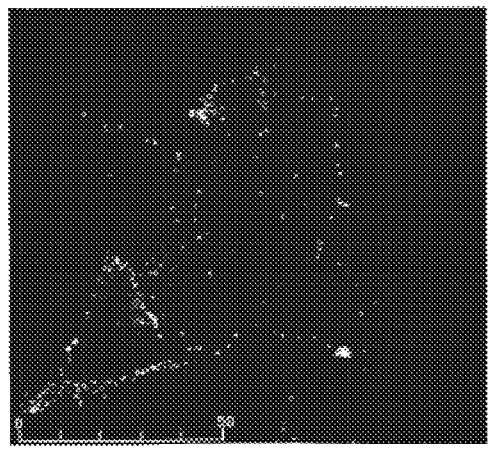

Binding was much more evident at 37° C. (FIG. 18A) than at 4° C. (FIG. 18B). The dot-like structures seen at 4° C., compared to clusters at 37° C., suggest that lateral interactions between NadA monomers are temperature-dependent (influenced by membrane fluidity).

Figure 19:
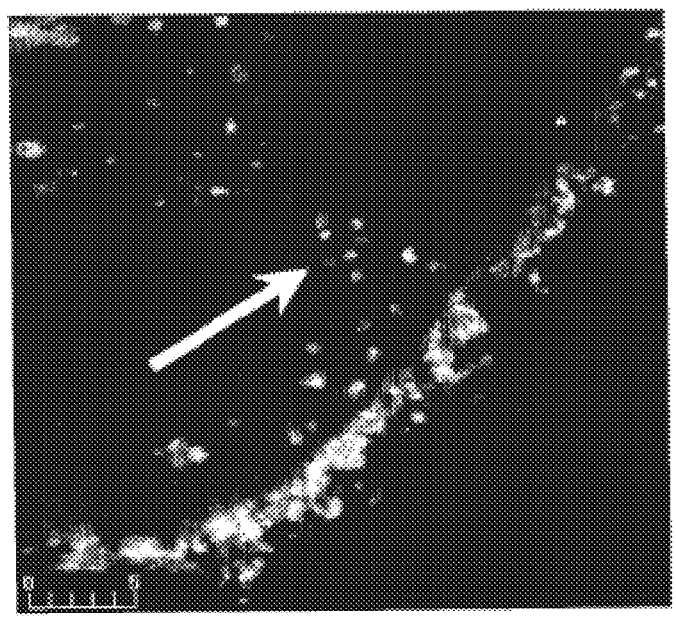
FIG. 19 shows immunofluorescence results for Chang cells treated with saponin.

To distinguish surface and endocytosed protein, saponin detergent was added during the staining procedure. Intracellular clusters having the size of endosomes were more evident (arrow) when saponin was used, but a high proportion of protein remained on the cell surface (FIG. 19).

Figure 20A:
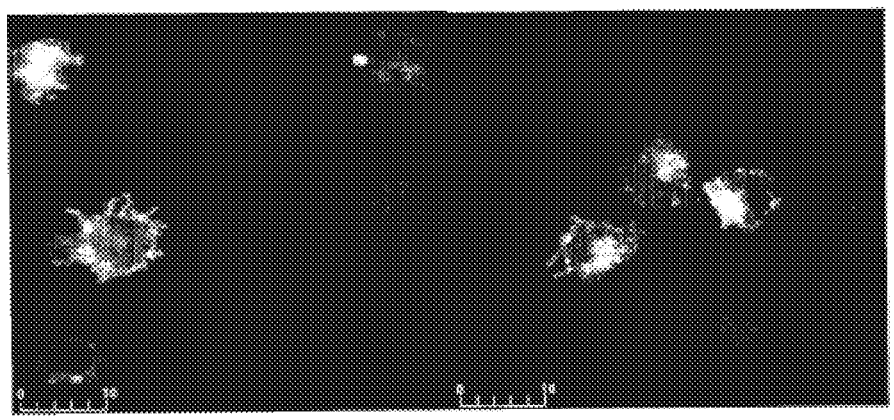
Figure 20A:
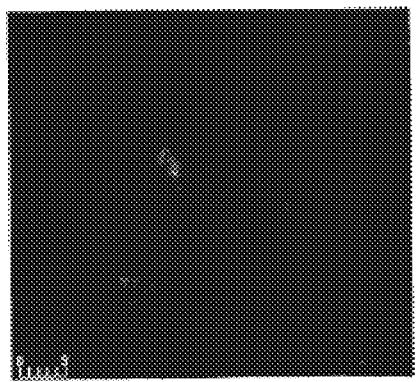
Figure 20A:
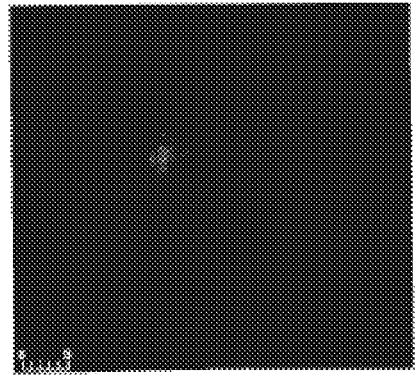

Immunofluorescence also revealed that NadA binds to monocytes (FIG. 20A). NadA alone (no staining antibody; 20B) and NadA stained with pre-immune serum (20C) were not visible. At high magnification, evidence of uptake into vesicles (either endosomes or phagosomes) was seen.

Figure 21:
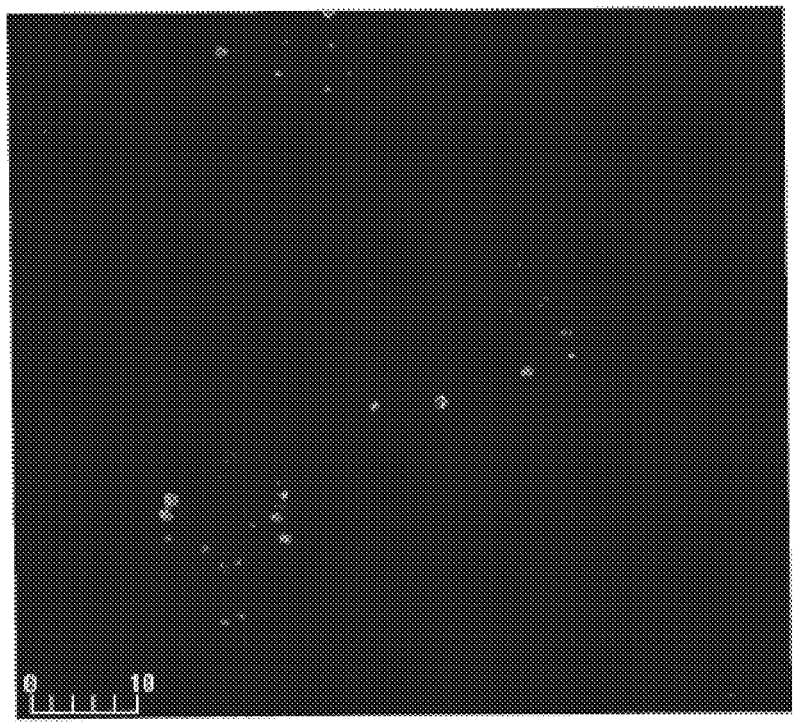
FIG. 21 shows immunofluorescence results obtained using macrophages.

FIG. 21 shows that murine macrophages (raw 264.1) bind and endocytose NadA (125nM, 3 hours, 37° C.; cells cultured in DMEM).

Figure 22:
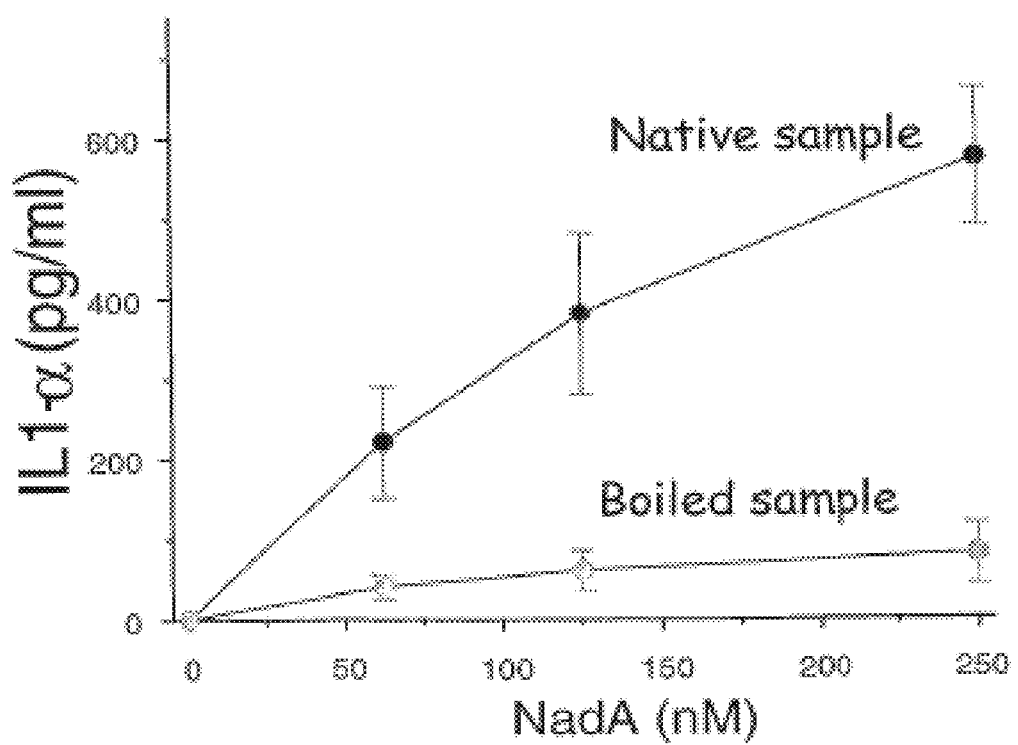
FIG. 22 shows IL-α secretion by monocytes in response to NadA treatment.
Figure 23:
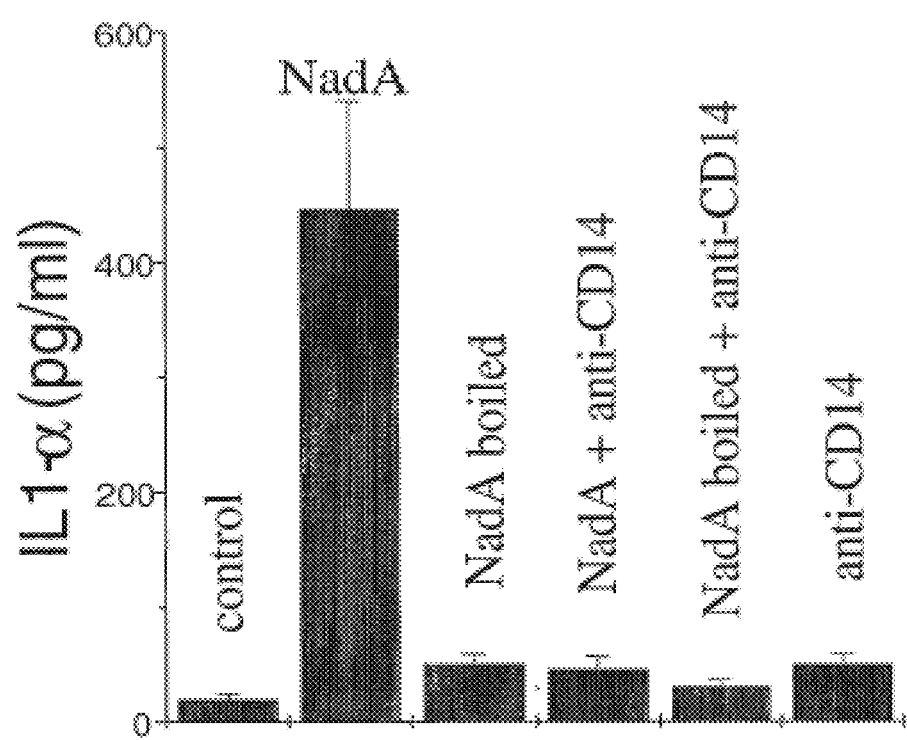
FIG. 23 shows the effect of anti-CD14 on IL-α secretion by monocytes.

Beating NadA at 95° C. for 15 minutes prior to incubation removed its ability to bind to monocytes as measured by secretion of IL-α by the cells (FIG. 22). The stimulatory activity of NadA preparations is thus heat-labile. Stimulatory activity was also blocked by the use of anti-CD14 (FIG. 23) or by the removal of NadA from the preparations using bead-immobilised anti-NadA.

Figure 24A:
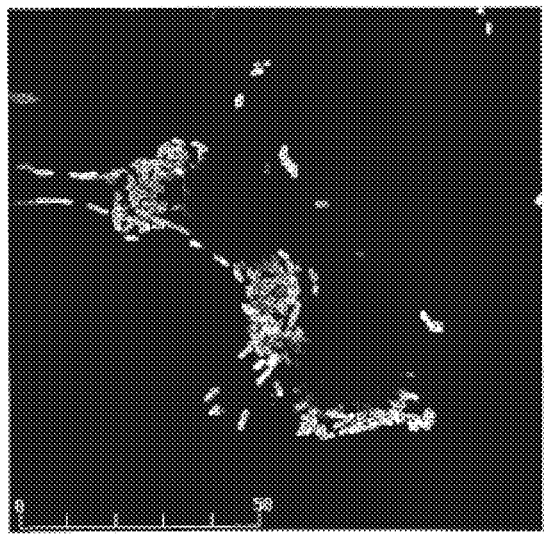
FIG. 24A-FIG. 24B show immunofluorescence results obtained using anti-NadA against E. coli transformed to express NadA (FIG. 24A) or untransformed bacteria (FIG. 24B).
Figure 24B:
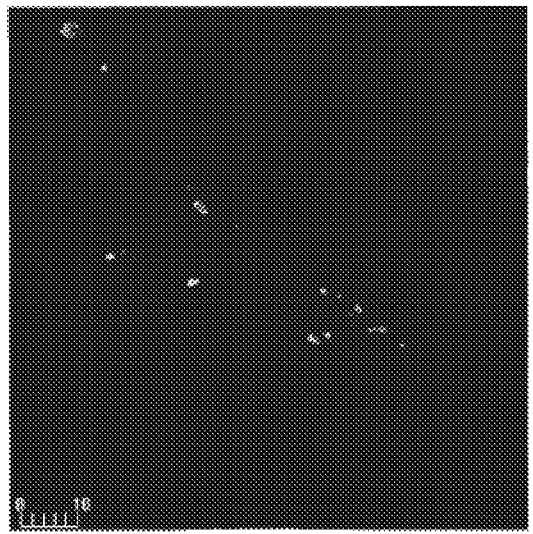

Immunofluorescence microscopy was also used to detect binding of *E. coli* expressing NadA. Transformed *E. coli* bound strongly (FIG. 24A) whereas untransformed bacteria did not (24B). IL-α release by monocytes was over 1.5× higher using the transformed *E. coli* than the untransformed bacteria at a bacteria/monocyte ratio of 40:1.

Figure 25A:
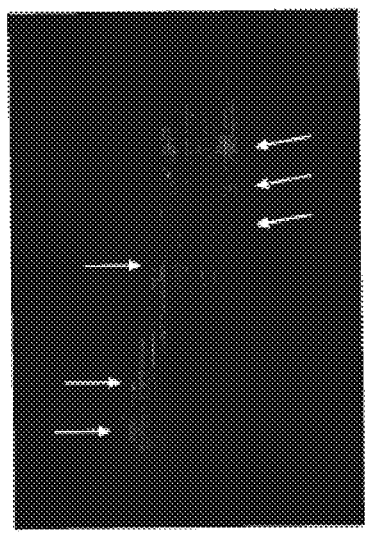
FIG. 25A-FIG. 25C show staining of the transformed E. coli using anti-NadA (FIG. 25A), anti-E. coli (FIG. 25B), or both (FIG. 25C).
Figure 25B:
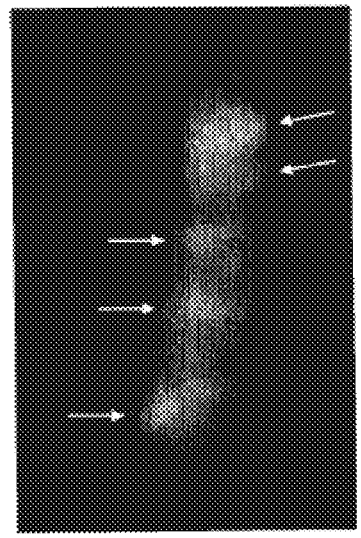
Figure 25C:
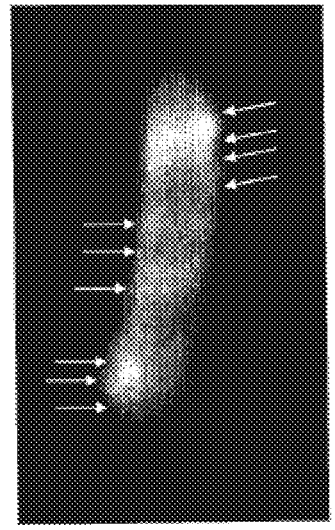

Transformed *E. coli* were bound to glass cover slips, fixed and double-stained with anti-NadA (FIG. 25A) and anti-*E. coli* antibodies (25B). When both were used patches of anti-NadA were visible, suggesting that NadA tends to form aggregates on the bacterial surface, which hamper the interaction of antibodies with other surface antigens.

Looking at App, recombinant *E. coli* strains were incubated with monolayers of Chang conjunctiva epithelial cells (Wong-Kilbourne derivative, clone 1-5c-4 [human conjunctival], ATCC CCL 20.2) and adhesion was analysed using FACS. Cells obtained from confluent monolayers were seeded at $10^5$ cells per well in 12-well tissue culture plates and incubated for 24 hours. Cultures of bacteria after IPTG induction were washed twice in PBS and resuspended in DMEM+1% PBS to a concentration of $5 \times 10^8$ bacteria per ml. Aliquots of 1 ml of each strain were added to monolayer cultures of Chang cells and incubated for 3 hours at 37° C. in 5% $CO_2$. Non-adherent bacteria were removed by washing three times with PBS, and 300 µl of cell dissociation solution (Sigma) were added to each microtitre well. Incubation was continued at 37° C. for 10 minutes. Cells were harvested and then incubated for 1 hour at 4° C. with rabbit polyclonal anti-*E. coli* antiserum (DAKO). Cells were washed twice in PBS+5% FBS and incubated for 30 minutes at 4° C. with R-Phycoerythrin-conjugated anti-rabbit IgG (Jackson ImmunoResearch Laboratories). Cells were then washed in PBS+5% PBS and resuspended in 100 µl PBS. Fluorescence was, measured With FACSCalibur flow cytometer (Becton Dickinson). For each of fluorescence profile, 10000 cells were analysed.

Figure 33:
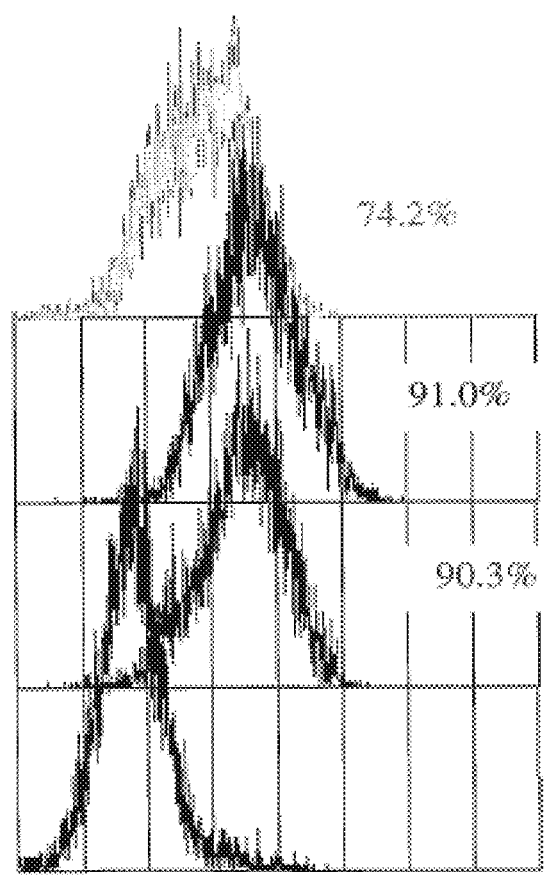
FIG. 33 shows FACS adhesion data using rabbit antiserum against *E. coli*. Percentages of cells positive to adhesion are shown near the fluorescence profiles.

The results reported in FIG. 33 show pET-App transformants were able to adhere to Chang cells, giving a fluorescence shift of 90.3%. S267A transformants were also able to adhere (91.0%). Untransformed *E. coli* were unable to adhere to Chang cells (bottom FACS plot).

Figure 34A:
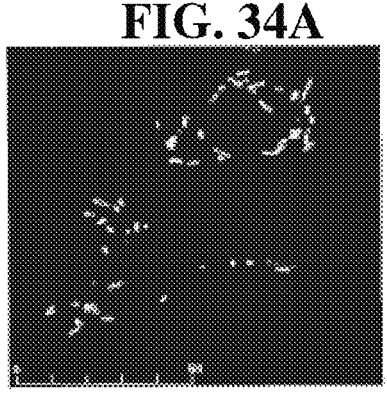
FIG. 34A-FIG. 34G show immunofluorescence microscopy data showing bacterial adherence and aggregation.
Figure 34B:
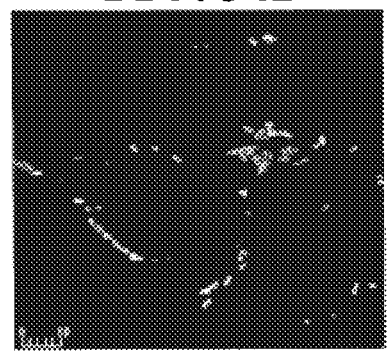
Figure 34C:
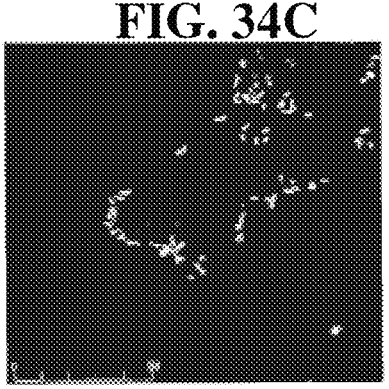
Figure 34D:
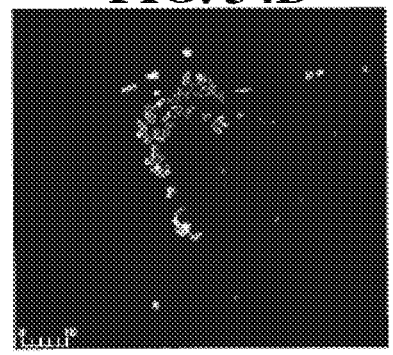

As for NadA, FACS results were in agreement with immunofluorescence microscopy data. As shown in FIGS. 34A & 34B, pET-App transformants incubated with monolayers demonstrated high levels of adhesion to epithelial cells and visible bacteria-bacteria aggregation. For the S267A mutant, adhesion and bacterial aggregation were increased (34C & 34D). Untransformed controls showed no adhesion (34G). Deletion of the first 42 amino acids also abolished adhesion.

In contrast to Chang epithelial cells, no adhesion was seen when HUVBC endothelial cells were tested with pET-App transformants. To cause sepsis and meningitis, *N. meningitidis* has to interact with human endothelial cells. App may thus be involved in the first step of colonisation at the level of human respiratory epithelial mucosa, rather than in pathological endothelial colonisation.

Localization and Specificity of App Binding Activity.

To identify the binding region of App, a chimeric protein named Appβ was used. This protein consists of the C-terminal domain of App (amino acids 1077 to 1454) fused to the leader peptide of IgA1 protease of *N. gonorrhoeae*. The gonococcal leader sequence was chosen because it has been well characterized and is functional in *E. coli*. Plasmid pET-Appβ contains a 1.1 kbp DNA fragment amplified by PCR using SEQ IDs 26 & 27.

Figure 34E:
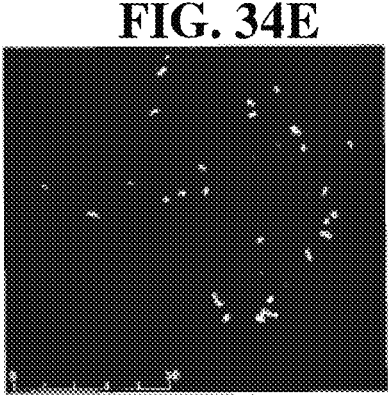
Figure 34F:
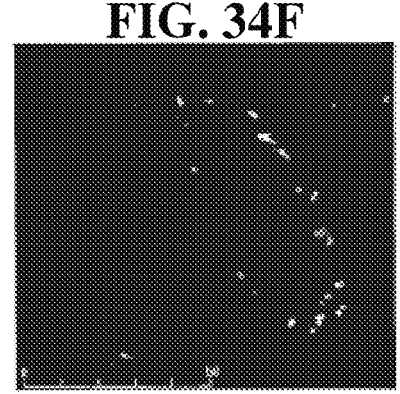
Figure 34G:
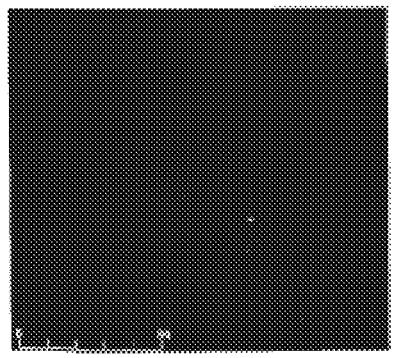

The pET-Appβ construct was introduced into *E. coli* BL21 (DE3). FACS localisation studies confirmed that Appβ was localized on the *E. coli* surface. The in vitro adhesion assay using Chang epithelial cells showed adhesion by immunofluorescence (FIGS. 34E & 34F). FACS analysis showed that the pET-Appβ transformants were still able to adhere to epithelial cells but at lower levels (74.2% shift) than pET-App transformants.

These results indicate that the App binding domain is located in its C-terminal region, in the 100mer fragment between residues 1077 and 1176.

Figure 35:
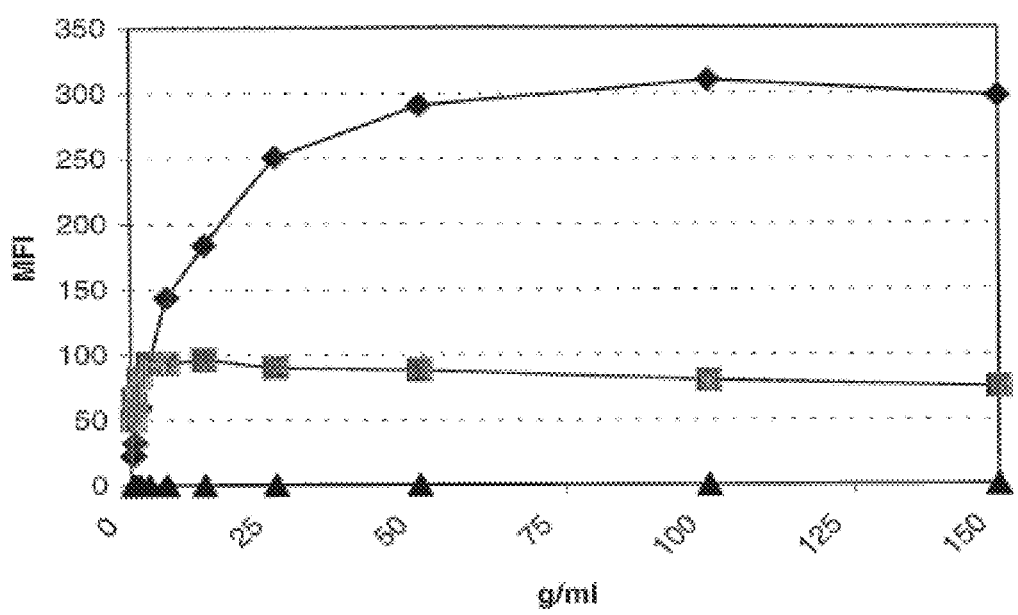
FIG. 35 shows concentration-dependent binding of App-His (♦), Appα-His (■) and NMB2132 (▲) expressed as net Mean Fluorescence Intensity (MFI).

Purified recombinant proteins were also studied. App-α-His consists of the N-terminal portion of App (amino acids 43-1084) fused to a poly-His tag Plasmid pET-Appα-His contains a NheI/XhoI 3.1 kbp fragment amplified by PCR with SEQ IDs 24 & 25. The binding activity of the purified recombinant App-α-His was compared to that of App-His by FACS binding assays. Chang cells were incubated with increased concentrations of recombinant App proteins or lipoprotein NMB12132-His (negative control). Binding of App-His (♦) increased in a close-dependent manner and reached a plateau at a concentration of ~50 µg/ml whereas the binding of Appα-his (■) was very low (FIG. 35). The control NMB32132-His (▲) failed to bind Chang cells.

Figure 36:
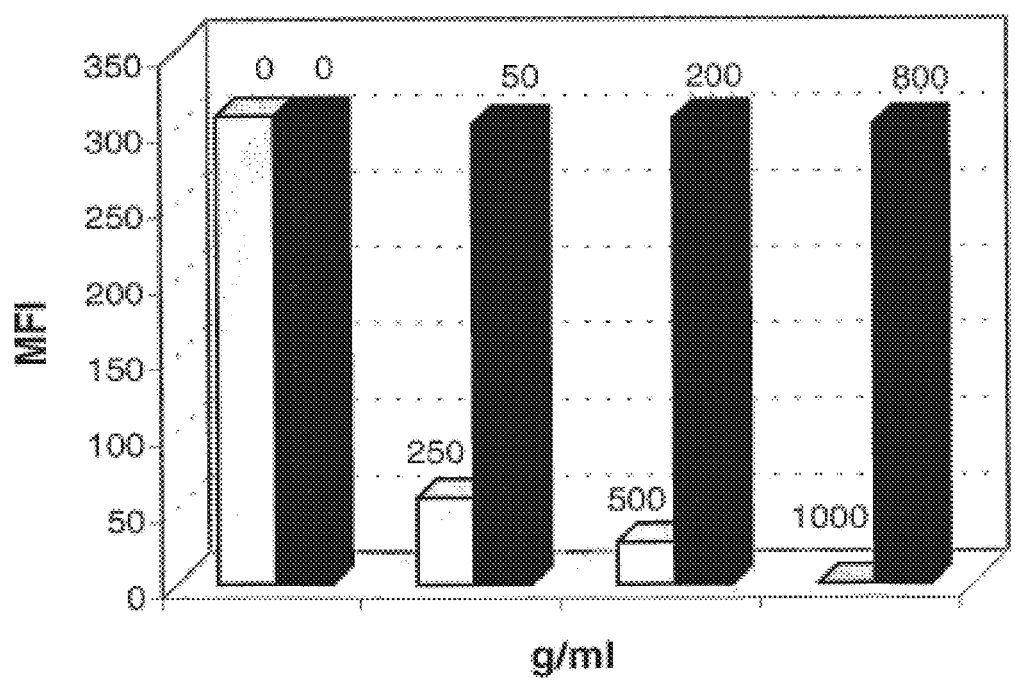
FIG. 36 shows the effect on binding of App-His (100 μg/ml) of pre-incubation with pronase (left-hand columns) or phospholipase A2 (right-hand columns) with increasing concentration of enzyme. Pronase was tested at 0, 250, 500, 1000 μg/ml; phosholipase A2 was tested at 0, 50, 200, 800 μg/ml.

To explore the biochemical nature of the molecule involved in interaction with App, the Chang cells were treated with pronase or phospholipase A2 before the binding experiments. $10^5$ cells per well were placed in microplates and incubated in FCS-free DMEM at 37° C. in 5% $CO_2$ for 30 minutes with (a) pronase at 250, 500, or 1000 µg/ml or (b) phospholipase A2 at 50,200, or 800 µg/ml. After enzymatic incubation, an equal volume of complete medium was added to each well to stop the reaction. Cells were subsequently mixed with 100 µg/ml App-His or medium alone and incubated for 1 hours at 4° C. As shown in FIG. 36, pronase treatment (left-hand columns) markedly reduced the binding of App-His protein to Chang cells, while treatment with phospholipase A2 (right-hand columns) did not reduce the binding. The receptor for App on Chang cells is thus proteinaceous.

Figure 37:
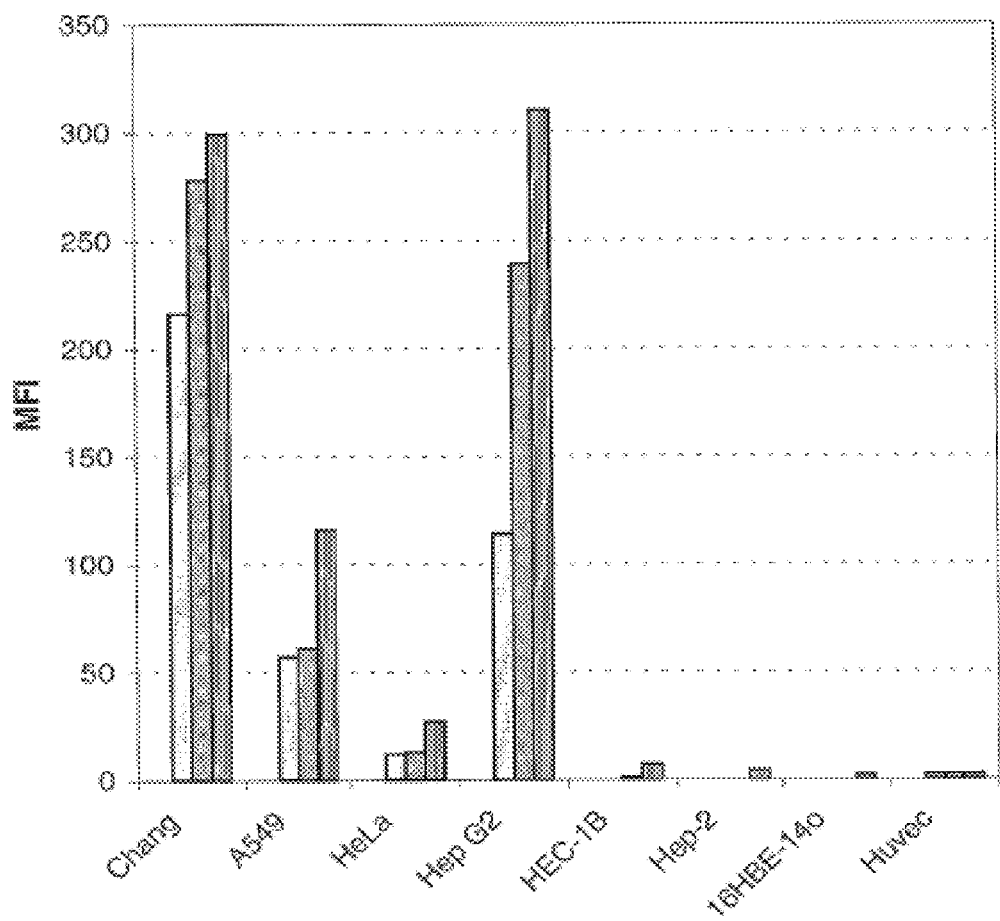
FIG. 37 is a comparison of cellular binding specificity of App-His protein at 100, 25 or 6.25 μg/ml against various different cells.

Adhesion to different cell lines were also tested (FIG. 37). After incubation of cultured cells with three different concentrations of App-His (100, 25 & 6.25 µg/ml) high level binding to Chang cells and HepG2 cells was seen, a moderate level of binding to A-549 cells, and minimal binding to HeLa cells. No binding was observed to Hec-1-B, Hep-2, 16HBE14o epithelial cell lines or to HUVBC endothelial cells.

App Knockout

After the work on *E. coli* suggesting an adhesin role for App, isogenic mutant strain of *N. meningitidis* was constructed. The starling strain was MC58. Its app gene was truncated and replaced with an antibiotic cassette by transforming the parent strain with the plasmid pBSUDAppERM, which contains a truncated app gene and the ermC gene (erythromycin resistance) for allelic exchange. Briefly, 600 bp of the upstream flailing region including the start codon and 760 bp downstream flanking region including the stop codon were amplified from MC58 using primers SEQ IDs 28 to 31. Fragments were cloned into pBluescript and transformed into *E. coli* DH5 rising standard techniques. Once all subcloning was complete, naturally competent *N. meningitidis* strain. MC58 was transformed by selecting a few colonies lawn overnight on GC agar plates, and mixing them with 20 µl of 10 mM TrisHCl pH8.5 containing 1 µg of plasmid DNA. The mixture was spotted onto a GC agar plate, incubated for 6 hrs at 37° C., 5% CO2 then diluted in PBS and spread on GC agar plates containing 5 µg/ml erythromycin. The deletion app gene in the genome of MC58 was confirmed by PCR. Lack of App expression was confirmed by Western blot analysis.

Figure 38:
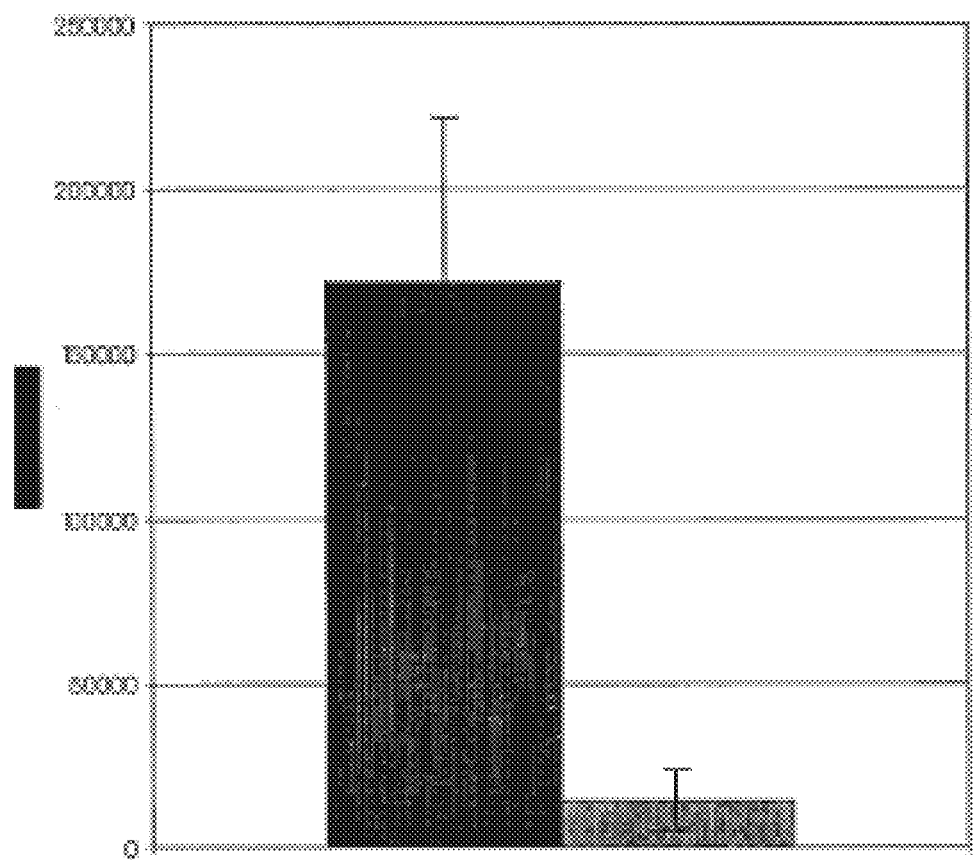
FIG. 38 shows association of wild-type or App-knockout *N. meningitidis* MC58 bacteria.

Adhesion of wildtype MC58 and the isogenic MC58Δapp mutant strain was evaluated on Chang cells. There was a ~10 fold reduction (ranging from 3- to 27-fold in different experiments) of the association of the knockout mutant compared with the wild type strain (FIG. 38). No difference was observed between the app mutant and the parental strain with Hep2 and 16HBE14o cell lines and with HUVEC endothelial cells, confirming that App does not mediate adhesion to these cells.

No non-pilus adhesins which contribute to adhesion of *N. meningitidis* in a capsulated background have previously been reported.

Figure 39:
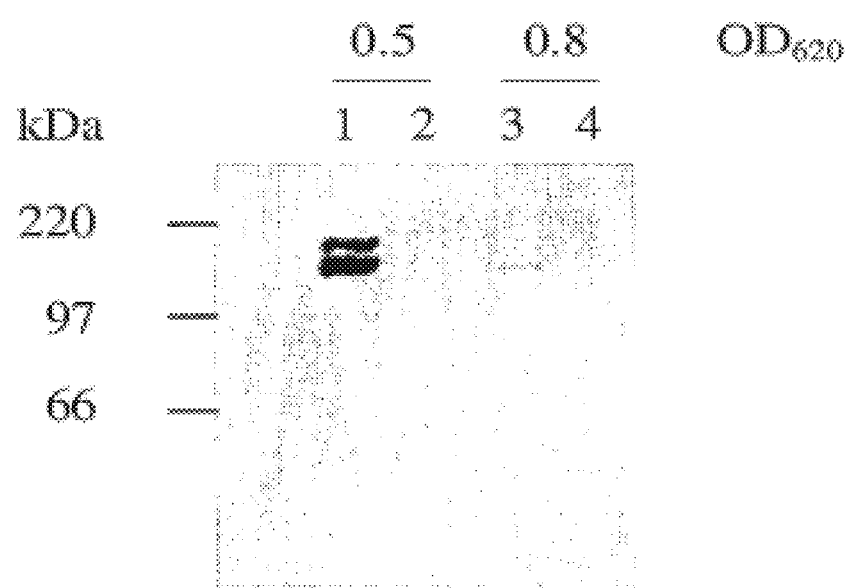
FIG. 39 shows a western blot analysis of total lysates from *N. meningitidis* MC58 harvested at 0.5 or 0.8 $OD_{620nm}$. Lanes 1 & 3 show wild-type MC58 and lanes 2 & 4 show the App knockout.

App expression was studied in *N. meningitidis* MC58. Colonies from plates grown overnight were diluted in GC broth and incubated at 37° C. with 5% $CO_2$. Samples were taken when $OD_{620nm}$=0.5 (mid log phase) and 0.8 (stationary phase) and analysed by western blot. Two bands with apparent molecular weights ~160 and ~140 kDa were detected in whole cells lysates of log phase bacteria (FIG. 39, lane 1), while stationary phase bacteria showed only a faint band at ~140 kDa (lane 3). As expected, no App was observed in the ΔApp mutant (lanes 2 & 4).

Figure 40:
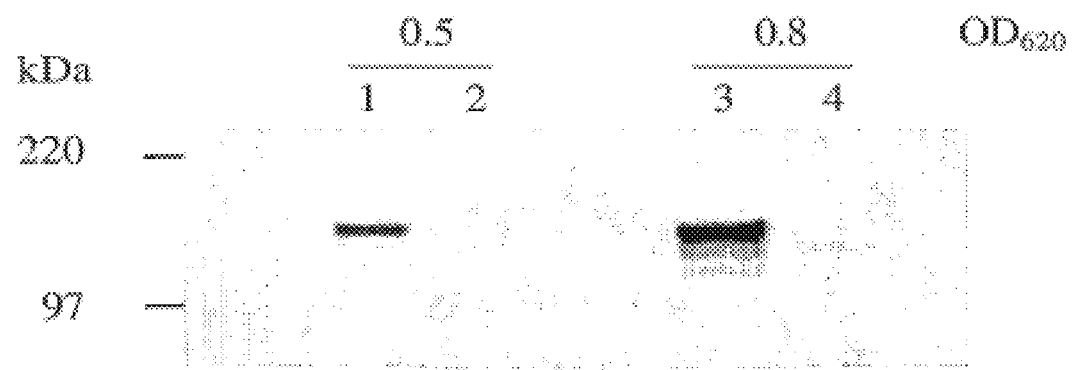
FIG. 40 shows a western blot analysis of supernatants in parallel to FIG. 39.

In marked contrast, supernatant samples of wild-type MC58 showed a band at ~140 kDa and its amount was higher in stationary phase than in log phase (FIG. 40, lanes 3 & 1). The stationary phase sample also showed a reactive band at ~100 kDa.

It will be understood that the invention is described above by way of example only modifications may be made whilst remaining within the scope and spirit of the invention.

TABLE I

Characteristics of 26 *N. meningitidis* strains and their nadA gene allele

| Strain | Serogroup type:subtype | Clonal group | nadA allele | (TAAA) repeats | NadA expression |
|---|---|---|---|---|---|
| 64/69 | NG:15:P1.7,16 | ET-5 | 1 | 4 | + |
| BZ83 | B:15 | ET-5 | 1 | 5 | +++ |
| CU385 | B:4:P1.15 | ET-5 | 1 | 6 | ++ |
| MC58 | B:15:P1.7,16b | ET-5 | 1 | 9 | + |
| BZ169 | B:15:P1.16 | ET-5 | 1 | 12 | ++ |
| 95330* | B:4:P1.15 | ET-5 | 1 | 9 | nd |
| ISS1104 | B:15:P1.7,16 | nd | 1 | 4 | + |
| ISS1071 | B:15:P1.7,16 | nd | 1 | 5 | +++ |
| ISS832 | B:15:P1.7 | nd | 1 | 5 | ++ |
| NM119 | B,4.P1.15 | nd | 1 | 6 | nd |
| NM066 | B:15:P1.7,16 | nd | 1 | 12 | nd |
| 90/18311 | C:NT:P1.5 | ET-37 | 2 | 9 | ++ |
| NGP165 | B:NT:P1.2 | ET-37 | 2 | 9 | ++ |
| FAM18 | C:2a:P1.5,2 | ET-37 | 2 | 9 | nd |
| M986 | B:2a:P1.5,2 | ET-37 | 2 | 12 | ++ |
| ISS1024* | C:2b:P1.5 | nd | 2 | 9 | ++ |
| ISS838 | C:2a:P1.5,2 | nd | 2 | 6 | ++ |
| PMC8 | C: | nd | 2 | 10 | ++++ |
| 961-5945 | B:2b:P1.21,16 | A4 | 2 | 12 | +++ |
| ISS759* | C:2b:P1.2 | nd | 3 | 8 | ++++ |
| F6124 | A | Subgroup III | 3 | 9 | + |
| NMB | B:2b:P1.5,2 | nd | 3 | 12 | ++ |
| 8047 | B:2b:P1.2 | nd | 3 | 12 | +++ |
| 2996 | B:2b:P1.5-1,2 | nd | 3 | 12 | +++ |
| C11 | C:NT:P1.1 | nd | 3 | 12 | +++ |
| 973-1720* | C:2b:P1.2 | A4 | 3 | 12 | +++ |

*indicates that the strain carriers a minor variant of the relevant allele
nd = not done

TABLE II

Characteristics of *N. meningitidis* strains analysed for NadA expression

| ST | ET | Strain | Year | Serogroup:type:subtype | Country | Disease | NadA gene |
|---|---|---|---|---|---|---|---|
| 74 | ET5 | MC58 | 1985 | B:15:P1.7,16b | UK | case | + |
| 32 | ET5 | H44/76 | 1976 | B:15:P1.7,16 | Norway | case | + |
| 32 | ET5 | BZ169 | 1985 | B:15:P1.16 | Netherlands | case | + |
| 32 | ET5 | 30/00 | 2000 | B:15:P1.7,16 | Norway | case | + |
| 33 | ET5 | N44/89 | 1989 | B:4,7:P1.19,15 | Brazil | case | + |
| 34 | ET5 | BZ83 | 1984 | B:15 | Netherlands | case | + |
| — | ET5 | 72/00 | 2000 | B:15:P1.7,13 | Norway | case | + |
| — | ET5 | 39/99 | 1999 | C:15:P1.7,16 | Norway | case | + |
| — | ET5 | M4102 | 1996 | B:ND | USA | case | + |
| — | ET5 | 95330 | 1995 | B:4:P1.15 | Canada | case | + |
| — | ET5 | 2201731 | 1993 | NG:4:P1.15 | Iceland | carrier | + |
| — | ET5 | 64/96 | 1996 | NG:15:P1.7,16 | Norway | carrier | + |
| — | ET5 | CU385 | 1980 | B:4:P1.15 | Cuba | case | + |
| — | ET5 | 8680 | 1987 | B | Chile | case | + |
| — | ET5 | 204/92 | 1992 | B | Cuba | case | + |
| — | ET5 | EG329 | 1985 | B | Germany | case | + |
| — | ET5 | NG080 | 1981 | B | Norway | case | + |
| — | ET5 | NG144/82 | 1982 | B | Norway | case | + |
| — | ET5 | NG PB24 | 1985 | B | Norway | case | + |
| — | ET5 | 196/87 | 1987 | C | Norway | case | + |
| — | ET5 | Mk521/99 | 1999 | B | Ivory Coast | case | + |
| — | ET5 | GR 4/00 | 2000 | — | Greece | case | + |
| 11 | ET37 | FAM18 | 1983 | C:2a:P1.5,2 | USA | case | + |
| 11 | ET37 | L93/4286 | 1993 | C | UK | case | + |
| — | ET37 | NGP165 | 1974 | B:NT:P1.2 | Norway | — | + |
| — | ET37 | M986 | 1963 | B:2a:P1.5,2 | USA | case | + |
| — | ET37 | C4678 | 1998 | C:2a:P1.5,2 | Germany | case | + |
| — | ET37 | 95N477 | 1995 | B:2a:P1.2 | Australia | case | − |
| — | ET37 | BRAZ10 | 1976 | C | Brazil | case | + |
| — | ET37 | F1576 | 1984 | C | Ghana | case | + |
| — | ET37 | M597 | 1988 | C | Israel | case | + |
| — | ET37 | 500 | 1984 | C | Italy | case | + |
| — | ET37 | D1 | 1989 | C | Mali | case | + |
| — | ET37 | NG P20 | 1969 | B | Norway | case | + |

TABLE II-continued

Characteristics of N. meningitidis strains analysed for NadA expression

| ST | ET | Strain | Year | Serogroup:type:subtype | Country | Disease | NadA gene |
|---|---|---|---|---|---|---|---|
| — | ET37 | MA-5756 | 1985 | C | Spain | case | + |
| — | ET37 | 38VI | 1964 | B | USA | carrier | + |
| — | ET37 | N1/99 | 1999 | C:2a | Norway | case | + |
| — | ET37 | N28/00 | 2000 | W-135:2a | Norway | case | + |
| 66 | A4 | 973-1720 | 1997 | C:2b:P1.2 | Australia | case | + |
| 153 | A4 | 961-5945 | 1996 | B:2b:P1.21,16 | Australia | case | + |
| — | A4 | 5/99 | 1999 | B:2b:P1.5,2 | Norway | case | + |
| — | A4 | 312294 | 1995 | C:2b:P1.5,2 | UK | case | + |
| — | A4 | 96217 | 1996 | B:2b:P1.5,10 | Canada | case | + |
| — | A4 | G2136 | 1986 | B | UK | case | + |
| — | A4 | 312 901 | 1996 | C | UK | case | + |
| — | A4 | AK22 | 1992 | B | Greece | case | + |
| — | A4 | BZ10 | 1967 | B | Holland | case | + |
| — | A4 | BZ163 | 1979 | B | Holland | case | + |
| — | A4 | B6116/77 | 1977 | B | Iceland | case | + |
| — | A4 | 94/155 | 1994 | C | New Zealand | case | + |
| — | A4 | SB25 | 1990 | C | South Africa | case | + |
| — | A4 | N53/00 | 2000 | C:2b:P1.5,2 | Norway | case | + |
| — | A4 | N62/00 | 2000 | C:2b:P1.5,2 | Norway | case | + |
| 41 | Lin.III | BZ198 | 1986 | B:NT | Netherlands | case | − |
| 42 | Lin.III | M198/254 | 1998 | B:4:P1.4 | New Zealand | case | − |
| 158 | Lin.III | 972-0319 | 1997 | B:NT:P1.4 | Australia | case | − |
| 159 | Lin.III | 980-2543 | 1998 | B:NT:P1.4 | Australia | case | − |
| 1127 | Lin.III | 67/00 | 2000 | B:4,7 | Norway | case | − |
| — | Lin.III | 93/114 | 1993 | C:4:P1.4 | Belgium | case | − |
| — | Lin.III | M198/172 | 1998 | B:4:P1.4 | New Zealand | case | − |
| — | Lin.III | 347/97 | 1997 | B:4:P1.4 | New Zealand | case | − |
| — | Lin.III | 386/98 | 1998 | B:4:P1.4 | New Zealand | case | − |
| — | Lin.III | 389/98 | 1998 | B:4:P1.4 | New Zealand | case | − |
| — | Lin.III | 392/98 | 1998 | B:4:P1.4 | New Zealand | case | − |
| — | Lin.III | 394/98 | 1998 | B:4:P1.4 | New Zealand | case | − |
| — | Lin.III | 400 | 1991 | B | Austria | case | − |
| — | Lin.III | M40/94 | 1994 | B | Chile | case | − |
| — | Lin.III | AK50 | 1992 | B | Greece | case | − |
| — | Lin.III | M-101/93 | 1993 | B | Iceland | case | − |
| — | Lin.III | 931905 | 1993 | B | Netherlands | case | − |
| — | Lin.III | 91/40 | 1991 | B | New Zealand | case | − |
| — | Lin.III | 50/94 | 1994 | B | Norway | case | − |
| — | Lin.III | N45/96 | 1996 | B | Norway | case | − |
| — | Lin.III | 88/03415 | 1988 | B | Scotland | case | − |
| 1 | s I | BZ133 | 1977 | B:NT | Netherlands | case | − |
| 5 | s III | F6124 | 1988 | A | Chad | case | + |
| 4 | s IV-1 | 205900 | 1990 | A4,21:P1.7:1 | Mali | case | − |
| 4 | s IV-1 | Z2491 | 1983 | A | Gambia | case | − |
| 12 | other | NG3/88 | 1988 | B:8(2):P1.1 | Norway | case | − |
| 13 | other | NG6/88 | 1988 | B:NT:P1.1 | Norway | case | − |
| 14 | other | NGF26 | 1988 | B:NT:P1.16 | Norway | carrier | − |
| 15 | other | NGE31 | 1988 | B:NT | Norway | carrier | − |
| 18 | other | 528 | 1989 | B:nd | Russia | case | − |
| 20 | other | 1000 | 1988 | B:NT:P1.5 | Russia | case | − |
| 22 | other | A22 | 1986 | W-135 | Norway | carrier | − |
| 26 | other | NGE28 | 1988 | B:4 | Norway | carrier | + |
| 29 | other | 860800 | 1986 | Y | Netherlands | case | − |
| 31 | other | E32 | 1988 | Z | Norway | carrier | − |
| 35 | other | SWZ107 | 1986 | B:4:P1.2 | Switzerland | case | − |
| 36 | other | NGH38 | 1988 | B:NT:P1.3 | Norway | carrier | − |
| 38 | other | BZ232 | 1964 | B:NT:P.2 | Netherlands | case | − |
| 39 | other | E26 | 1988 | X | Norway | carrier | − |
| 43 | other | NGH15 | 1988 | B:8:P1.15 | Norway | carrier | − |
| 47 | other | NGH36 | 1988 | B:8:P1.2 | Norway | carrier | − |
| 48 | other | BZ147 | 1963 | B:NT | Netherlands | case | − |
| 49 | other | 297-0 | 1987 | B:4:P1.15 | Chile | carrier | − |
| 540 | other | 2996 | 1975 | B:2b:P1.5-1,2 | UK | case | + |
| 1034 | other | 96/1101 | 1996 | C:14:P1.1,7 | Belgium | case | − |
| — | other | 15 | 1990 | B:14,19:P1.9,15 | Slovenia | case | − |
| — | other | M1090 | 1996 | B:4 | Israel | case | − |
| — | other | M1096 | 1996 | C:NT:P1.5 | Israel | case | − |
| — | other | B3937 | 1995 | B.22P1.16 | Germany | case | + |
| — | other | 31 | 1993 | B:4 | Finland | case | − |
| — | other | 95074 | 1995 | B:NT:P1.13 | Canada | case | + |
| — | other | 660/94 | 1994 | B:4:P1.6 | Algeria | case | − |
| — | other | 30/93 | 1993 | B:14:P1.14 | Argentina | case | − |
| — | other | 24370 | 1996 | B:ND | South Africa | case | − |
| — | other | 241175I | 1993 | NG:21:P1.16 | Iceland | carrier | − |
| — | other | 171274I | 1993 | NQ:15:- | Iceland | carrier | − |

TABLE II-continued

Characteristics of *N. meningitidis* strains analysed for NadA expression

| ST | ET | Strain | Year | Serogroup:type:subtype | Country | Disease | NadA gene |
|---|---|---|---|---|---|---|---|
| — | other | 65/96 | 1996 | B:4:P1.14 | Norway | carrier | + |
| — | other | 66/96 | 1996 | B:17:P1.15 | Norway | carrier | − |
| — | other | 149/96 | 1996 | B:1,19:P1.5,2 | Belgium | carrier | + |
| — | other | 16060 | 1991 | B:4:P1.14 | Belgium | carrier | − |
| — | other | 16489 | 1991 | NG21:P.1.1 | Norway | carrier | − |
| — | other | 16990 | 1991 | NG:14:P1.5,2,6 | Norway | carrier | − |
| — | other | 2022 | 1991 | NG:4:P1.10 | Norway | carrier | + |
| — | other | M136 | 1968 | B:11:P1.15 | USA | case | − |
| — | other | 860060 | 1988 | X | Holland | case | − |
| — | other | NG H41 | 1986 | B | Norway | carrier | − |
| — | other | NG G40 | 1988 | B | Norway | carrier | − |
| — | other | NG4/88 | 1988 | B | Norway | case | − |
| — | other | EG 327 | 1985 | B | DDR | case | − |
| — | other | EG 328 | 1985 | B | DDR | case | − |
| — | other | 3906 | 1977 | B | China | case | − |
| — | other | NG E30 | 1988 | B | Norway | carrier | − |
| — | other | 71/94 | 1994 | Y | Norway | case | − |
| — | other | DK24 | 1940 | B | Denmark | case | − |
| — | — | C11 | 1965 | C:16:P1.7a,1 | Germany | — | + |
| — | — | pmc8 | — | C | — | — | + |
| — | — | NMB | 1968 | B:2b:P1.5,2 | USA | case | + |
| — | — | 8047 | 1978 | B:2b:P1.2 | USA | case | + |
| — | — | S3446 | 1972 | B:14:P1.23,14 | USA | case | − |
| — | — | ISS 749 | 1996 | B.14:P1.13 | Italy | case | − |
| — | — | ISS 759 | 1996 | C:2b:P1.2 | Italy | case | + |
| — | — | ISS 832 | 1997 | B:15:P1.7 | Italy | case | + |
| — | — | ISS 838 | 1997 | C:2a:P1.5,2 | Italy | case | + |
| — | — | ISS1001 | 1999 | B:14:P1.13 | Italy | case | − |
| — | — | ISS1024 | 2000 | C:2b:P1.5 | Italy | case | + |
| — | — | ISS1026 | 2000 | B:4:P1.13 | Italy | case | − |
| — | — | ISS1071 | 2000 | B:15:P1.7,16 | Italy | case | + |
| — | — | ISS1102 | 2000 | B:15:P1.4 | Italy | case | − |
| — | — | ISS1104 | 2000 | B:15:P1.7,16 | Italy | case | + |
| — | — | ISS1106 | 2000 | B:4:P1.4 | Italy | case | − |
| — | — | ISS1113 | 2000 | C:2a:P1.5 | Italy | case | + |
| — | — | NI002/90 | — | — | Brazil | — | + |
| — | — | IMC2135 | — | — | Brazil | — | + |
| — | — | NM001 | — | B:4:P1.4 | UK | case | − |
| — | — | NM002 | — | B:NT:P1.16 | UK | case | − |
| — | — | NM004 | — | B:NT:P1.14 | UK | case | − |
| — | — | NM008 | — | B:4:P1.4 | UK | case | − |
| — | — | NM009/10 | — | B:4:P1.3,6 | UK | case | − |
| — | — | NM021 | — | B:4:P1.16 | UK | case | − |
| — | — | NM036 | — | C:2a:P1.10 | UK | case | + |
| — | — | NM037 | — | B:2b:P1.10 | UK | case | + |
| — | — | NM050 | — | B:NT:P1.9 | UK | case | − |
| — | — | NM058 | — | B:NT:NST | UK | case | − |
| — | — | NM066 | — | B:15:P1.7,16 | UK | case | + |
| — | — | NM067 | — | C:2a:NST | UK | case | + |
| — | — | NM069 | — | B:15:P1.7,16 | UK | case | + |
| — | — | NM081 | — | C:2a:P1.5,2 | UK | case | + |
| — | — | NM088 | — | C:2a:P1.5,2 | UK | case | + |
| — | — | NM092 | — | B:4:P1.4 | UK | case | − |
| — | — | NM106 | — | B:NT:P1.4 | UK | case | − |
| — | — | NM107/8 | — | B:4:P1.4 | UK | case | − |
| — | — | NM117 | — | B:21:P1.9 | UK | case | − |
| — | — | NM119 | — | B:4:P1.15 | UK | case | + |
| — | — | NM131 | — | B | UK | case | − |
| — | — | NM145 | — | C | UK | case | + |
| — | — | NM154 | — | C:NT:P1.5,2 | UK | case | + |
| — | — | NM156 | — | B:15:P1.16 | UK | case | + |
| — | — | NM167 | — | B | UK | case | − |
| — | — | NM184 | — | B:NT:P1.5,2 | UK | case | − |
| — | — | NM186 | — | B | UK | case | − |
| — | — | NM188 | — | B | UK | case | + |
| — | — | NM200 | — | B:4:P1.4 | UK | case | − |

TABLE III

SEQUENCE LISTING

| SEQ ID NO: | Description |
|---|---|
| 1 | allele 1 of 961 |
| 2 | allele 2 of 961 |
| 3 | allele 3 of 961 |
| 4 | allele 1 of 961 (first-ATG start) |
| 5 | allele 2 of 961 (first-ATG start) |
| 6 | allele 3 of 961 (first-ATG start) |
| 7 | variant allele 2 of 961 in strain ISS1024 |
| 8 | variant allele 2 of 961 (first-ATG start) in strain ISS1024 |
| 9 | variant allele 3 of 961 in strains 973-1720 and ISS759 |
| 10 | variant allele 3 of 961 (first-ATG start) in strains 973-1720 and ISS759 |
| 11 | 961 allele 1/2 chimera (strain 95330) |
| 12 | 961 allele 1/2 chimera (strain 95330) (first-ATG start) |
| 13 | 961 allele C |
| 14 | 961 allele C (first-ATG start) |
| 15 | coding sequence for SEQ ID 13 |
| 16-31 | PCR primers |
| 32 | SEQ ID 650 from WO99/24578 |
| 33-39 | Domain derivatives of SEQ ID 32 |

We claim:

1. An isolated protein comprising:
   (a) an amino acid sequence having at least 90% sequence identity to the amino acid sequence of SEQ ID NO: 2; or
   (b) a fragment of 170 or more amino acids of SEQ ID NO: 2, wherein the isolated protein lacks the C-terminal membrane anchor corresponding to amino acids 310-362 of SEQ ID NO: 1.

2. The isolated protein of claim 1 which comprises the amino acid sequence of (a) and also lacks 1 or more N-terminal amino acid residues of SEQ ID NO: 2.

3. The isolated protein of claim 1 which comprises the fragment of (b) and also lacks 1 or more N-terminal amino acid residues of SEQ ID NO: 2.

4. The isolated protein of claim 1 which comprises the fragment of (b) and also lacks the N-terminal leader peptide anchor corresponding to amino acids 1-23 of SEQ ID NO: 1.

5. The isolated protein of claim 1 which includes the heptad sequence of SEQ ID NO: 2 $(AA_1AA_2AA_3AA_4AA_5AA_6AA_7)_r$ wherein: $AA_1$ is Leu, Ile, Val or Met; each of $AA_2$, $AA_3$, $AA_4$, $AA_5$, $AA_6$ and AA7 may independently be any amino acid; and r is an integer of 1 or more.

6. An immunogenic composition comprising the protein of claim 1 and an adjuvant.

7. An isolated protein comprising an amino acid sequence having at least 90% sequence identity to the amino acid sequence of SEQ ID NO: 2 lacking the C-terminal membrane anchor corresponding to amino acids 310-362 of SEQ ID NO: 1 and the N-terminal leader peptide corresponding to amino acids 1-23 of SEQ ID NO: 1.

* * * * *